US011692027B2

(12) United States Patent
Kraft et al.

(10) Patent No.: US 11,692,027 B2
(45) Date of Patent: Jul. 4, 2023

(54) ANTIBODY AND PROTEIN THERAPEUTIC FORMULATIONS AND USES THEREOF

(71) Applicant: BOARD OF REGENTS, THE UNIVERSITY OF TEXAS, Austin, TX (US)

(72) Inventors: Edward R. Kraft, Galveston, TX (US); Steven Andrew Giannos, Galveston, TX (US); Bernard Godley, Hitchcock, TX (US)

(73) Assignee: Board of Regents, The University of Texas System, Austin, TX (US)

(*) Notice: Subject to any disclaimer, the term of this patent is extended or adjusted under 35 U.S.C. 154(b) by 44 days.

(21) Appl. No.: 16/337,103

(22) PCT Filed: Sep. 25, 2017

(86) PCT No.: PCT/US2017/053185
§ 371 (c)(1),
(2) Date: Mar. 27, 2019

(87) PCT Pub. No.: WO2018/063963
PCT Pub. Date: Apr. 5, 2018

(65) Prior Publication Data
US 2020/0031917 A1 Jan. 30, 2020

Related U.S. Application Data

(60) Provisional application No. 62/400,977, filed on Sep. 28, 2016.

(51) Int. Cl.
*A61K 39/395* (2006.01)
*C07K 16/22* (2006.01)
*A61K 38/06* (2006.01)
*A61K 38/17* (2006.01)
*A61K 47/10* (2017.01)
*A61K 47/18* (2017.01)
*A61K 47/26* (2006.01)
*A61K 9/00* (2006.01)
*A61K 9/08* (2006.01)

(52) U.S. Cl.
CPC ............ *C07K 16/22* (2013.01); *A61K 38/063* (2013.01); *A61K 38/179* (2013.01); *A61K 47/10* (2013.01); *A61K 47/183* (2013.01); *A61K 47/26* (2013.01); *A61K 9/0048* (2013.01); *A61K 9/0078* (2013.01); *A61K 9/08* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| 5,688,651 | A | 11/1997 | Solomon |
|---|---|---|---|
| 6,171,586 | B1 | 1/2001 | Lam et al. |
| 7,276,477 | B2 | 10/2007 | Osslund et al. |
| 7,648,702 | B2* | 1/2010 | Gombotz ............... A61P 15/00 424/134.1 |
| 8,388,953 | B2 | 3/2013 | Gan et al. |
| 8,609,817 | B2 | 12/2013 | Leung et al. |
| 8,613,919 | B1 | 12/2013 | Ma et al. |
| 8,772,231 | B2 | 7/2014 | Maggio |
| 8,776,785 | B2 | 7/2014 | Nix |
| 8,776,786 | B2 | 7/2014 | Kraft et al. |
| 8,828,947 | B2 | 9/2014 | Gombotz et al. |
| 8,846,044 | B2 | 9/2014 | Maggio et al. |
| 8,948,863 | B2 | 2/2015 | Kraft et al. |
| 9,023,357 | B2 | 5/2015 | Ma et al. |
| 9,155,745 | B2 | 10/2015 | Gurny et al. |
| 9,226,961 | B2 | 1/2016 | Gokarn et al. |
| 2007/0071675 | A1 | 3/2007 | Wu et al. |
| 2011/0257104 | A1 | 10/2011 | Chennamsetty et al. |
| 2015/0034557 | A1 | 2/2015 | Pouchoulin |
| 2015/0071936 | A1 | 3/2015 | Cadila |
| 2015/0157715 | A1 | 6/2015 | Kraft |
| 2015/0205912 | A1 | 7/2015 | Agrawal et al. |
| 2015/0216977 | A1 | 8/2015 | Adocia |

FOREIGN PATENT DOCUMENTS

| WO | 2007/149334 A3 | 12/2007 |
|---|---|---|
| WO | 2015/071348 A1 | 5/2015 |

(Continued)

OTHER PUBLICATIONS

International Search Report dated Dec. 5, 2017, issued in counterpart PCT application No. PCT/US2017/053185.

(Continued)

*Primary Examiner* — Yunsoo Kim
(74) *Attorney, Agent, or Firm* — Thomas | Horstemeyer, LLP

(57) ABSTRACT

The present disclosure provides pharmaceutical compositions for monoclonal antibodies, antibody-related products, therapeutic proteins, peptides and other biopharmaceuticals. The compositions provide initial and long term stability of the biopharmaceutical agent, rendering them suitable for parenteral, pulmonary, transdermal, topical, intradermal, intrascleral, intracorneal, ocular and other forms of delivery. The compositions and methods lead to higher yields in dilute solutions and reduce unwanted aggregation of the biopharmaceutical agent. The compositions and methods also allow for disaggregation of previously aggregated proteins and protection from aggregation upon dilution. Additionally, provided are non-aggregating antibody reagents for analytical immunoassays including ELISA methods. The invention provides compositions and methods for topical, enteral, parenteral, pulmonary and other forms of delivery of biologically active substances. Also provided is the transscleral, transcorneal or transocular delivery of high molecular weight, biologically active substances to a patient, with or without pulsed infrared (IR) light. The compositions may also incorporate nanotechnologies to formulate the active substances.

14 Claims, 26 Drawing Sheets

(56) References Cited

FOREIGN PATENT DOCUMENTS

WO 2015/200324 A1 12/2015
WO 2016/073915 A1 5/2016
WO 2017/129685 A1 8/2017

OTHER PUBLICATIONS

Deissler, Heidrun L., et al., "Capacity of aflibercept to counteract VEGF-stimulated abnormal behavior of retinal microvascular endothelial cells," Experimental Eye Research, vol. 122 (2014), pp. 28-31.
Shire, Steven J., Monoclonal Antibodies, Meeting the Challenges in Manufacturing, Formulation, Delivery and Stability of Final Drug Product, Woodhead Publishing Series in Biomedicine: No. 77 (2015).
Goswami, Sumit, et al., "Developments and Challenges for mAb-Based Therapeutics," Antibodies, vol. 2 (2013), pp. 452-500.
European Office Action, EP Patent Application No. 17857248.3, dated Jul. 26, 2022 (14 pages).

\* cited by examiner

FIG. 13   Disaggregation and Pre-Exposure to Formula 14

FIG. 20

Formula 14
dilution from starting concentration

| Antibody ng/mL Concentration | Dilution factor Fraction | Trehalose % | Trehalose g/mL | Tween 80 % | Tween 80 mL/mL | Arginine % | Arginine mM/ml |
|---|---|---|---|---|---|---|---|
| 70.3125 | 0.0004882 | 0.0036615 | 0.00003662 | 0.000019528 | 0.00000020 | 0.00008495 | 0.004882 |
| 140.625 | 0.0009765 | 0.00732375 | 0.00007324 | 0.00003906 | 0.00000039 | 0.000169911 | 0.009765 |
| 281.25 | 0.0019531 | 0.01464825 | 0.00014648 | 0.000078124 | 0.00000078 | 0.000339839 | 0.019531 |
| 562.5 | 0.0039062 | 0.02929665 | 0.00029297 | 0.000156248 | 0.00000156 | 0.000679679 | 0.039062 |
| 1000 | 0.0069444 | 0.0520833 | 0.00052083 | 0.0002777 | 0.00000278 | 0.001208326 | 0.069444 |
| 1125 | 0.0078125 | 0.05859375 | 0.00058594 | 0.0003125 | 0.000003125 | 0.001359375 | 0.078125 |
| 2250 | 0.015625 | 0.1171875 | 0.001171875 | 0.000625 | 0.00000625 | 0.00271875 | 0.15625 |
| 4500 | 0.03125 | 0.234375 | 0.00234375 | 0.00125 | 0.0000125 | 0.0054375 | 0.3125 |
| 9000 | 0.0625 | 0.46875 | 0.0046875 | 0.0025 | 0.000025 | 0.010875 | 0.625 |
| 18000 | 0.125 | 0.9375 | 0.009375 | 0.005 | 0.00005 | 0.02175 | 1.25 |
| 36000 | 0.25 | 1.875 | 0.01875 | 0.01 | 0.0001 | 0.0435 | 2.5 |
| 72000 | 0.5 | 3.75 | 0.0375 | 0.02 | 0.0002 | 0.087 | 5 |
| 144000 | 1 | 7.5 | 0.75 | 0.04 | 0.0004 | 0.174 | 10 |
| Per 100 ml | | 7.5g/100 | | .0004 ml/100 | | .174g/100 | 100mM/100 |
| Per/mL | | .75g/mL | .75g/mL | .0004ml/mL | .0004ml/mL | .00174g/mL | 10mM/mL |

FIG. 32A
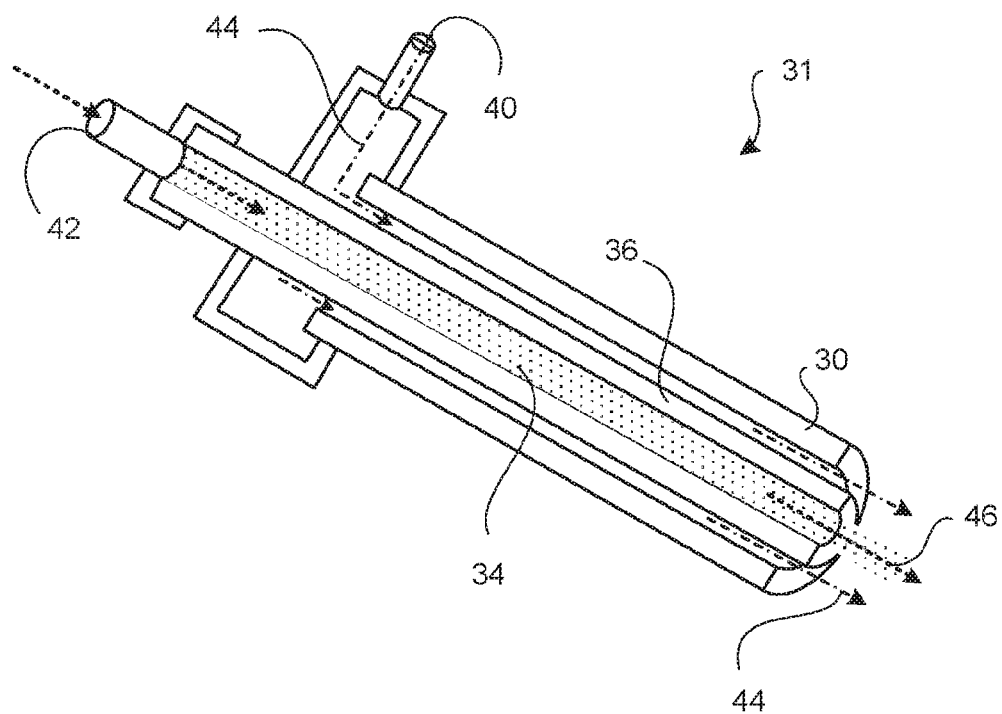
FIG. 32B
FIG. 32C
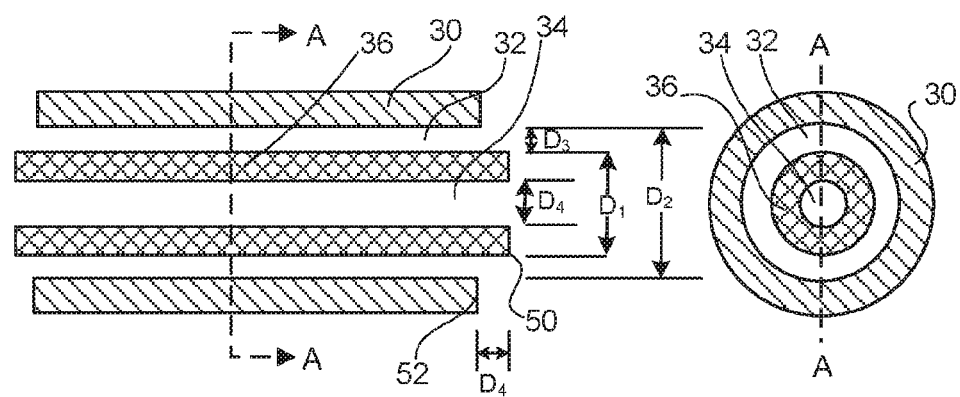

ANTIBODY AND PROTEIN THERAPEUTIC FORMULATIONS AND USES THEREOF

CROSS-REFERENCE TO RELATED APPLICATIONS

This application claims priority based on PCT/US17/53185, filed Sep. 25, 2017, which in turn claims priority based on U.S. Provisional Application Ser. No. 62/400,977, filed Sep. 28, 2016, each of which are incorporated herein by reference in their entireties.

FIELD OF THE INVENTION

This invention relates generally to pharmaceutical compositions for monoclonal antibodies, antibody-related products, therapeutic proteins, peptides and other biopharmaceuticals.

BACKGROUND OF THE INVENTION

Without limiting the scope of the invention, its background is described in connection with compositions and methods thereof that increase stability and reduce the aggregation of peptides and proteins and with the delivery and/or controlled release of drugs and biologically active substances into or across a mammalian tissue surface.

The number of people visually impaired in the world is estimated to be 285 million, of which 39 million are blind and 246 million have low vision. Of these, 65% of people who are visually impaired and 82% of all blind are 50 years and older. See Pascolini D and Mariotti S P. Global estimates of visual impairment: 2010. *Br J Ophthalmol.* 96(5) (2012) 614-8. Age-related macular degeneration (AMD) is a progressive, degenerative disease of the retina that occurs with increasing incidence with age and ranks third among the global causes of visual impairment. See Pascolini supra.

Exudative age-related macular degeneration ("AMD") is caused by new, abnormal blood vessel growth (neovascularization) in the subretinal layers, leading to vascular leaks, bleeding, and progressive vision loss. Vascular endothelial growth factor (VEGF) is a signal protein produced by cells that stimulates vasculogenesis and angiogenesis. VEGF has been implicated in the development and progression of neovascular AMD. When VEGF is overexpressed, it can contribute to disease. Overexpression of VEGF can cause vascular disease in the retina of the eye and other parts of the body.

The commercial development of therapeutic monoclonal antibodies began in the early 1980's, and by 1986 the first therapeutic monoclonal antibody (mAb), Orthoclone OKT3, was approved for the prevention of kidney transplant rejection. As of 2015, the highly dynamic late-stage commercial pipeline of recombinant therapeutics now includes nearly 50 molecules. See Reichert J M, Antibodies to Watch, *mAbs* 7:1 (2015) 1-8. The majority of approved antibody drugs are used to treat cancer and inflammation. However, two of these monoclonal antibodies, bevacizumab (AVASTIN®) and ranibizumab (LUCENTIS®), and the fusion protein, aflibercept, show anti-VEGF properties and may be used to treat age related macular degeneration (AMD). Other mAbs are used to treat autoimmune diseases such as Crohn's disease and ulcerative colitis, while still others help to prevent acute rejection of kidney transplants and moderate-to-severe allergic asthma.

One of the major complications of manufacturing and working with mAbs is the tendency for mAb aggregation. See Vazquez-Rey M and Lang D A. Aggregates in monoclonal antibody manufacturing processes. *Biotechnology and Bioengineering* 108:7 (2011) 1494-1508; Lowe, D. et al. Aggregation, stability, and formulation of human antibody therapeutics. *Adv. Protein Chem. and Struct. Biol.* 84 (2011) 41-61. Monoclonal antibody fragment drugs tend to aggregate, which greatly reduces the biological activity of the agent. See Cromwell M E M, et al. Protein Aggregation and Bioprocessing. *The AAPS Journal* 8(3) (2006) E572-E579. Indeed, aggregation represents the most common form of instability in protein drugs. Various excipients have been suggested to stabilize drugs for extended shelf life. But dilution and brief exposure to body temperatures quickly cause aggregation and diminished drug activity.

Aggregation, in which two or more monomeric units of mAb may bind to each other, is considered an undesirable phenomenon that leads to a decrease in available efficacious product, potential immunogenicity in the patient, and many other potential issues. At any point during or after manufacturing, protein aggregation can occur. Physical stresses on the protein after manufacturing, such as elevated temperatures or agitation during shipping, can induce aggregation. Hydrophobic areas on the surface amino acid sequence are thought to be the most likely locations for seeding aggregation.

Due to their proteinaceous composition, antibodies present generic formulation issues that are similar for most protein therapeutics. See Daugherty, A L and Mrsny, R J. Formulation and delivery issues for monoclonal antibody therapeutics. *Adv. Drug Deliv Rev.* 58(5-6) (2006) 686-706. Various strategies have been developed over the years to counteract protein degradation and aggregation. See Goswami S, et al. Developments and Challenges for mAb-Based Therapeutics. *Antibodies* 2 (2013) 452-500. Briefly, these generally include: adjusting pH, adding buffer and excipients to reduce aggregation by protein folding, or by changing the surface attraction potential. In the area of excipients, non-reducing sugars, cyclodextrins, amino acids, and surfactants are used to stabilize the mAb. See Kamerzell, T J. et al. Protein—excipient interactions: Mechanisms and biophysical characterization applied to protein formulation development. *Advances Drug Delivery Reviews* 63(13) (2011) 1118-1159; Serno, T. et al. Inhibition of agitation-induced aggregation of an IgG-antibody by hydroxypropyl-beta-cyclodextrin. *Journal of Pharmaceutical Sciences* 99(3) (2010) 1193-1206. Despite these strategies, aggregation of biologic agents remains a significant obstacle.

There is a need in the art for methods and formulations to prepare and deliver stable, pharmaceutically active biologic formulations.

BRIEF SUMMARY OF THE INVENTION

Provided herein are methods for the delivery of drugs and biologically active substances, such as antibodies, antibody related products or biotherapeutic agents, with or without pulsed infrared (IR) light. Additionally, the invention provides for the practical nebulization of biotherapeutics for pulmonary drug delivery. The methods and compositions disclosed provide initial and long term stability of the biopharmaceutical agents, rendering them suitable for parenteral, topical, ocular delivery and/or inhaled delivery by aerosolization. The methods and compositions lead to higher yields in dilute solutions and reduce unwanted aggregation of the biopharmaceutical agent. The methods and compositions also allow for disaggregation of previously aggregated proteins and protection from aggregation upon dilution.

Additionally, the methods and compositions provide for an improved diluent reagent in enzyme-linked immunosorbent assay (ELISA) for the stability and unwanted aggregation of the antibody biopharmaceutical agent. Further, provided are methods and compositions for intraocular photokinetic assisted delivery of biopharmaceutical agents as well as nebulization of stabilized biopharmaceutical agents.

In certain embodiments, a pharmaceutical formulation is provided that includes a biopharmaceutical agent in a stabilizing aqueous solution including a sodium phosphate buffer, trehalose, arginine, sodium chloride, and polysorbate 80. In particular embodiments the biopharmaceutical agent is in an amount of 1 ng/ml to 250 mg/ml and is stabilized and prevented from aggregating by the stabilizing aqueous solution. In certain embodiments the stabilizing aqueous solution comprises sodium phosphate in an amount of 5 mM to 150 mM, trehalose in an amount of about 7.5%, arginine in an amount of about 10 mM, sodium chloride in an amount of about 0.3%, and polysorbate 80 in an amount of about 0.04%.

The biopharmaceutical agent may be incorporated in a carrier selected from a liposome, polymeric micelle, nanoparticle, nanotube, dendrimer, or a nanocrystal prior to formulating with the stabilizing aqueous solution.

In certain embodiments the biopharmaceutical agent binds VEGF. Examples of such agents include bevacizumab, ranibizumab, and aflibercept.

The pharmaceutical formulation has a pH in a range of 6.0 to 7.8. However, in certain embodiments the formulation has a pH of about 6.6 to about 6.8.

The pharmaceutical formulation may be applicable to a number of contexts including as a topical ocular pharmaceutical formulation, a parenteral formulation, an inhalable pulmonary pharmaceutical formulation, an intradermal pharmaceutical formulation or an enteral pharmaceutical formulation.

In certain embodiments, the pharmaceutical formulation comprises one or more of a thickening agent, a bioadhesive, a poloxamer, a molecular complexing agent and an antioxidant. Certain of these additives may serve several roles. For example, an added poloxamer may act as a thickening agent and a bioadhesive.

Formulations provided herein reduce aggregation of biopharmaceutical agent, particularly when present in low concentrations, whether or not the agent has been previously lyophilized. In certain embodiments, the biopharmaceutical agent is lyophilized in a stabilizing aqueous solution comprising sodium phosphate in an amount of 5 mM to 150 mM, trehalose in an amount of 6-8%, arginine in an amount of 8-12 mM, sodium chloride in an amount of 0.25-0.50%, and polysorbate 80 in an amount of 0.03-0.05%.

In certain embodiments, a method of administering a pharmaceutical formulation is provided wherein the formulation is delivered with a microchannel concentric tube nebulizing nozzle. In particular embodiments, the microchannel concentric tube nebulizing nozzle comprises an outer carrier gas delivery tube spaced apart from and disposed around an inner drug delivery tube that protrudes past an outer end of the carrier gas delivery tube.

In other embodiments, methods of delivery of a biopharmaceutical formulation to an ocular tissue is provided and is assisted by photokinetic permeation. In particular embodiments the photokinetic permeation is conducted using pulsed infrared light in a wavelength range from 880 to 1450 nm. In certain embodiments the biopharmaceutical agent is selected from bevacizumab, ranibizumab, and aflibercept.

Also provided are methods to reverse aggregation of a biopharmaceutical agent including antibody agents by adding the biopharmaceutical agent to a formulation comprising sodium phosphate in an amount of 5 mM to 150 mM, trehalose in an amount of 6-8%, arginine in an amount of 8-12 mM, sodium chloride in an amount of 0.25-0.50%, and polysorbate 80 in an amount of 0.03-0.05%.

Further provided herein is an immunoassay dilution solution to prevent antibody aggregation that includes a sodium phosphate buffer, trehalose, arginine, sodium chloride, and polysorbate 80. In certain embodiments the immunoassay dilution solution includes an aqueous solution of sodium phosphate in an amount of 5 mM to 150 mM, trehalose in an amount of 6-8%, arginine in an amount of 8-12 mM, sodium chloride in an amount of 0.25-0.50%; and polysorbate 80 in an amount of 0.03-0.05% with the balance being water at a pH of 6.78 to 7.4.

In one embodiment a method for non-invasive transocular delivery of biologically active substances is provided including administering a biopharmaceutical agent to an eye of a patient wherein the biopharmaceutical agent is formulated in a stabilizing solution comprising a sodium phosphate in an amount of 5 mM to 150 mM, trehalose in an amount of 6-8%, arginine in an amount of 8-12 mM, sodium chloride in an amount of 0.25-0.50%, and polysorbate 80 in an amount of 0.03-0.05% with a balance being water at a pH of 6.78 to 7.4. In particular embodiments the stabilizing solution includes 0.3% NaCl, 7.5% trehalose, 10 mM arginine, and 0.04% polysorbate 80, and a 100 mM sodium phosphate buffer with a balance being water at a pH of 6.78. In certain embodiments the stabilizing solution further comprises one or more of a thickening agent, a bioadhesive, an antioxidant, a poloxamer and a molecular complexing agent. Certain of these additives may serve several roles. For example, an added poloxamer may act as a thickening agent and a bioadhesive.

Also provided are methods of assisting delivery of a biopharmaceutical formulation by photokinetic permeation using pulsed infrared light in a wavelength range from 880 to 1450 nm. The photokinetic permeation may be effectively utilized to increase transfer of the biopharmaceutical through an ocular surface. In certain embodiments the biopharmaceutical is an anti-VEGF antibody and the pulsed infrared light is utilized at a wavelength of about 950 nm.

BRIEF DESCRIPTION OF THE DRAWINGS

For a more complete understanding of the present invention, including features and advantages, reference is now made to the detailed description of the invention along with the accompanying figures:

FIG. 15A shows the full range of dilutions. FIG. 15B shows only the lower dilutions FIG. 16A shows the full range of dilutions. FIG. 16B shows only the lower dilutions.

FIG. 17A shows the full range of dilutions. FIG. 17B shows only the lower dilutions.

FIG. 18A shows the higher concentrations. FIG. 18B shows the lower dilutions.

FIG. 19A shows the full range of dilutions. FIG. 19B shows only the lower dilutions.

FIG. 20 is a table showing shows the concentration of trehalose, TWEEN® 80 and arginine in diluted sample using Formula 14.

FIG. 25A shows the permeation at 5 hours and FIG. 25B shows the permeation at 8 hours.

FIG. 26A shows the permeation at 5 hours and FIG. 26B shows the permeation at 8 hours.

FIG. 29A shows the permeation flux over 24 hours and FIG. 29B shows the cumulative amount of antibody permeated over 24 hours.

FIG. 30A shows the permeation flux over 24 hours and FIG. 30B shows the cumulative amount of antibody permeated over 24 hours.

FIG. 32A shows an embodiment of a nebulizer adapted to deliver a viscous solution in accordance with an aspect of the present disclosure. FIG. 32B illustrates a schematic side view of a portion of the nebulizer of FIG. 32A. FIG. 32C shows a cross-sectional schematic view of the outlet of nebulizer of FIG. 32B, taken along line A-A.

DETAILED DESCRIPTION OF THE INVENTION

Figure 1A:
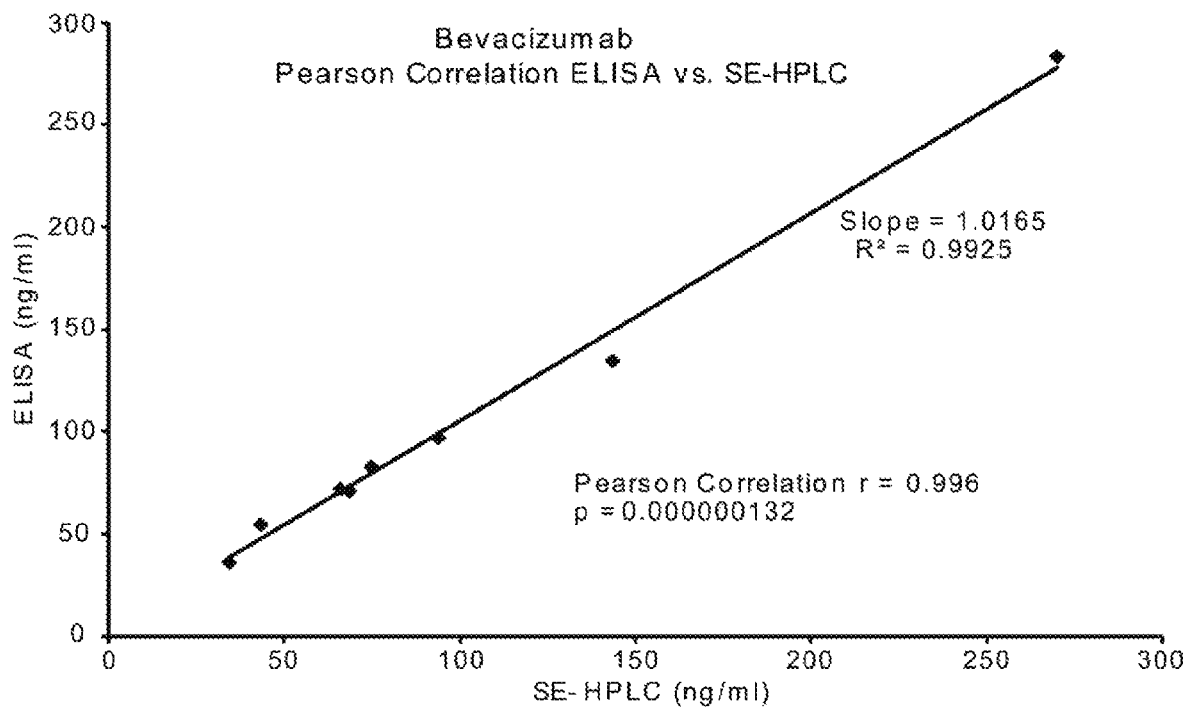
FIGS. 1A-1C provide graphical representation of the correlation between enzyme-linked immunoassay (ELISA) and size exclusion high performance liquid chromatography (SE-HPLC) analytical methods for bevacizumab (FIG. 1A), ranibizumab (FIG. 1B), and aflibercept (FIG. 1C) respectively. The data plots show the Pearson Moment Correlation coefficient r value.

The present disclosure includes formulations for biopharmaceutical agents having an improved aggregation profile as well as methods and apparatus for delivering such formulations including by a nebulizer and using photokinetic delivery. The formulations reduce aggregation and thus improve initial and long term stability. In one embodiment, the invention provides for stable, aqueous pharmaceutical formulations comprising a therapeutically effective amount of a biopharmaceutical, e.g., a monoclonal antibody.

While the making and using of various embodiments of the present invention are discussed in detail below, it should be appreciated that the present invention provides many applicable inventive concepts which can be employed in a wide variety of specific contexts. The specific embodiments discussed herein are merely illustrative of specific ways to make and use the invention and do not delimit the scope of the invention.

To facilitate the understanding of this invention, and for the avoidance of doubt in construing the claims herein, a number of terms are defined below. Terms defined herein have meanings as commonly understood by a person of ordinary skill in the areas relevant to the present invention. The terminology used to describe specific embodiments of the invention does not delimit the invention, except as outlined in the claims.

The terms such as "a," "an," and "the" are not intended to refer to a singular entity unless explicitly so defined, but include the general class of which a specific example may be used for illustration. The use of the terms "a" or "an" when used in conjunction with "comprising" in the claims and/or the specification may mean "one" but may also be consistent with "one or more," "at least one," and/or "one or more than one."

The use of the term "or" in the claims is used to mean "and/or" unless explicitly indicated to refer to alternatives as mutually exclusive. Thus, unless otherwise stated, the term "or" in a group of alternatives means "any one or combination of" the members of the group. Further, unless explicitly indicated to refer to alternatives as mutually exclusive, the phrase "A, B, and/or C" means embodiments having element A alone, element B alone, element C alone, or any combination of A, B, and C taken together.

Similarly, for the avoidance of doubt and unless otherwise explicitly indicated to refer to alternatives as mutually exclusive, the phrase "at least one of" when combined with a list of items, means a single item from the list or any combination of items in the list. For example, and unless otherwise defined, the phrase "at least one of A, B and C," means "at least one from the group A, B, C, or any combination of A, B and C." Thus, unless otherwise defined, the phrase requires one or more, and not necessarily all, of the listed items.

The terms "comprising" (and any form thereof such as "comprise" and "comprises"), "having" (and any form thereof such as "have" and "has"), "including" (and any form thereof such as "includes" and "include") or "containing" (and any form thereof such as "contains" and "contain") are inclusive or open-ended and do not exclude additional, unrecited elements or method steps.

The term "effective" as used in the specification and claims, means adequate to provide or accomplish a desired, expected, or intended result.

The terms "about" or "approximately" are defined as being close to as understood by one of ordinary skill in the art, and in one non-limiting embodiment the terms are defined to be within 10%, within 5%, within 1%, and in certain aspects within 0.5%.

The term "drug carrier matrix", "carrier matrix", "antibody carrier matrix", "carrier matrices" and/or "matrix" refers to the liquid composition comprising dissolved and/or suspended substances used to carry a drug and facilitate handling and application of the drug for an intended use. In this case, the various matrices may comprise water, sugars, amino acids, salts, surfactants, antibodies, preservatives, drugs or other compounds and/or excipients commonly used in pharmacologic or immunoassay compositions. The subject invention discovery is based on analysis of various antibody carrier matrix compositions and the effect of those various carrier matrix compositions on antibody interactions as determined by analytical methods.

In certain embodiments, the drug is a biopharmaceutical agent incorporated in a carrier selected from a liposome, polymeric micelle, nanoparticle, nanotube, dendrimer, or a nanocrystal. Current drug delivery systems include microchips, microneedle-based transdermal therapeutic systems, layer-by-layer assembled systems, and various microparticles produced by ink-jet technology.

As used herein the term "antibody" includes both intact immunoglobulin molecules as well as portions, fragments, and derivatives thereof, such as, for example, Fab, Fab', F(ab')$_2$, Fv, Fsc, CDR regions, or any portion of an antibody that is capable of binding an antigen or epitope including chimeric antibodies that are bi-specific or that combine an antigen binding domain originating with an antibody with another type of polypeptide. The term antibody includes monoclonal antibodies (mAb), chimeric antibodies, humanized antibodies, as well as fragments, portions, regions, or derivatives thereof, provided by any known technique including but not limited to, enzymatic cleavage and recombinant techniques. The term "antibody" as used herein also includes single-domain antibodies (sdAb) and fragments thereof that have a single monomeric variable antibody domain ($V_H$) of a heavy-chain antibody. sdAb, which lack variable light ($V_L$) and constant light ($C_L$) chain domains are natively found in camelids ($V_HH$) and cartilaginous fish ($V_{NAR}$) and are sometimes referred to as "Nanobodies" by the pharmaceutical company Ablynx who originally developed specific antigen binding sdAb in llamas. The modifier "monoclonal" indicates the character of the antibody as being obtained from a substantially homogeneous population of antibodies, and is not to be construed as requiring production of the antibody by any particular method.

The terms "co-administered" and "in combination with" include administration with two or more therapeutic agents either simultaneously, concurrently or sequentially in any order without specific time limits so long as the two or more "co-administered" drugs are present in measureable amounts in a single patient at a given time. In certain embodiments, the therapeutic agents are in the same composition or unit dosage form while in other embodiments, the therapeutic agents are in separate compositions or unit dosage forms. The terms "active agent," "drug," "therapeutic agent," and synonymous terms according to those of skill in the art are used interchangeably herein.

Common terms used for certain chemical reagents may be used interchangeably and is understood by those skilled in the art. For example the term "trehalose" may include but is not limited to α,α trehalose dihydrate, a non-reducing sugar. Polysorbate 20 and polysorbate 80 may be referred to interchangeably by their common trade names TWEEN® 20 and TWEEN® 80 respectively (TWEEN is a registered trademark of Croda Int'l PLC).

Polysorbate 20 is a polysorbate nonionic surfactant that is derived from polyethoxylated sorbitan and lauric acid, includes 20 repeats of polyethylene glycol (PEG), and has the IUPAC name polyoxyethylene (20) sorbitan monolaurate and CAS Number 9005-64-5.

Polysorbate 80 is a polysorbate nonionic surfactant that is derived from polyethoxylated sorbitan and oleic acid, includes 20 repeats of polyethylene glycol (PEG), and has the IUPAC name polyoxyethylene (20) sorbitan monooleate and CAS Number 9005-65-6.

The term "PBS" is a common term used to designate phosphate buffered saline which is a physiologic concentration of sodium chloride salt (137 mM NaCl) and potassium chloride salt (2.7 mM KCl) combined to concentration at about 0.9% in a water solution containing 11.9 mM of phosphate buffers (potassium phosphate monobasic and sodium phosphate dibasic) in a proportion to provide a physiologic pH of about 7.4. The term "BSA" refers to bovine serum albumin, also known as "Fraction V", is a serum albumin protein derived from cow blood. This protein is commonly used in antibody compositions to protect against aggregation in vitro and also used in immunoassays to prevent nonspecific binding of antibodies to plastic or protein surfaces. Unless otherwise noted, terms used shall be the common term known to those skilled in the art.

Formulations for Reducing Aggregation:

Certain formulations disclosed herein are particularly advantageous for applications requiring dilute solutions of protein therapeutics. Usually, mAbs are formulated in high concentrations (>1 mg/ml, e.g., 1-25 mg/ml, or 10-50 mg/mL). Little is known about protein solution dynamics in dilute solutions. The present inventors encountered the problem of instability of dilute solutions while developing and validating methods for mAb in vitro trans-scleral permeation. This phenomenon has recently been reported by others as well. See Chua et al. Optimal buffer for storage of ranibizumab at low concentrations. ARVO. Seattle. Wash., 2016.

In one series of experiments, two-compartment Franz permeation cells were used to model trans-scleral permeation. The Franz apparatus is composed of a drug donor chamber and a drug receiver chamber separated by the test membrane. See e.g. Friend D R. In vitro skin permeation techniques. *J Controlled Release* 18(3) (1992) 235-248. To perform permeation experiments, the starting receiver solution does not contain any permeant mAb drug. As the permeation experiment progresses, the concentration of the drug in the receiver solution increases. However, at early points in the tissue permeation experiment, the drug is still a dilute solution. Published tissue permeation (Franz) cell studies typically use PBS as the recipient media at 37° C. For our experimental work on anti-VEGF mAb, these conditions contributed to mAb aggregation, causing reduced measured concentrations and decreased VEGF binding activity.

In addition to our in vitro permeation studies, prior research by others for determining mAb drug concentration in human fluid samples have utilized enzyme-linked immunosorbent assay (ELISA) assay kits for quantification. High sensitivity ELISA methods require drug samples to be diluted to bring the samples within the usable dynamic range of the method, generally 1-1,000 ng/ml, more typically 1-100 ng/ml. Frequently, the sample is diluted with PBS, which may result in up to 50% loss of the biopharmaceutical agent. Because dilution with PBS increases aggregation, reported drug concentrations may be significantly lower than actual drug concentrations in various in vitro and in vivo studies.

Antibody aggregation in certain solutions can occur very rapidly. High antibody concentration aggregation (>50 mg/ml) is widely known and is important in antibody manufacture and packaging for clinical or laboratory use. Low concentration antibody aggregation is generally controlled in the immunoassay environment through the use of added serum proteins (human or bovine serum albumen, a.k.a. BSA) that are added to mixtures to diminish aggregation potential. Serum derived protein additives, animal or human, are generally disfavored or unacceptable for administration into humans. In addition to advantages in drug delivery, the ability to prevent aggregation in certain immunoassays enables use of diluent reagents that are free of extraneous serum/proteins that may cause non-specific antigen binding or provide cross reactivity of certain antibodies to multiple antigens.

The present inventors have identified a phenomenon wherein low concentrations of antibodies (<1150 ng/ml) tend to aggregate aggressively. This is particularly important in clinical settings wherein dilute antibody formulations are administered ocularly, such as, for example, where anti-VEGF antibody is administered at 50 micro liters (µl) of a 10-40 mg/ml solution into the viscous vitreous humor of the eye. The human eye vitreous contains about 95% water. Insoluble collagens, glycosaminoglycans (hyaluronic acid, chondroitin sulfate and heparin sulfate), metabolites, amino acids, fatty acids, prostaglandins, cells and enzymes. The total soluble protein concentration in vitreous body is between 0.02% and 0.14% (200-1,400 µg/ml), 40% of which is albumin (80-560 µg/ml, 0.008%-0.056%). See Kleinberg T T et al. *Survey of Ophthalmology* 56(4) (2011) 300-323. Typically, antibody based immunoassays use about 1% serum albumin soluble protein to retard antibody aggregation. The relatively low concentration of total soluble proteins and albumin in the vitreous body may offer little protection from antibody aggregation within the vitreous body compared to the normal total soluble protein in the circulating blood of 6.4-8.3% with 3.5-5% of that portion being albumin. Added albumin into any antibody composition would be pharmacologically unacceptable for human administration due to possible immune interactions.

In the case of intravitreal injection, the vitreous of the eye has a concentration gradient from 10-40 mg/ml at the injection deposition site toward a 0 mg/ml concentration throughout the adjacent vitreous. A low concentration zone precedes the drug front as it slowly permeates throughout the vitreous volume. It has been estimated that it takes about one full day for antibodies from an intravitreal injection to reach concentration equilibrium within the vitreous body. The low concentration drug front has conditions that promote low concentration antibody aggregation. Once antibodies aggregate, dis-aggregation is difficult or impossible without some form of intervention.

Similarly, high concentration antibody formulations in a transportation package from a manufacturer are diluted for administration into a patient, for example, into an intravenous solution of 0.9% saline. See Kumru O S et al. Compatibility, physical stability, and characterization of an IgG4 monoclonal antibody after dilution into different intravenous administration bags. *J Pharmaceutical Sciences* 101(10) (2012) 3636-3650. Not only is the diluent composition a factor for aggregation, but the present inventors have found that the dilution itself is also very important. It is known that the anti-VEGF antibody drugs, bevacizumab and ranibizumab, are very prone to diminished function once removed from the manufacturer's vial and diluted. During dilution, the concentration gradient again provides a front wherein there is a low antibody concentration front that moves throughout the diluent volume within the diluent vessel, resulting in less remaining active antibody in the final solution.

Prior research by others for determining mAb drug concentration in human fluid as well as other liquid matrices have utilized enzyme linked immunoassay (ELISA) assay methods for antibody quantification. The basic operational principal is that a specific binding site on an antibody will bind with a specific target antigen binding site. Although the exact method protocols may vary, typically the subject antibody is reacted and attached by specific binding to a target protein antigen. A secondary antibody with a covalently bound enzyme conjugant is then reacted and attached to the subject antibody. A solution containing 3,3',5,5'-Tetramethylbenzidine (TMB) reacts with the enzyme and colorizes the individual compartments containing the antigen/antibody/antibody conjugant complex. The colorizing reaction is concentration dependent which then allows for a concentration dependent optical absorption gradient to be produced. An optical density standard regression curve of known antibody concentrations can be constructed to interpolate and/or extrapolate an unknown sample. Depending on the antibody, this method can be very specific. Micro-titer multi-well (300 µL) plates are generally used as the reaction platform to conserve reagents. The plate immobilizes the several antigen/antibody complexes so that the final colored optical density readings can be performed without loss of signaling sources. The number of antibodies, generally expressed in weight per volume (i.e. nanograms/milliliter, ng/ml), that bind with a specific antigen are directly related to the derived optical density of the colorized reactions. Thus, a higher optical density indicates a greater number of successful antibody/antigen binding reactions and therefore indicating a higher concentration of the subject antibody.

Generally, a range of known concentrations of antibodies are correlated with the derived optical density of the binding reaction which will then generate the standard concentration curve. The linear range of this curve generates a slope value and slope function. A higher slope value indicates more antibody/antigen attachments at a particular antibody concentration. Conversely, a lower slope value would indicate fewer antibody/antigen attachments. A condition under which a concentration standard curve is derived may produce a linear optical density function over a range of antibody concentrations regardless of the number of antibody/antigen binding actions. Multiple antibody preparation conditions and methods can be prepared on the same ELISA micro-titer plate providing the same test evaluation conditions for a comparison of the different preparation conditions. For example, serial antibody dilutions using different diluent compositions can be compared side by side. Derived optical density values and resulting regression curve slopes can be compared to indicate if one condition is preferable to another condition using the slope value as the comparator.

ELISA methods have intrinsic quantification errors. These can be due to the high sensitivity, the many process steps, reagent variability, environmental variability and the relatively small amounts of reagents utilized with the associated micro-dispensing methods. High sensitivity ELISA methods may require drug test samples to be diluted 10-1,000 times or more to bring the samples within the usable dynamic range of the method, generally 1-1,000 ng/ml, but more typically 1-200 ng/ml. Small errors in dilution or user variability can be greatly amplified when ELISA concentration results are extrapolated to accommodate dilution factors. Additionally, diluents used for concentration standard curve generation may be different from the diluents used for unknown sample dilution. Furthermore, any effects from the sample dilution itself cannot be evaluated because of the narrow dynamic range of the method requiring all samples to be extensively diluted. ELISA does not offer an undiluted control to base a comparison over an extended range of concentrations beyond the method linear range.

There may be day to day variations and plate to plate variations in the derived optical density generated from a particular sample using ELISA methodology. However, under the same test conditions, i.e. using the same test plate to run comparator samples side by side, same ambient temperature, same reagent composition and other parameters used for analysis, different antibody composition matrices can be evaluated for drug carrier matrix effects by comparison of the area slopes generated by the individual carrier matrix.

Antibody concentration in a liquid carrier matrix can also be determined by size exclusion high performance liquid chromatography (SE-HPLC). Briefly, in this analytical method, a column is packed with derivatized silica with a selected pore size. A steady stream of aqueous buffer (mobile phase) is passed through the column containing the porous silica (stationary phase). A defined volume of a subject sample containing various compounds is injected into the mobile phase stream. The sample material passes in and out of the silica stationary phase in a rate dependent function wherein larger molecular weight compounds pass more quickly through the column while smaller compounds pass more slowly thus providing a separation of the various constituents of the sample. The separated sample stream passes through an optical light detector that generates a light absorption profile based on optical density for each of the compounds. The optical density absorption with the rise and fall time of the optical density generates a positive curve peak. The peak with the rise and fall is derived to generate an area under the peak (area under the curve) value herein known as "area." The area is directly proportional to the amount of subject compound in the sample. The amount of time from the injection of the sample into the mobile phase to when a peak is generated (retention time) is highly reproducible and consistent and does not significantly vary from sample to sample.

Generally, a serial dilution solution set with known concentrations of the subject compound is prepared and run through the SE-HPLC system. The SE-HPLC areas derived from each of the concentrations is plotted against the known concentration and a standard concentration curve is constructed. The standard concentration curve slope and intercept can provide a mathematical formula that can determine and quantify an unknown sample. If, for example, antibodies in a liquid matrix aggregate with one or more other antibodies, the molecular weight of the combination will increase. The molecular weight increase will double (dimer) or triple (trimer) and so on for higher orders depending on the number of aggregated antibodies. The larger antibody aggregate will pass through the SE-HPLC column quickly and not be evident at the same retention time as a single antibody (monomer). The specificity of the sample separation allows for a comparison of recoverable antibody amounts under differing conditions.

SE-HPLC is a sensitive, highly reproducible method to quantify protein and antibody concentrations. This method has a wide linear dynamic range and can be used for antibody quantification in the 17 ng/ml to 144,000 ng/ml range without sample dilution. There may be day to day variations in the derived area generated from a particular sample. However, under the same test conditions; by running comparator samples side by side, SE-HPLC column, temperature, mobile phase composition and other parameters used for analysis, different antibody composition carrier matrices can be evaluated for drug/carrier matrix effects by comparison of the area slopes generated by the individual carrier matrix. Evaluation of antibody carrier matrix effects over a wide dynamic range can be performed with SE-HPLC. Functionality of the antibody can be performed using ELISA as the antibody must be functioning if it has the ability to bind to the target antigen receptor. Functionality of antibody compositions by SE-HPLC can be inferred if the two analytical methods show a close correlation.

Validation Between ELISA and HPLC:

ELISA provides a method that indicates functionality of a subject antibody which is used to determine drug concentration. The antibody or subject drug must be functional to initiate binding in the assay. SE-HPLC provides a quantification of a particular molecular size of a compound but does not indicate functionality; only the quantity of a particular molecular weight entity in a solution. Samples of the same subject drug/carrier matrix were evaluated by splitting the same sample and simultaneously analyzing the samples by ELISA and SE-HPLC and comparing the derived concentration for the concentration gradient slope. Validation and agreement were performed by Pearson product-moment correlation wherein a linear correlation between matched data sets derived from the two analytical methods can be evaluated. The closer the derived Pearson correlation factor is to 1.0 the closer the correlation. Statistical significance wherein p≤0.05 between the data set values demonstrates that the Pearson correlation cannot be a random association and that the correlation is statistically significant.

ELISA/SE-HPLC Correlation of Analytical Method Results:

Subject antibodies AVASTIN® (bevacizumab) 25 mg/ml and LUCENTIS® (ranibizumab) 10 mg/ml were obtained from Genentech, South San Francisco Calif. EYLEA® (aflibercept) 48.2 mg/ml was obtained from Regeneron, Tarrytown N.Y. (note: bulk aflibercept as provided by Regeneron is at 48.2 mg/ml while the common pharmaceutical preparation is formulated at 40.0 mg/ml) Rhodamine antibody 11H10, (cat #GTX29093) was obtained from GeneTex Inc. Irvine, Calif.

ELISA analytical kits for bevacizumab (kit #AVA-E-U51) and Ranibizumab (kit #LUC-E-U52) were obtained from United Immunoassay Inc., San Bruno, Calif. USA. Aflibercept was analyzed using an ELISA materials, methods and procedure as described in Celik et al., Intraocular Pharmacokinetics of Aflibercept and Vascular Endothelial Growth Factor-A. *Invest Ophthalmol Vis Sci* 56 (2015) 5574-5578.

Sample Analysis by Enzyme-linked immunosorbent assay (ELISA): Bevacizumab and Ranibizumab ELISA assays were performed as per manufacturer's instructions except for a substitution of the base analytical standard material which was taken from the pharmaceutical preparations obtained and diluted as described herein below. Aflibercept ELISA was performed as described by Celik et al. except for a substitution of the base analytical standard material which was taken from the pharmaceutical preparations obtained and diluted as described below. The ELISA method dynamic ranges are as follows: bevacizumab 1-281.25 ng/ml, ranibizumab 1-100 ng/ml and aflibercept 1-100 ng/ml.

Size-Exclusion High Performance Liquid Chromatography (SE-HPLC). Analytical size-exclusion chromatography was performed using an Agilent HPLC system HP1100 from Agilent Technologies (Santa Clara, Calif.) with a UV detector. Studies were performed using a TSKgel UltraSW Aggregate 7.8 mm×30 cm, 3 μm SEC column with TSKgel UltraSW guard column (Tosoh Bioscience LLC, King of Prussia, Pa.). Mobile phase comprising 85% of 100 mM sodium sulfate in 100 mM phosphate buffer in HPLC water (adjusted to pH 6.68) with 15% acetonitrile/0.1% trifluoroacetic acid was used at a flow rate of 0.6 ml/min. Sample injections were 100 μl in volume. The eluted protein was monitored by UV Absorbance at 212 nm. Silanized HPLC sample vials and silanized vial inserts from Agilent Technologies (Santa Clara, Calif.), were used throughout. Antibody standard serial dilutions from the pharmaceutical preparations were made in a range from 144,000 ng/ml to 1.0985 ng/ml in 1:1 steps using a diluent comprising 7.5% α,α trehalose dihydrate, 100 mM sodium phosphate, 10 mM L-arginine, 0.3% sodium chloride, 0.04% polysorbate 80 with the balance being ultrapure water (Milli-Q, EMD Millipore USA) at a pH of 6.78 herein also known as "Formula 14" and also as Formula 14 pH 6.78, Formula 14 pH 7.0, Formula 14 pH 7.4 and Formula 14 pH 7.8. Additional dilutions for bevacizumab at 40.96, 64, 80, 100 and 200 ng/ml were made from the serial dilution steps. Additional dilutions of 100 ng/ml of ranibizumab and aflibercept at 100 ng/ml were made from the serial dilutions steps. Additional dilutions were made to accommodate the narrow dynamic range of ELISA kits and to generate more standard curve data points for the respective ELISA methods. Dilution standards were divided into two parts for ELISA and SE-HPLC analysis.

For bevacizumab, standard dilutions of 35.156, 40.96, 70.31, 80, 100, 140.62 and 281.25 ng/ml were analyzed by ELISA and SE-HPLC. Regression analysis of the resulting ELISA optical densities and SE-HPLC area generated standard curve formulas. The results of ELISA and SE-HPLC derived values were plotted against each other as shown in FIG. 1A. Pearson correlation analysis was run on the paired values demonstrating that the ELISA and SE-HPLC derived values are closely and significantly correlated.

Figure 1B:
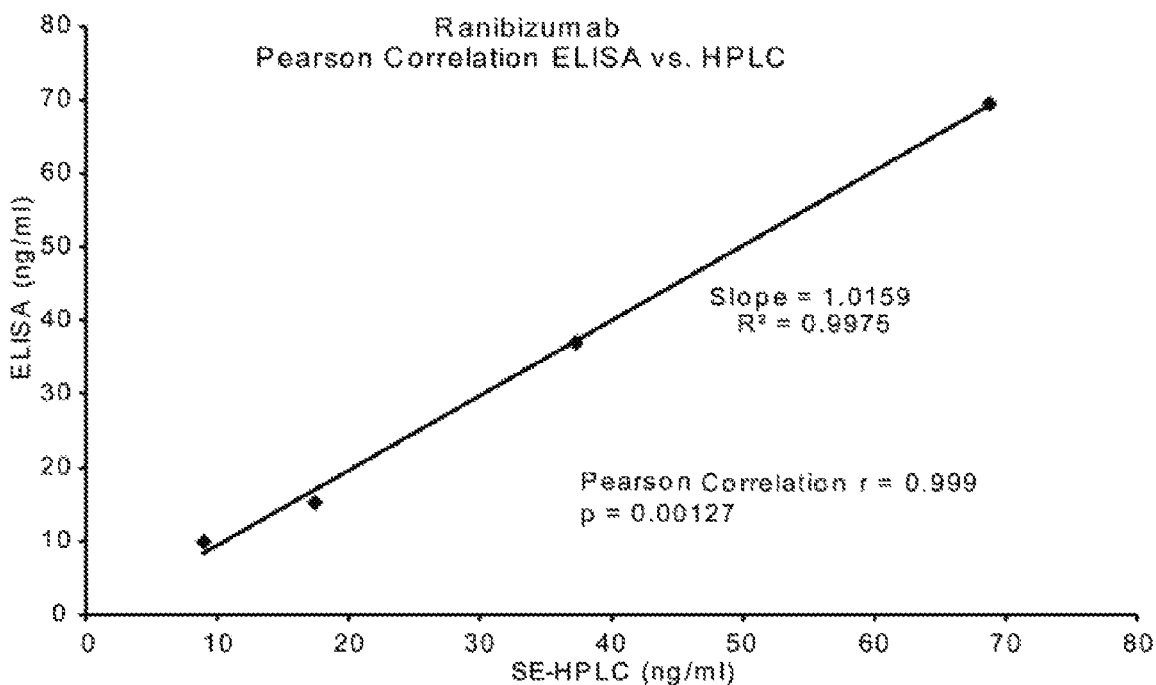

For ranibizumab, standard dilutions of 8.789, 17.578, 35.156 and 70.31 ng/ml were analyzed by ELISA an SE-HPLC. Regression analysis of the resulting ELISA optical densities and HPLC area generated standard curve formulas. The results of ELISA and HPLC derived values were plotted against each other as shown in FIG. 1B. Pearson correlation analysis was run on the paired values demonstrating that the ELISA and HPLC derived values are closely and significantly correlated.

Figure 1C:
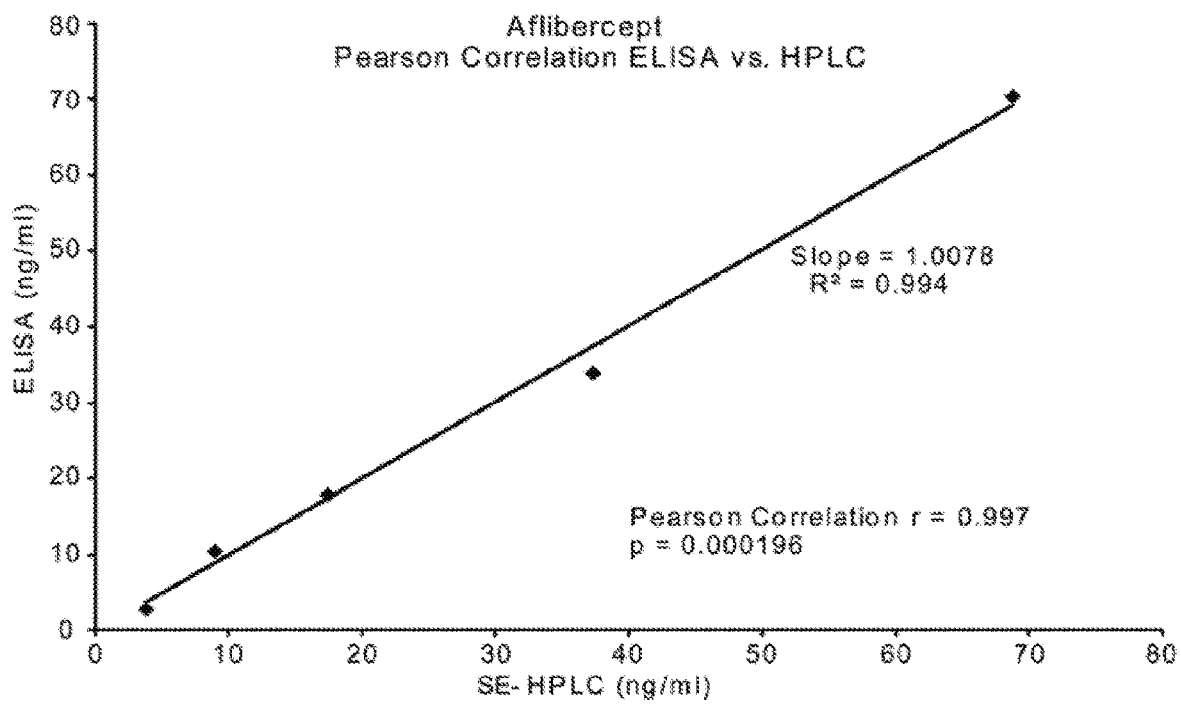

For aflibercept, standard dilutions of 4.3945, 8.789, 17.578, 35.156 and 70.31 ng/ml were analyzed by ELISA an SE-HPLC. Regression analysis of the resulting ELISA optical densities and HPLC area generated standard curve formulas. The results of ELISA and HPLC derived values were plotted against each other as shown in FIG. 1C. Pearson correlation analysis was run on the paired values demonstrating that the ELISA and HPLC derived values are closely and significantly correlated. Close and significant correlation between ELISA and SE-HPLC analytical methods validate SE-HPLC as a method to evaluate different formulation compositions over the wide dynamic range of the SE-HPLC method.

Comparison of Slope Values to Indicate Differences in Carrier Matrix Composition Effects.

The derived slope value of a known concentration serial dilution sequence provides a mathematical function that can be interpolated to determine an unknown sample concentration. This is the basis of most analytical chemistry quantification. Derived ELISA optical density and derived SE-HPLC area under the curve are examples of values that can be used to make a standard dilution curve and provide a mathematical function to predict concentration in an unknown sample. The slope value is an indication of the sensitivity of the method. For example, a slope value of 0.5 demonstrates a higher sensitivity than a slope of value 0.005. If all analytical test conditions remain constant for a given subject compound except for a difference in the carrier matrix that the compound is formulated, then a comparison of the slopes of two different carrier matrix formulation can be evaluated to determine if there is a difference in the formulation matrix. See Drljača et al. Comparison of Four Extraction Methods for the Determination of Veterinary Pharmaceuticals in Sediment. *Chromatographia* 79(3) (2016) 209-223. Based on the plotted serial dilution curves, drug carrier matrix effects can be expressed as a comparison of the dilution curve slopes. If the slope of one carrier matrix is less than a comparator, then the carrier matrix with the lower slope value expresses carrier matrix suppression.

Figure 2:
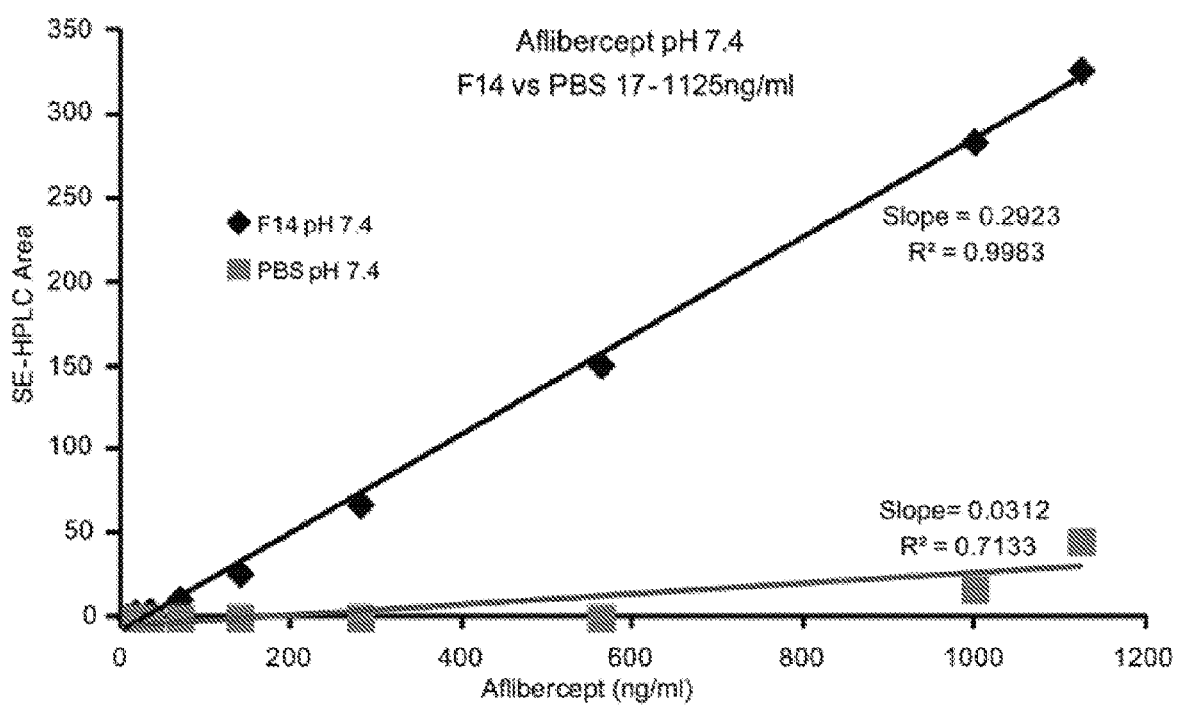
FIG. 2 provides a graphical plot of SE-HPLC area determinations for aflibercept diluted with formula 14 at a pH of 7.4 vs. dilutions with PBS at a pH of 7.4 from 17.578 ng/ml to 1125 ng/ml.

SE-HPLC can be used to evaluate antibody drug matrix effects to determine carrier matrix formulations that have better anti-aggregation potential. For example, aflibercept was diluted from the manufacturer's composition of 48.2 mg/ml to 144,000 ng/ml then further serially diluted from 144,000 ng/ml to 17.578 ng/ml in 1:1 steps with either Formula 14, pH 7.4 (as described below) or with PBS (pH 7.4). The serial dilution samples from above were analyzed side by side with SE-HPLC as described. SE-HPLC area values for dilutions from 17.578 to 1,125 ng/ml for both compositions were plotted against the dilution values. Slopes of the areas were determined for both compositions for comparison. FIG. 2 shows the plots of the two compositions. This comparison shows that the slope values are significantly different (paired t test p=0.0473). The Formula 14 slope of 0.2923 is greater than the PBS slope of 0.0312.

Figure 3A:
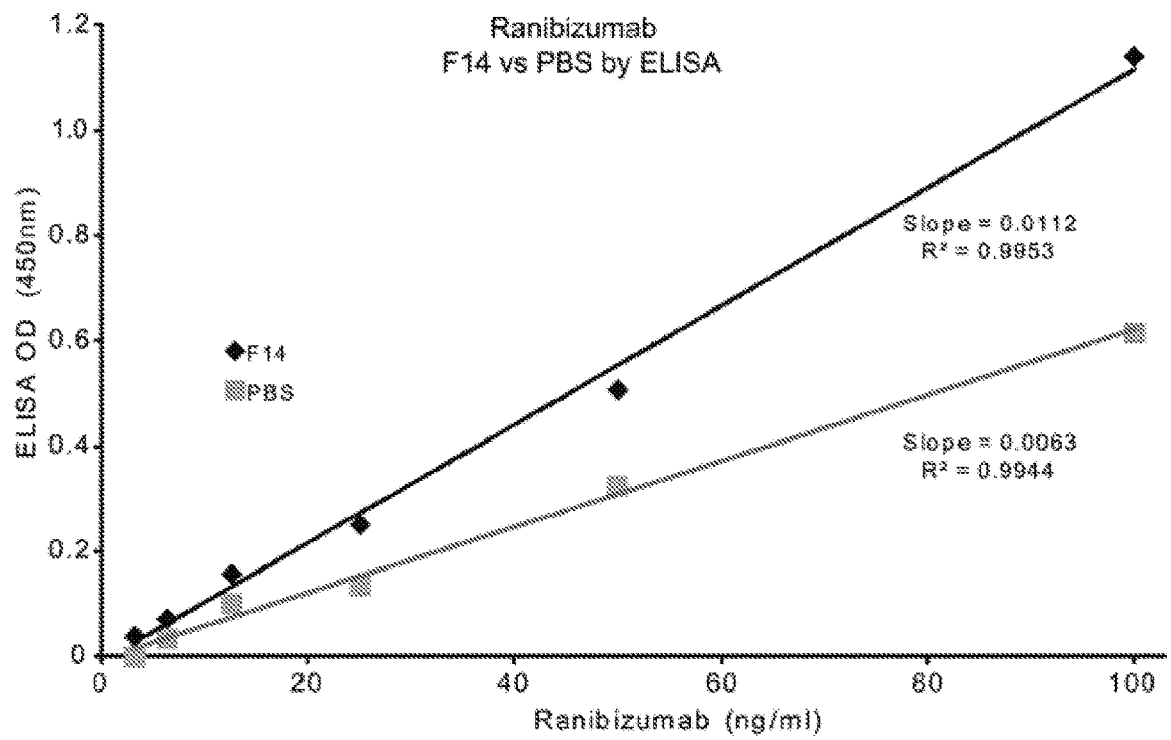
FIGS. 3A and 3B provide a comparison of the two analytical methods ELISA (FIG. 3A) and SE-HPLC (FIG. 3B) for ranibizumab diluted with Formula 14 and PBS.
Figure 3B:
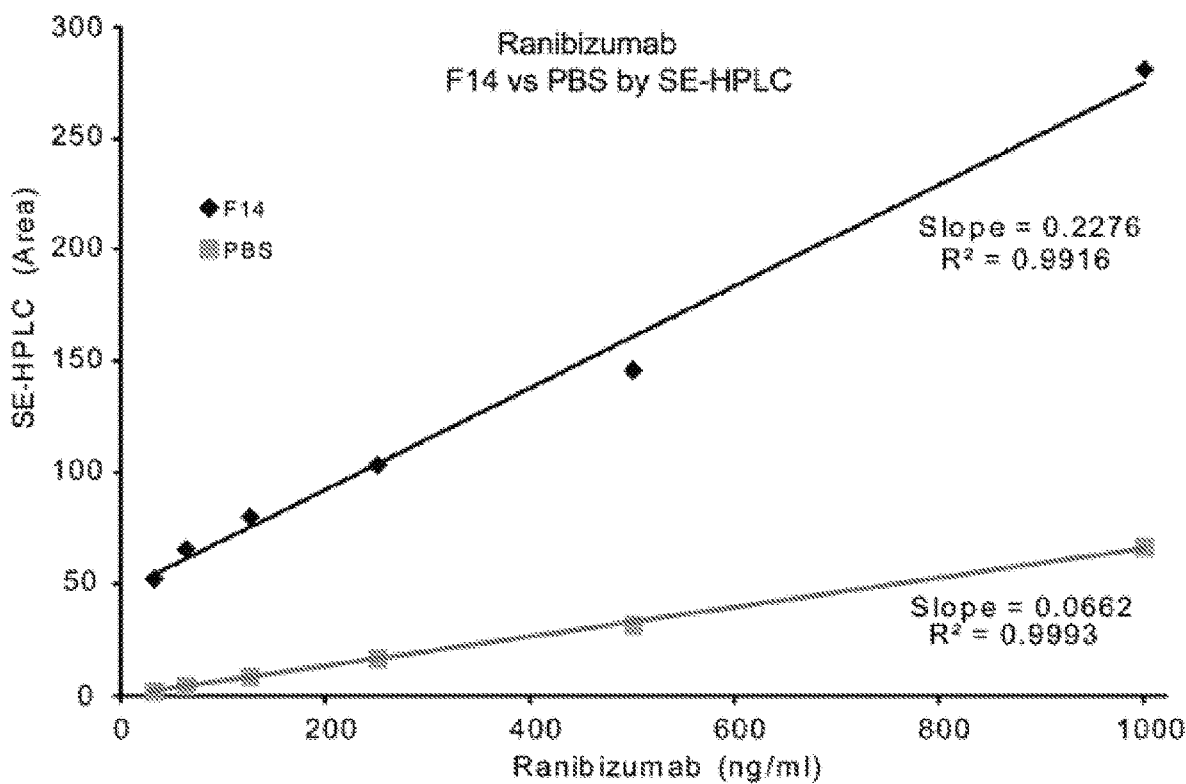

Single Area peak values derived from SE-HPLC, as used herein, report essentially the monomeric antibody concentration, as the higher order of aggregates formed would pass through the size exclusion column and elute at different time points and not be enumerated. In contrast in immunoassays, aggregated antibodies may still have a substrate binding potential depending on the exact location of the antibody to antibody aggregation point. So long as an antigen binding site is unobscured, antigen binding may occur in aggregated situations however at a reduced amount relative to the total number of antibodies in the carrier matrix. ELISA methods measure the number of antigen/antibody binding occurrences. As SE-HPLC single peak area determinations excludes aggregated antibody forms, ELISA optical density determination will include some binding from otherwise aggregated antibodies. In this sense, the comparative slope value ratio of two analytical methods for the same solution may give different slope ratios for SE-HPLC versus ELISA as both methods measure monomeric antibody concentrations while ELISA may additionally report the influence of aggregated antibodies. For example, using ranibizumab as a model drug, FIG. 3A shows the ratio of ELISA slopes of formula 14 versus PBS diluent slope of 1.77 (0.0112/0.0063) whereas FIG. 3B shows the SE-HPLC slope ratio is 3.43 (0.2276/0.0662). The difference in the slope ratios of the two testing methods for the same antibody carrier matrices may be due to the SE-HPLC method measuring only monomer antibodies while the ELISA method may include antigen/antibody with monomers in addition to other aggregated antibody forms.

Frequently, antibody containing biological fluid samples are diluted with phosphate buffered saline (PBS) to bring the antibody concentration into the linear range of an ELISA method. In this case PBS dilution may result in up to 50% loss of the biopharmaceutical agent. Because dilution with PBS increases aggregation, reported drug concentrations in biological samples may be significantly lower than actual drug concentrations in various in vitro and in vivo immunoassay studies.

The exemplary formulations provided herein were found to prevent antibody aggregation, particularly at low antibody concentrations. By reducing aggregation, the formulations provide increased amounts of biologically active antibody when administered to a subject.

Biopharmaceutical Agents:

The active agents to be incorporated in the described pharmaceutical formulations are proteinaceous molecules including monoclonal antibodies, polyclonal antibodies, antibody-related products (e.g., antibody-drug conjugates), as well as therapeutic peptides and proteins (e.g., fusion proteins), and other biopharmaceuticals that are proteinaceous in nature including vaccines, proteinaceous toxins (including botulinum toxins), allergenic products (including allergen extracts and antigen skin test materials), and certain hormones (including amine, peptide and protein hormones).

In some embodiments provided herein, the active agent is a monoclonal antibody or fragment thereof. In certain embodiments, the active agent is an anti-VEGF biologic. In one embodiment, the active agent is bevacizumab. Bevacizumab is sold by Roche under the trade name AVASTIN®. Bevacizumab is a full-length IgG1$_\kappa$ humanized mouse monoclonal antibody (mab) against Vascular Endothelial Growth Factor A (VEGF-A) that is produced in Chinese Hamster Ovary (CHO) cells and is glycosylated.

In another embodiment the active agent is ranibizumab marketed by Genentech under the trade name LUCENTIS®. Ranibizumab is a monoclonal antibody fragment (Fab) created from the same parent mouse antibody as bevacizumab. It is produced in *E. coli* and is not glycosylated.

In another embodiment, the active agent is a fusion protein, such as for example the anti-VEGF fusion protein aflibercept (marketed under the tradename EYLEA®), which is a recombinant fusion protein consisting of vascular endothelial growth factor (VEGF)-binding portions from the extracellular domains of human VEGF receptors 1 and 2 that are fused to the Fc portion of a human IgG1 immunoglobulin.

In another embodiment, the active agent is a peptide or protein, including, but not limited to: hormones such as insulin and growth-stimulating hormone, blood factors, erythropoietin, tissue plasminogen activator, interferons, interleukins, and vaccine antigens.

The biopharmaceutical agent can be present in any concentration, e.g., 1 ng/ml to 250 mg/ml. In one embodiment, the biopharmaceutical agent is present at about 1 mg/ml to about 125 mg/ml, about 10 mg/ml to about 150 mg/ml, and about 1 mg/ml to about 25 mg/ml. In another embodiment, the biopharmaceutical agent is present in an amount of less than 3 mg/ml, 1 mg/ml, and less than 0.01 mg/ml. The formulations and methods of the present invention are particularly advantageous for biopharmaceutical agents that are prone to aggregation and/or deamidation.

The selected concentration of antibody within the matrices of 2.5 mg/ml was done out of convenience and continuity with other examples disclosed herein and is not meant to be a limiting factor for the invention. Different antibodies are manufactured and packaged at variable concentrations depending on the intended use and intended dilution for and prior to administration. In the preferred embodiment, antibody concentrations in drug carrier matrices would be about 0.5-150 mg/ml and preferably 1-50 mg/ml or more preferably 1-25 mg/ml.

Hydrophobicity Interactions Affect Antibody Aggregation:

Immunoglobulin domains are compact globules with many reaction sites that are responsible for contacts with numerous ligands. See e.g. Nezlin R and Ghetie V. Interactions of immunoglobulins outside the antigen-combining site. *Adv Immunol.* 82 (2004) 155-215. There are many properties of biologics that affect protein aggregation, including hydrophobicity, charge, propensity to form β-sheets, and propensity to form α-helical structures. Hydrophobic interactions play a significant role in protein-protein interactions and are thought to have major importance during protein aggregation. See e.g. Lauer T M, et al. Developability index: a rapid in silico tool for the screening of antibody aggregation propensity. *J Pharm Sci.* 101(1) (2012) 102-115).

Attempts have been made to identify sites responsible for IgG self-association using atomistic molecular simulations and certain studies identified several aggregation-prone motifs. See Chennamsetty N, et al. Aggregation-prone motifs in human immunoglobulin G. *J Mol Biol.* 391(2) (2009) 404-13. The molecular simulation technique has been expanded to include a Developability Index (DI) (see US 2011/0257104 and US 2015/0205912). Chennamsetty identified fourteen aggregation prone motifs. More aggregation-prone motifs were found in the Fc region than in the Fab region. Most of these domains were found arranged near or in the hinge region and were predominantly distributed in the loop regions but rarely within β-sheet regions. The size of the motifs was found to vary between one and seven amino acid residues and some of the motifs were found to be dependent from the tertiary protein structure. All four IgG subclasses were found to share common motifs which however differed from those of other Ig classes (IgA1, IgD, IgE, and IgM). Another method, termed the spatial aggregation propensity (SAP), identifies aggregation prone regions based on the dynamic exposure of spatially-adjacent hydrophobic amino acids. See Voynov, V. et al. Predictive Toole for Stabilization of Therapeutic Proteins. *Mabs* 1(6) (2009) 580-582.

The DI/SAP method and an additional method, the Oligomer Detection Assay (ODA) (Obrezanova O, et al. Aggregation risk prediction for antibodies and its application to biotherapeutic development. *MAbs* 7(2) (2015) 352-63) are being developed in order to find hydrophobic motifs and re-engineer the protein amino acid sequence to be less hydrophobic and/or find antibody variants that contain less hydrophobic amino acid sequences. See Lee C C, et al. Toward aggregation-resistant antibodies by design. *Trends Biotechnol.* 31(11) (2013) 612-20. This effort is expensive, laborious and time consuming. In contrast, the present formulations permit use of monoclonal antibody or antibody products in a stable state without extensive molecular manipulation to avoid aggregation.

In addition to aggregation prone domains known to occur in monoclonal antibodies, both full length and Fab portions, aggregation domains are also found in antibody fusion molecules, such as, for example, the anti-VEGF fusion protein aflibercept, which is a fusion of the VEGF-binding portions from the extracellular domains of human VEGF receptors 1 and 2 to the Fc portion of a human IgG1 immunoglobulin as well as etanercept, which is a fusion of the TNF receptor to the Fc portion of a human IgG1 immunoglobulin. Bevacizumab (AVASTIN®) contains 4 aggregation prone domains in its light chains. Ranibizumab (LUCENTIS®), having the identical light chain, shares the same 4 aggregation prone domains in its light chains. Bevacizumab also contains another three aggregation prone domains in its heavy chains past the hinge (amino acid sequences SVFLFP, VVSVLTVL, and GSFFL). The sequences are also found in the fusion protein aflibercept due to it including the Fc portion of a human IgG1 immunoglobulin. Aggregation prone domains are known to occur in other biopharmaceuticals including albumin, somatotropin, insulin, Factor VIII, Epoetin alfa (recombinant human erythropoietin, marked as EPOGEN or PROCRIT), and glucagon. See Wang, X., et. al. Potential Aggregation prone Regions in Biotherapeutics. *MAbs* 1:3 (2009) 254-267.

Without being bound by theory, the present formulations have been shown to reduce aggregation (and thus, deactivation) of aggregation-prone biopharmaceutical agents primarily by blocking hydrophobic areas on the drug surface. Similarly, the present formulations are applicable to the coating of vehicles (e.g., glass vial, IV bag or tubing) for storage, transport, experimental assay, or delivery of the agents to reduce adsorption at the liquid-solid interface by blocking hydrophobic regions on the vehicle from interacting with the active agents. The formulations thus enhance initial and long-term stability, under room temperature conditions (e.g., 15° C. to 30° C.), actual and simulated biological conditions (e.g., at 37° C.), and at elevated temperatures (greater than 40° C.). The formulations also maintain agent stability under both static and stirred/agitated conditions. In one embodiment, the formulation comprising the biopharmaceutical agent is stable for storage at about 40° C. for at least 7 days. As used herein, the characteristic of "storage stable" means the composition is stable for at least or about 14 days at 23° C. or stable for at least or about 90 days at 4° C. In another embodiment, the formulation comprising the biopharmaceutical agent is stable for storage at about 40° C. for at least 28 days. As used herein the characteristic of "storage stable" means less than 5% degradation compared to the starting monomer concentration. As used herein the characteristic of "storage stable" means less than 10% loss or reduction in concentration from the starting concentration.

Formulation for Improving Aggregation Profiles:

The formulations described herein can be formulated for in vitro or in vivo applications. In one embodiment, the formulation is pharmaceutical formulation intended to deliver the active agent to a subject in need thereof. In one embodiment, a formulation is provided comprising trehalose, arginine and polysorbate 80 (TWEEN® 80) at a pH between 6.8-7.8, in which the ingredients act synergistically in combination to counteract aggregation and improve stability of a biopharmaceutical agent.

The pharmaceutical formulation can be prepared for various routes of administration including, but not limited to: enteral, parenteral (e.g., intravenous, intramuscular, subcutaneous, filled syringe), pulmonary (nebulized solution), ophthalmic injection (e.g., intravitreal injection), topical, dermal, intradermal, transdermal, or topical ophthalmic (e.g., liquid or viscous eye drop, eye ointment, semi-solid gel patch, trans-scleral, with or without photokinetic drug delivery). In one embodiment, the pharmaceutical formulation is a topical ocular formulation for trans-scleral delivery of the active agent. In one embodiment a stabilizing formulation is provided that includes trehalose, arginine, TWEEN® 80 and NaCl in a buffered solution at a pH range of 6.7 to 7.8. In certain embodiments, a formulation is provided that not only prevents aggregation of biopharmaceuticals in dilute solution but is also able to disaggregate already aggregated solutions. One such formulation (referred to herein in experimental studies as Formula 14, contains 0.3% NaCl, 7.5% trehalose, 10 mM arginine, and 0.04% polysorbate 80, 100 mM sodium phosphate buffer in water at a pH of 6.78.

Topical ocular formulation embodiments disclosed herein are particularly advantageous for use in combination with infrared irradiation to achieve photokinetic drug delivery. Using one exemplary formulation, various active agents (including bevacizumab, ranibizumab, and aflibercept,) are stable even when irradiated with 24.5 mW IR (950 nm) light for 5 hours.

In addition to carrier matrix effects, SE-HPLC can be used to determine if storage or environmental exposure conditions affect the antibody. For example it is well know that ultraviolet light may degrade an antibody, however we were interested in finding if non-thermal, non-ionizing infrared light had any detrimental effects on antibodies. In this case a volume of 25 mg/ml bevacizumab was diluted with Formula 14 to a concentration of 500 ng/ml. This material was used as a starting composition and separated into two groups control and light exposure, n=4/group. Plastic chambers (3 ml) were fitted with tight lids housing 5 mm 950 nm IR LEDs with light directed toward the bottom of the chambers. Each chamber received 600 µl of the 500 ng/ml bevacizumab in Formula 14. LEDs were positioned 1 cm away from the surface of the antibody solution. The chambers were placed in a 37° C. water bath. In the light control group, the LED was turned ON providing 24.5±2.5 mW power, fluency of 3.15±0.15 W/cm$^2$ pulsed at 1000 cycles per second (Hz) with a duty cycle of 20% (20% ON time) measured at the LED surface. At 1 cm distance from the LED to the surface of the solution, the power was 12 mW±1.0 mW and a fluency of 1.25 W±0.25. The non-light control group was shielded from light exposure. Samples were taken at 1 hour and 5 hours and examined by ELISA and SE-HPLC.

Figure 4:
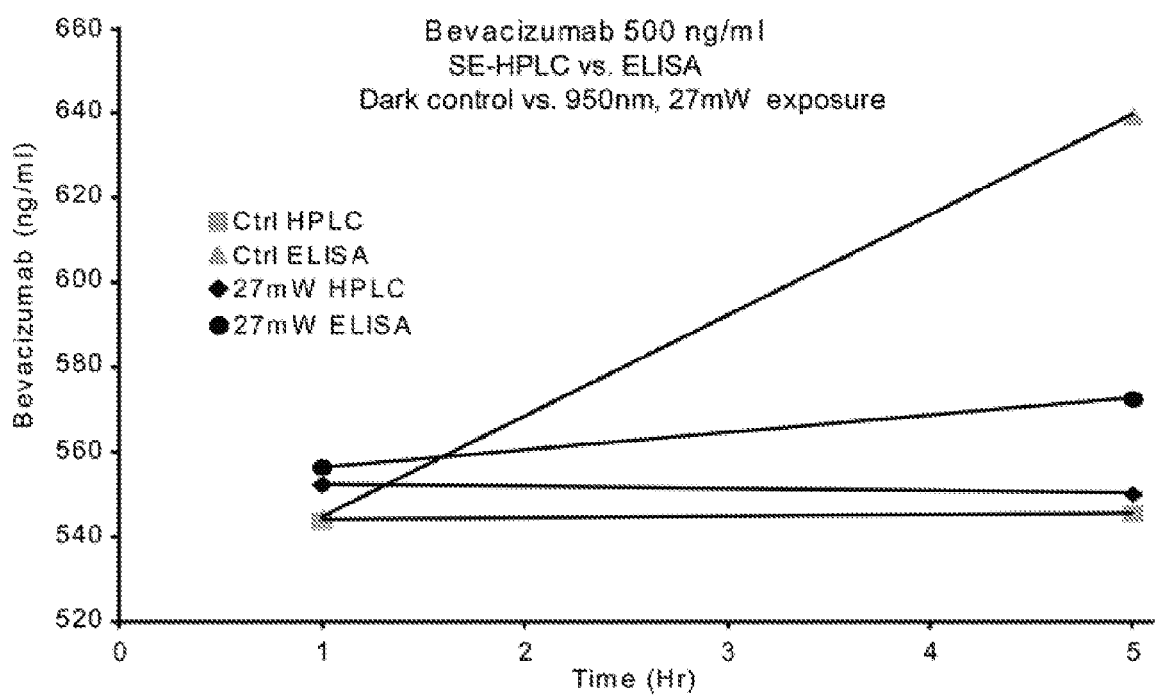
FIG. 4 shows a graphical comparison of analytical methods for bevacizumab exposed to 950 nm IR light from 1 to 5 hours.

Control and light exposed ELISA samples were diluted by 3.5714 times to bring into the ELISA method range of 1-225 ng/ml. Samples for SE-HPLC were not diluted. A standard dilution range of 562.5 to 4.3945 ng/ml starting with 25 mg/ml bevacizumab in formula 14 was made and divided for both analytical methods. ELISA samples were run on the same plate at the same time. SE-HPLC samples were run consecutively on the same method setup. Standard dilution curves were derived and used to determine the concentration of the subject test samples. FIG. 4 shows the result of IR light exposure using both ELISA and SE-HPLC methods. As shown in both the control and light exposed groups using SE-HPLC the concentration was about 550 ng/ml at 1 and 5 hours. In the ELISA analytical group, the one hour control and light exposed group were also about 550 ng/ml. At 5 hours both the control and the light exposed showed an increase in concentration however this increase may be attributed to the inherent error in ELISA methodology and/or dilution errors. In any event, it appears that exposure to relatively high amounts of non-thermal IR light does not have a detrimental effect on bevacizumab diluted with formula 14.

Degassing:

For in vitro methods, the present inventors have found degassing to be a surprisingly useful step. To perform drug diffusion experiments, the permeation cell drug receiver solution should be degassed to prevent permeation restrictive bubble formation under the tissue surface. Without being bound by theory, it is believed that degassing removes dissolved air that would otherwise adhere to hydrophobic areas, which in turn cause nanobubble bridge aggregation between agent molecules.

In Franz cell permeation studies described earlier, typically, the receiver solution is de-gassed in part to prevent bubbles from forming in the receiver chamber. If the solution were not degassed, the 37° C. heating and the stirring by magnetic stir bar would allow bubbles to form under the study tissue surface and cause decreased drug transport through the tissue and into the receiver media.

Antibodies and other proteins subjected to heating undergo conformational changes that can lead to the formation of aggregates. Stirring can create shear or interfacial effects in which the protein adsorbs to the air-water interface, leading to structural alterations that can initiate aggregation as well. See Telikepalli S N, et al. Structural Characterization of IgG1 mAb Aggregates and Particles Generated under Various Stress Conditions. *J Pharm Sci* 103(3) (2014) 796-809. Dissolved air can manifest as nanobubbles, having diameters 40-300 nm, which can act as a bubble bridge between the hydrophobic areas of proteins, thereby creating aggregates.

The present inventors investigated the effects of degassing on bevacizumab or ranibizumab solutions, and confirmed that degassing formulation solutions significantly improved the stability of these agents. When Formula 14 was degassed and tested against non-degassed Formula 14 and PBS, the degassed formula was 5% higher in recovery than non-degassed formula and 44% higher in recovery than the PBS solution. When the same degassing/not degassed experiment using ranibizumab was performed, a greater positive difference was observed in the degassed ranibizumab group compared to bevacizumab. This greater effect of de-gassing may be due to the structural difference of ranibizumab, which is a fragment of bevacizumab. The surface hydrophobic to hydrophilic area ratio provides more exposed hydrophobic area and thus more area prone to aggregation when compared to the full structure of the parent mAb bevacizumab. Again without be bound by theory, the degassed solution removes the majority of dissolved gas in the solution thereby reducing the surface nanobubble area potential and thus allows the surfactant to coat the hydrophobic areas of the mAb molecules. The removal of dissolved gasses and the hydrophobic area coating by the surfactant allows the mAb to move freely within the solution without aggregating from bubble to bubble contact or absorb surface nanobubbles from the solution.

Accordingly, in one embodiment, the invention provides degassed excipient solutions for dilution and storage of biopharmaceuticals. In another embodiment, an in vitro method of quantifying the concentration or permeation of an agent is provided including a step of degassing the agent solution, wherein the agent is dissolved in a formulation disclosed herein. Degassing can be performed by any means known in the art including but not limited to vacuum, helium sparge, ultrasound, or membrane degasification.

Methods of Manufacture, Use, and Treatment:

The formulations disclosed herein can be used in various steps in the manufacture, storage, transport, and delivery of biopharmaceuticals, and in in vivo and in vitro methods to prevent, reduce, or reverse aggregation of the biopharmaceutical. Additionally, the formulations may be used as reagents in analytical immunoassays including ELISA assays.

In one embodiment, the formulations of the present invention are used as the solvent for a biopharmaceutical agent not subjected to prior lyophilization. As another example, the present formulations can be used as the media for lyophilization. When the novel formulations disclosed herein are used as the media for lyophilization, the lyophilized formulation can be reconstituted in phosphate buffered saline (PBS) without undue aggregation due to the protection from aggregation provided by the formulations.

In another embodiment, the formulations of the present invention are used to disaggregate previously aggregated agents. This reversal of aggregation can be used to "rescue" an agent that has aggregated during manufacture, dilution, or reconstitution.

In another embodiment, the formulations of the present invention are used as pre-treatment media to protect an agent from aggregating upon dilution.

In another embodiment, the formulation is a pharmaceutical formulation to deliver the active agent to the subject. The pharmaceutical formulation can be administered by to the subject by various routes described above. In one embodiment, the pharmaceutical formulation is administered to a subject to treat age-related macular degeneration.

In another embodiment, the pharmaceutical formulation is administered to a subject topically for example applied to the ocular surface to treat corneal neovascularization or applied to the skin surface to treat psoriasis or atopic dermatitis.

In another embodiment, the formulation is a pharmaceutical formulation to deliver the active agent to the subject.

The pharmaceutical formulation can be administered by to the subject by inhalation as a nebulized solution. In one embodiment, the pharmaceutical formulation is administered to a subject to treat lung cancer or other pulmonary diseases.

In still another embodiment, the formulations of the present invention are used as reagent media to protect an agent from aggregating upon dilution in analytical immunoassays including ELISA assays.

For some methods, the formulations are preferably sterile.

Optional Excipients:

Certain of the formulations and methods described herein can be used to deliver a topical ocular formulation (e.g., eye drop, ophthalmic ointment, etc.), which may be used in combination with a light source to provide photokinetic drug delivery, see U.S. Pat. No. 8,948,863. Additional optional excipients may include thickening agents and antioxidants.

Certain of the formulations and methods described herein can also be used to deliver an inhalable pulmonary formulation (e.g., nebulized solution, etc.), see U.S. Pat. No. 8,776,786. Additional optional excipients may include antioxidants and surfactant agents such as Pluronic F127. Pluronic F127 is a difunctional block copolymer surfactant terminating in primary hydroxyl groups.

Thickening Agents:

The bioavailability of traditional ocular drug delivery systems such as eye drops is very poor because the eye is protected by a series of complex defense mechanisms that make it difficult to achieve an effective drug concentration within the target area of the eye. The anatomy and physiology of the eye is one of the most complex and unique systems in the human body. Lachrymation, effective drainage by the nasolacrimal system, the inner and outer blood-retinal barrier, the impermeability of the cornea, and inability of other non-corneal structures to absorb compounds make the eye exceedingly impervious to foreign substances. While these innate barriers are advantageous for hindering the invasion of undesired molecules, pathogens, and particulates, they pose significant challenges to the delivery of ocular drugs. See Palani S, et al. Ocular drug delivery: a review. *Int J Pharm Sci Res.* 1(3) (2010) 1-11.

To increase the residence time of the formulation on the eye when topically applied, one or more thickening agents may be incorporated. By increasing the residence time, the thickening agents serve to control and/or extend the release time of the active agent. Thickening agents are specifically employed for formulations designed as semi-solid gel ocular patches and viscous eye drops or ointments. Several excipients such as carbopol gels, cellulose derivatives, dextran, gelatin, glycerin, polyethylene glycol, poloxamer 407, polysorbate 80, propylene glycol, polyvinyl alcohol, and polyvinyl pyrrolidone have either viscosity enhancing or bioadhesive properties that can significantly improve the ocular retention time. See Lallemand F, et al. Successfully improving ocular drug delivery using the cationic nanoemulsion, Novasorb. *J Drug Deliv.* 2012, ID604204, 16 pages. In one embodiment, the thickening agent is selected from one or more of carboxymethyl cellulose, polyvinyl alcohol, hydroxypropyl methylcellulose (a.k.a. HPMC or hypromellose), hydroxypropyl cellulose, polyacrylic acid and glycerin/propylene glycol.

An additional thickening agent that is biocompatible is hyaluronic acid. See Rah M J, A review of hyaluronan and its ophthalmic applications. *Optometry* 82(1) (2011) 38-43. In one embodiment, the thickening agent is hyaluronic acid.

Photokinetic drug delivery calls for a one hour treatment period. By incorporating a thickening agent, the formulation will be more viscous and more resistant to tear wash out; remaining on the eye for a period longer than thin, less viscous eye drops. This translates into a longer residence time, which allows the drug more time to permeate the cornea and sclera when irradiated with IR light.

Antioxidants:

IR light may cause Reactive Oxygen Species formation (ROS) depending on the wavelength and fluency. Free radicals are important compounds in the system of signal processing in mammalian organisms and in the action against viruses and bacteria. However, if the number of free radicals exceeds a critical threshold, they destroy cells and cell components and cause skin damage in different forms, including for example, premature skin aging and even skin cancer. See Darvin M E, et al. Radical production by infrared A irradiation in human tissue. *Skin Pharmacol Physiol.* 23(1) (2010) 40-46. To counteract ROS generated by IR light, ophthalmic formulas may be supplemented with antioxidants to counter ROS. These can come in the form of polyphenols including epigallocatechin 3-gallate, silymarin, resveratrol, glutathione, ubiquinone (also known as Coenzyme Q10, ubidecarenone, coenzyme Q) and the synthetic analog idebenone. Anti-oxidant vitamins include vitamin A, B vitamins including niacinamide, nicotinamide, vitamin C and its derivatives and several forms of vitamin E (tocoperols). Other anti-oxidants include flavins, proanthocyanidins, carotenoids (also known as tetraterpenoids: xanthophylls class, carotenes class) including β-carotene, α-carotene, β-cryptoxanthin, γ-carotene, lutiein, astaxanthin, zeaxanthin, lutein, lycopene etc. In one embodiment, the antioxidant is glutathione, ethylenediaminetetraacetic acid (EDTA), or sodium bisulfite or metabisulfite. In one embodiment, the antioxidant is glutathione.

The following examples are included for the sake of completeness of disclosure and to illustrate the methods of making the compositions and composites of the present invention as well as to present certain characteristics of the compositions. In no way are these examples intended to limit the scope or teaching of this disclosure.

Example 1

Formulation Strategy and Excipients

Disclosed herein are stabilizing formulations useful for the manufacture, storage, dilution, and delivery of biopharmaceutical agents. The formulations are particularly suitable for trans-scleral delivery of anti-VEGF antibody agents, such as, for example, bevacizumab ranibizumab and aflibercept.

Figure 5:
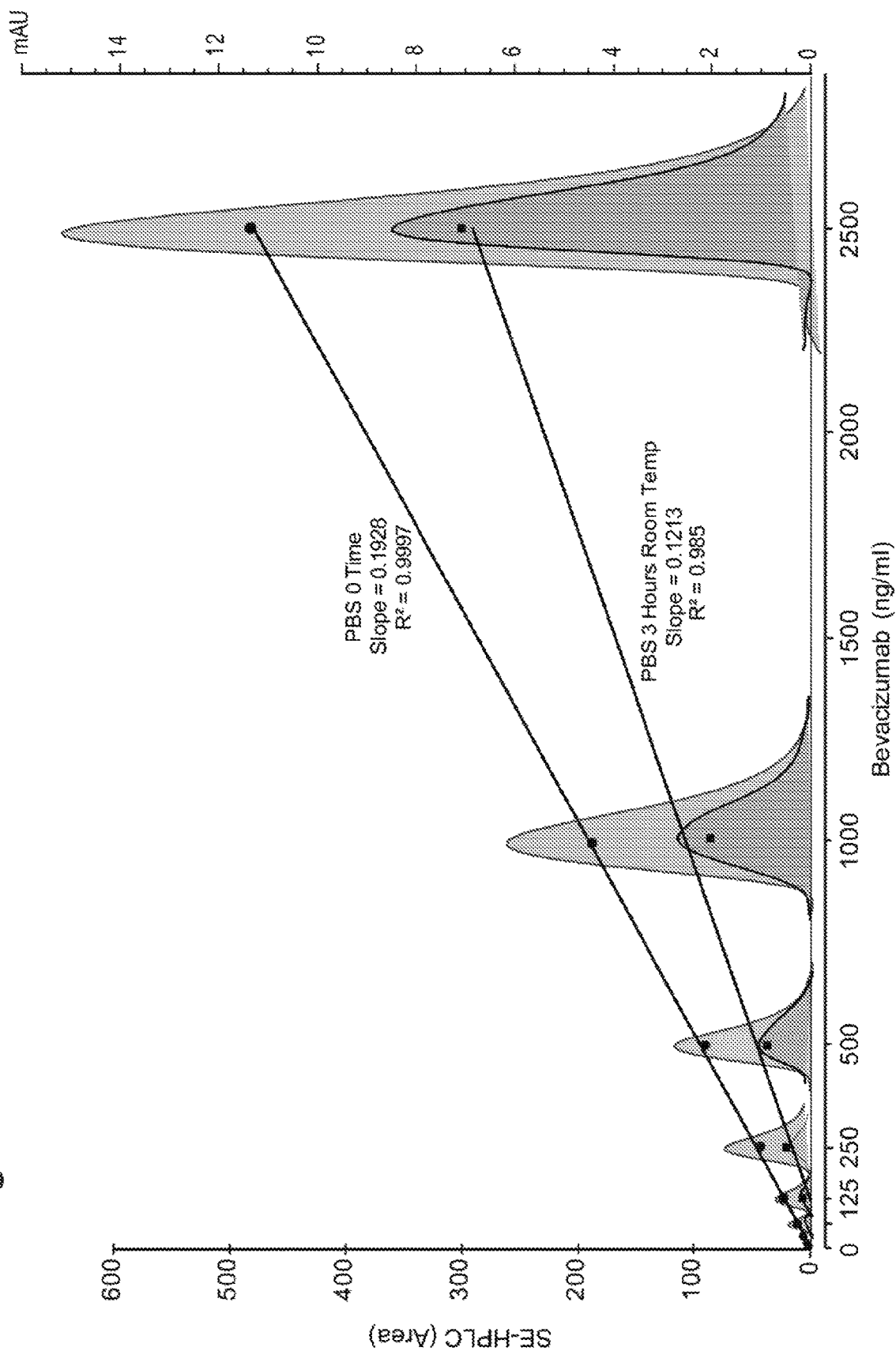
FIG. 5 shows a graphical representation SE-HPLC area for bevacizumab diluted with PBS at 0 time versus 3 hours at room temperature.

Bevacizumab, ranibizumab and aflibercept, as the primary anti-VEGF agents utilized by trans-scleral delivery, are very prone to aggregation and diminished function once removed from the manufacturer's vial and diluted. For example, as shown in FIG. 5, the present inventors found that monomeric bevacizumab significantly decreased when phosphate buffered saline (PBS) was used as the diluent. In the assay, serial dilutions of bevacizumab were prepared in PBS and assayed by SE-HPLC at 0 time vs the same samples analyzed 3 hours when kept at room temperature (23° C.), in order to check the amount of time it took for PBS to degrade the protein. The monomeric bevacizumab was found to decrease within the 3 hours, with the starting standards having a slope of 0.1928 and then 3 hours later having a slope of 0.1213; a loss of about 30%. Additionally, it was found that the manufacturer's formulations for ranibizumab, in regards to the storage and delivery of the agents, did not protect the drugs from aggregation under dilution and elevated temperatures encountered in in vitro and in vivo drug concentration determinations. It was also found that the manufacturer's formulation (formula 1) did not prevent aggregation at the very low concentrations. A discontinuity was noticed at 1,000 ng/ml-1,150 ng/ml concentrations (see FIG. 6).

In one embodiment, the experimental design for the formulations to be tested for improved stability started with the manufacturer's formulations for ranibizumab and bevicizumab tested against dilution in water and then phosphate buffered saline (PBS). Bevacizumab (AVASTIN®) and ranibizumab (LUCENTIS®) have different formulations from the manufacturer. Bevacizumab (AVASTIN®) is formulated from the manufacturer at a concentration of 25 mg/ml in a solution of 6% (60 mg/ml) α,α-trehalose dihydrate, 0.04% (0.4 mg/ml) polysorbate 20 (TWEEN® 20), 0.58% (5.8 mg/ml) sodium phosphate (monobasic, monohydrate), 0.12% (1.2 mg/ml) sodium phosphate (dibasic, anhydrous), in water at pH 6.2. Ranibizumab (LUCENTIS®) is formulated from the manufacturer at a concentration of 10 mg/ml in a solution of 10% (100 mg/ml) α,α-trehalose dihydrate, 0.01% (0.1 mg/ml) polysorbate 20 (TWEEN® 20), and 10 mM (1.98 mg/ml) L-histidine in water for injection at a pH 5.5.

In one embodiment, formulations shown in Table 1 were tested. Based upon the manufacturer's formulation, excipient substitutions were screened with dilutions of standard concentrations of ranibizumab. Water, PBS, saline (0.9% NaCl) and 0.3% NaCl solutions were used as the starting solution. Other than the manufacturer's formulation, sodium phosphate buffer was used in the formulations. Trehalose was used throughout the formulations, owing to its protein stabilizing quality. The amino acids arginine, glycine, histidine and glutamic acid were tested in various capacities. Surfactants were also tested. The manufacturer's formulation contained 0.01% TWEEN® 20. Concentrations of 0.01% and 0.04% of TWEEN® 20 were screened. Another surfactant, TWEEN® 80, was tested at a concentration of 0.04%.

Additionally, PLURONIC® F127 was tested. PLURONIC® is the BASF trade name for poloxamer 407, which is a hydrophilic non-ionic surfactant. Poloxamer 407 is a triblock copolymer consisting of a central hydrophobic block of polypropylene glycol (PPG) flanked by two hydrophilic blocks of polyethylene glycol (PEG). The approximate lengths of the two PEG blocks is 101 repeat units while the approximate length of the PPG block is 56 repeat units although these lengths are understood by those of skill in the art to be approximate. Poloxamer 407 has CAS Number 9003-11-6. As used herein the terms PLURONIC® F127 and poloxamer 407 refer to the same chemical entity and are used interchangeably. Finally, pH was looked at as a variable in the formulations. These were then analyzed by SE-HPLC as described above.

Of the above excipients, trehalose acts as a stabilizer and is preferably present in an amount of 5 to 10%, 7% to 10%, or about 7.5%. For avoidance of doubt the term "about" in the context of trehalose concentration means a deviation of equal to or less than 1% from the stated concentration.

Polysorbate 80 (TWEEN® 80) acts as a non-ionic surfactant and is preferably present in an amount of 0.01% to 0.05%, or about 0.04%. For avoidance of doubt the term "about" in the context of polysorbate 80 concentration means a deviation of equal to or less than 10% from the stated concentration.

Arginine also acts as a stabilizer in the present formulations. Arginine is preferably present in an amount of 10 mM to 75 mM, 10 mM to about 50 mM, 10 mM to about 15 mM, or about 10 mM. For avoidance of doubt the term "about" in the context of arginine concentration means a deviation of equal to or less than 10% from the stated concentration.

Sodium chloride (NaCl) acts a tonicity agent in the present formulation. NaCl is present in an amount of 0.1% to 1.0%, about 0.3% to about 0.9%, or about 0.2% to about 0.5%, or about 0.3%. For avoidance of doubt the term "about" in the context of NaCl concentration means a deviation of equal to or less than 10% from the stated concentration. It is particularly advantageous for ocular formulations to be isotonic or slightly hypertonic (e.g., 315.6 mOsmol/liter).

As stated above, the manufacturer's formulation was used as an initial formulation. Subsequent excipient substitutions were screened and are detailed in Table 1. Dilutions of standard concentrations were made and tested by SE-HPLC. The efficiency of each formulation was judged by the slope of its standard curve, as described above.

TABLE 1

Ranibizumab Formulations Tested

| ID | H₂O | 0.9% NaCl | 0.3% NaCl | Trehal. % | Arg mM | Glu mM | His mM | T-20 % | T-80 % | P-127 % | pH |
|---|---|---|---|---|---|---|---|---|---|---|---|
| 1 | X | | | 10 | | | 10 | 0.01 | | | 5.5 |
| 2 | X | X | | 10 | | | 10 | 0.04 | | | 7.40 |
| 3 | X | X | | 10 | | | 10 | 0.01 | | | 7.40 |
| 4 | X | X | | 5 | | | 5 | 0.04 | | | 7.40 |
| 5 | X | X | | 5 | | | | 0.04 | | | 7.40 |
| 6 | X | X | | 10 | | | | 0.04 | | | 7.40 |
| 7 | X | X | | 5 | | | 10 | 0.04 | | | 6.53 |
| 8 | X | X | | 10 | | | | 0.04 | | | 6.53 |
| 9 | X | X | | 10 | 10 | | | 0.04 | | | 6.81 |
| 10 | X | | X | 10 | 10 | | | 0.04 | | | 6.81 |
| 11 | X | | X | 10 | 10 | 10 | | | | 1 | 6.81 |
| 12 | X | | X | 5 | 75 | 75 | | 0.04 | | | 6.61 |
| 13 | X | | X | 10 | 10 | | | | 0.04 | | 6.78 |
| 14 | X | | X | 7.5 | 10 | | | | 0.04 | | 6.78 |

In the above Table 1, Trehal. = Trehalose, T-20 = TWEEN ®20, T-80 = TWEEN ®80 and P-127 = PLURONIC ®F127.

It was found that each formulation had a discontinuity in the standard curve between the concentrations of 1,000 ng/ml and about 1,125 to 1,150 ng/ml. The observed slopes of the tested formulations and respective r² values are tabulated in Table 2 with the 2 different slopes split at the discontinuity.

TABLE 2

Slopes and respective r² values of the formulas of Table 1

| Formula | 3.9-1000 ng/ml Slope | R² | 1150-6000 ng/ml Slope | R² |
|---|---|---|---|---|
| 1 | 0.1211 | 0.9952 | 0.2666* | 0.9995 |
| 2 | 0.2321 | 0.9971 | 0.4189* | 0.9940 |
| 3 | 0.1317 | 0.9990 | 0.1618 | 0.9987 |
| 4 | 0.1808 | 0.9977 | 0.2104 | 0.9996 |
| 5 | 0.1628 | 0.9994 | 0.2126 | 0.9994 |
| 6 | 0.1808 | 0.9989 | 0.2244 | 0.9999 |
| 7 | 0.1681 | 0.9994 | 0.2297 | 0.9982 |
| 8 | 0.1697 | 0.9966 | 0.2510 | 0.9991 |
| 9 | 0.1766 | 0.9976 | 0.2549 | 0.9995 |
| 10 | 0.1908 | 0.9960 | 0.2819 | 0.9987 |
| 11 | 0.1363 | 0.9941 | 0.1888 | 1.0000 |
| 12 | 0.3440 | 0.9983 | 0.4843 | 0.9992 |
| 13 | 0.4343 | 0.9989 | 0.5124 | 1.0000 |
| 14 | 0.5385 | 0.9979 | 0.5805 | 1.0000 |

*1150 ng/ml-1500 ng/ml

Figure 7:
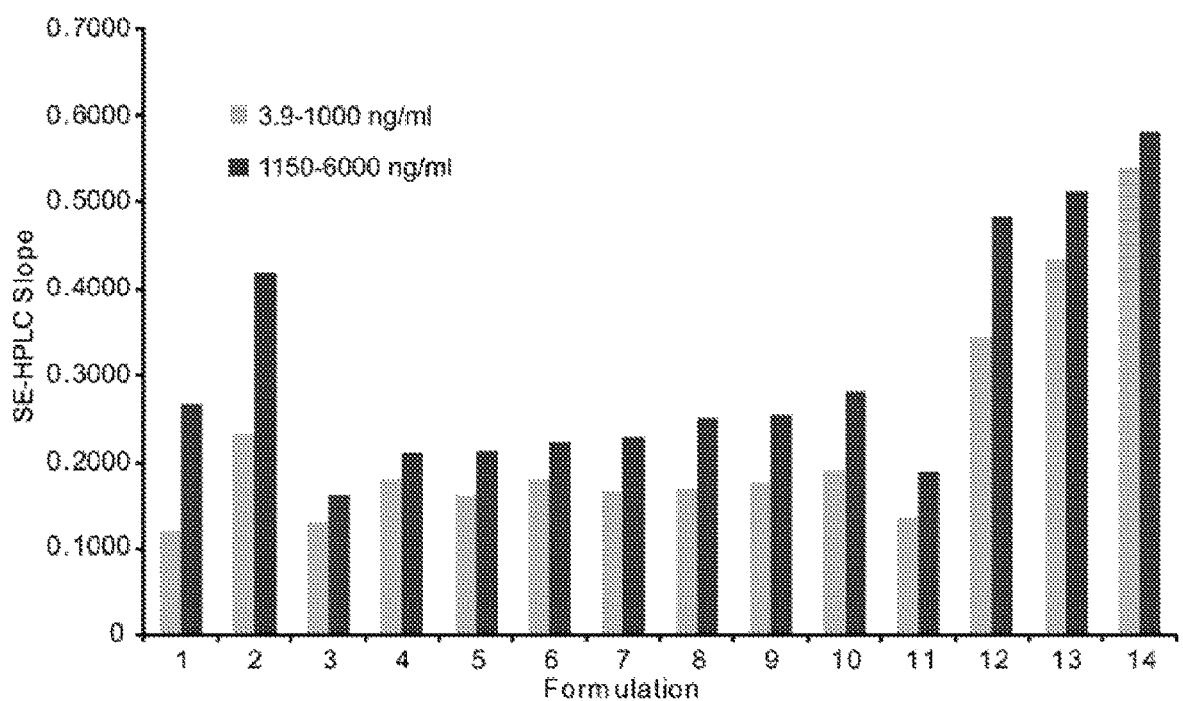
FIG. 7 provides a graphical representation of the effect of the formulations of Table 1 on the slope of the effect of dilution on monomer concentration of ranibizumab as measured by SE-HPLC.

A graphical representation of the results of Table 2 is shown in FIG. 7. Formulations 13 and 14 showed the best preservation of the monomer concentration by higher and nearly continuous concentration slope values as analyzed by SE-HPLC. Additionally, Formula 14 had the least difference between the lower concentration slope of 0.5385 and the higher concentration slope of 0.5805 giving an almost linear standard curve for concentrations 3.9 ng/ml-6,000 ng/ml.

In one embodiment, an exemplary formulation (Formula 14) is provided that contains 0.3% NaCl, 7.5% trehalose, 10 mM arginine, and 0.04% polysorbate 80, 100 mM sodium phosphate buffer with the balance being water at a pH of 6.78. The manufacturer's formula for ranibizumab includes 10% (100 mg/ml) α,α-trehalose, 0.01% (0.1 mg/ml) polysorbate 20 (TWEEN®20), and 10 mM (1.98 mg/ml) L-histidine in water for injection at pH 5.5. These excipients are well known and described in the literature. However, the present inventors found that replacing histidine (manufacturer's formulation) with arginine conferred a significant advantage. In addition, the salt concentration, in the case of PBS, was reduced (e.g., from 0.9% to 0.3%), while still approximating isotonicity and the pH was raised considerably above the manufacturer's carrier matrix composition. Polysorbate-80 at 0.04% was substituted for the 0.01% polysorbate-20 in ranibizumab; the 0.04% polysorbate-20 in bevacizumab and the 0.03% polysorbate-20 in aflibercept. This combination of excipients provided a surprising improvement in stability, particularly in light of the fact that manufacturers spend considerable efforts in optimizing their formulations to confer the best possible stability.

The formulation of Formula 14 comprises sodium phosphate buffer in an amount of about 5 mM to about 150 mM to achieve a pH of about 6.0 to about 7.4, about 6.0 to about 7.0, about 6.5 to about 7.0, about 6.6 to about 6.8, about 6.75 to about 7.0, about 6.8 to about 7.8, or about 6.7 to about 6.8. In one specific embodiment, the pH of the formulation is 6.78. These pH ranges are particularly advantageous for ocular formulations because they approximate the pH of normal tear film. Tear pH is 6.5-7.6, but may vary throughout the day and from patient to patient. The pH value is also an important factor in that in greatly impacts aggregation. Acidic pH conditions decrease aggregation, but may be less clinically tolerated. The present formulations are less acidic than comparative formulations, while still maintaining the biological activity of the biopharmaceutical agent.

Using Formula 14, it was found that there is no change in activity and stability even after 24 hours at body temperature (by SE-HPLC & ELISA). As disclosed in the examples herein, Formula 14 exhibits significantly higher slope values when compared to the manufacture's formulation for a range of biopharmaceuticals as exemplified by a humanized monoclonal produced in mammalian cell culture, a Fab humanized monoclonal produced in a prokaryotic cell line and a receptor-antibody fusion protein. The critical concentration point at 1000 to 1150 ng/ml was found to be no longer evident before and after exposure to 37° C. The same formulation 14 may make the drug more stable when injected into the eye thus extending the drug half-life within the eye.

Example 2

Materials and Methods

Materials:

L-Arginine, L-(+)-Glutamic Acid, L-Histidine, Glycine, sodium phosphate dibasic anhydrous, sodium phosphate monobasic monohydrate, sodium sulfate anhydrous, polysorbate 20 (TWEEN® 20), phosphate buffered saline (10λ), and HPLC water were obtained from Fisher Scientific Fair Lawn, N.J. Sodium chloride, α,α-trehalose dihydrate, polysorbate 80 (TWEEN®80, low peroxide), poloxamer 407 (PLUIRONIC® F127) were purchased from Sigma-Aldrich, St Louis Mo. and normal saline 0.9% was obtained from Baxter Healthcare Corp., Deerfield, Ill.

ELISA analytical kits for bevacizumab (kit #AVA-E-U51) and ranibizumab (kit #LUC-E-U52) were obtained from United Immunoassay Inc., San Bruno, Calif. USA. Aflibercept was analyzed using an ELISA materials, methods and procedure as described Celik et al., Intraocular Pharmacokinetics of Aflibercept and Vascular Endothelial Growth Factor-A. *Invest Ophthalmol Vis Sci* 56 (2015) 5574-5578.

Sample Analysis by Enzyme-linked immunosorbent assay (ELISA): bevacizumab and ranibizumab ELISA assays were performed as per manufacturer's instructions except for a substitution of the base analytical standard material which was taken from the pharmaceutical preparations obtained and diluted as described below. Aflibercept ELISA was performed as described by Celik et al. except for a substitution of the base analytical standard material which was taken from the pharmaceutical preparations obtained and diluted as described below. The ELISA method dynamic ranges are as follows: bevacizumab 1-281.25 ng/ml, ranibizumab 1-100 ng/ml and aflibercept 1-100 ng/ml.

Size-Exclusion High Performance Liquid Chromatography (SE-HPLC). Analytical size-exclusion chromatography was performed using an Agilent HPLC system HP1100 from Agilent Technologies (Santa Clara, Calif.) with a UV detector. Studies were performed using a TSKgel UltraSW Aggregate 7.8 mm×30 cm, 3 µm SEC column with TSKgel UltraSW guard column (Tosoh Bioscience LLC, King of Prussia, Pa.). Mobile phase comprising 85% 100 mM sodium sulfate in 100 mM phosphate buffer in HPLC water (adjusted to pH 6.68) with 15% acetonitrile/0.1% trifluoroacetic acid was used at a flow rate of 0.6 ml/min. Sample injections were 100 µl in volume. The eluted protein was monitored by UV Absorbance at 212 nm. Silanized HPLC sample vials and silanized vial inserts from Agilent Technologies (Santa Clara, Calif.), were used throughout.

In some experiments, serial dilutions for ELISA and SE-HPLC analysis were made as follows: A starting concentration of the subject antibody as provided by the manufacturer (bevacizumab 25 mg/ml and ranibizumab 10 mg/ml) was diluted volume to weight (v/w) with the subject diluent matrix to a concentration of 100 µg/ml (100,000 ng/ml). This 100 µg/ml was then diluted volume to volume (v/v) to 10,000 ng/ml as a starting concentration. The 10,000 ng/ml solution was diluted v/v to 6,000 ng/ml. The 6,000 ng/ml solution was then diluted volume to volume (v/v) with the subject diluent in steps providing ng/ml concentrations at 3000, 1500, 1250, and 1150. An intermediate dilution of 1,000 ng/ml was made and that 1,000 ng/ml solution was serially diluted in 1:1 steps providing 500, 250, 125, 62.5, 31.25, 15.625, 7.8125, 3.90125 ng/ml. The 250 ng/ml dilution was used for the high standard concentration for bevacizumab ELISA. The 125 ng/ml was used for the high standard concentration for the ranibizumab ELISA In some other experiments, serial dilutions for ELISA and SE-HPLC analysis were made as follows: A starting concentration of the subject antibody as provided by the manufacturer (bevacizumab 25 mg/ml, ranibizumab 10 mg/ml and aflibercept 48.2 mg/ml) was diluted volume to weight (v/w) with the subject diluent matrix to a concentration of 144 µg/ml (144,000 ng/ml). This starting concentration was then diluted volume to volume (v/v) with the subject diluent in 1:1 steps providing ng/ml concentrations at 72000, 36000, 18000, 9000, 4500, 2250, 1125, 562.50, 281.25, 140.62, 70.31, 35.156, 17.578, 8.79, 4.39, 2.197 and 1.0985. An intermediate dilution of 1,000 ng/ml was made from the 2,250 ng/ml step. To provide certain calibration standard ranges for ELISA method ranges, for example, an additional dilution of 225 ng/ml was made from the 2,250 ng/ml bevacizumab dilution for that ELISA method. An intermediate dilution of 100 ng/ml was made from the 1,000 ng/ml dilution for ranibizumab and for aflibercept for those ELISA methods.

In Vitro Experiments of Formulations:

Based upon the manufacturer's formulation, excipient substitutions were screened with dilutions of standard concentrations of ranibizumab. These are shown in Table 1. Water, PBS, saline (0.9% NaCl) and 0.3% NaCl solutions were used as the starting solutions. Other than the manufacturer's formulation, sodium phosphate buffer was used in the formulations. Trehalose was used throughout the formulations, owing to its protein stabilizing quality. The amino acids arginine, glycine, histidine and glutamic acid were tested in various capacities. Surfactants were also tested. The manufacturer's formulation contained 0.01% TWEEN® 20. Concentrations of 0.01% and 0.04% of TWEEN® 20 were screened. Another surfactant, TWEEN® 80, was tested at a concentration of 0.04%. Additionally, PLURONIC® F127 was tested. Finally, pH was looked at as a variable in the formulations. These were then analyzed by SE-HPLC. The most stabilizing formulation, Formula 14, was chosen for further analysis.

Stability Study.

Specific formulations of ranibizumab were tested for stability. Sets of standard dilutions ranging from 3.9 ng/ml to 6,000 ng/ml were prepared from Formulas 1, 3 and 14. Formula 1 is the manufacturer's formula, Formula 3 is PBS with excipients and Formula 14 is a new formulation. These solutions were divided in half and one set was analyzed as time 0 and the other set was incubated at 37° C. for 24 hrs. Both sets were analyzed by SE-HPLC.

Degassing Study.

A series of ranibizumab standards was prepared in order to test the issue of degassing the formulation. Briefly, 10 ml of Formula 14 were introduced into two, 15 ml conical tubes respectively. One tube was then degassed under vacuum, with stirring, for 1 hour. The other tube was not degassed. Serial standard solutions of ranibizumab, ranging from 3.9 ng/ml to 10,000 ng/ml, were then prepared from the degassed and non-degassed formula 14. These sets were then analyzed by SE-HPLC.

Results of In Vitro Experiments

Formulations.

As stated above, the manufacturer's carrier matrix formulation of ranibizumab was used as an initial formulation to be evaluated. Subsequent excipient substitutions were screened and are detailed in Table 1. Dilutions of standard concentrations were made and tested by SE-HPLC. The efficiency of each formulation was judged by the slope of its standard curve. It was found that each formulation had a discontinuity in the standard curve between the concentrations of 1,000 ng/m and 1,150 ng/ml. These slopes and respective $r^2$ values are tabulated in Table 2. A graphical representation is shown in FIG. 7. Formulations 13 and 14 showed the best recovery values as analyzed by SE-HPLC. Additionally, formula 14 had the least difference between the lower concentration slope (3.9-1,000 ng/ml) of 0.5385 and the higher concentration slope (1,150-6,000 ng/ml) of 0.5805 giving an almost linear standard curve over the entire concentration range 3.9 ng/ml-6,000 ng/ml.

Figure 8:
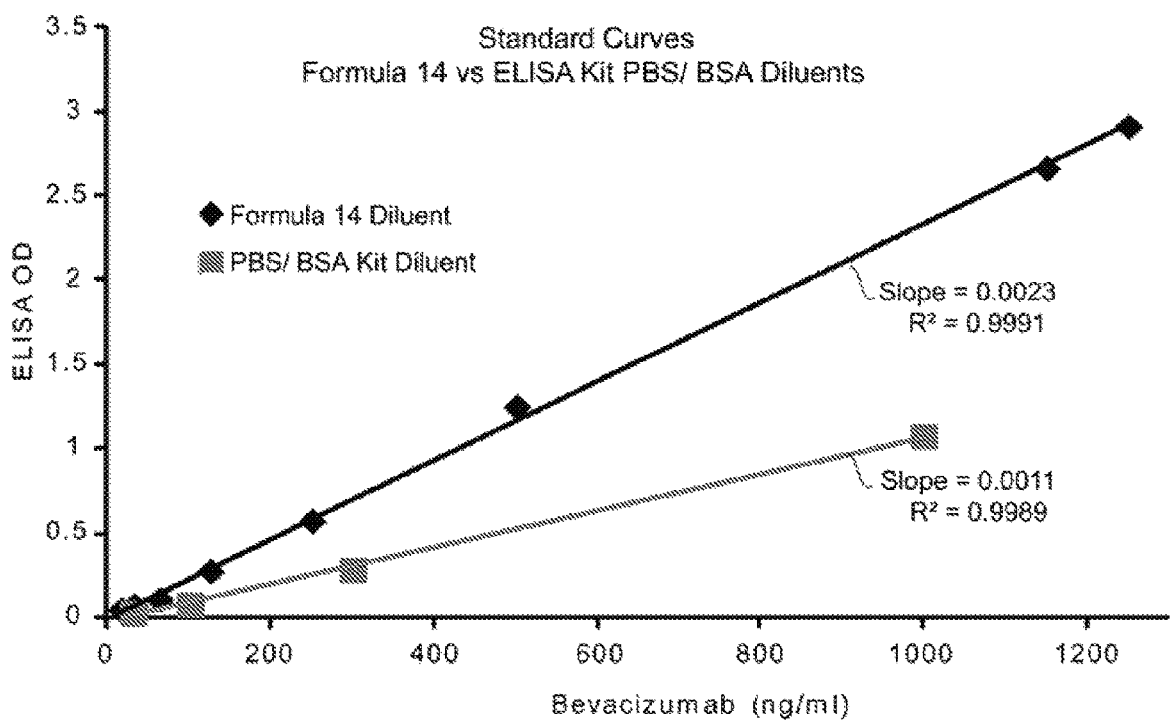
FIG. 8 depicts the slopes of detectable bevacizumab by ELISA as a measure of activity comparing Formula 14 with a PBS/BSA kit diluent. Standard curves were prepared using side by side wells on the same plate and same conditions.

Formula 14 was also tested with bevacizumab by ELISA, in order to show the activity of the mAbs (FIG. 8). Standard curves were prepared using side by side wells on the same plate and same conditions. As drug aggregates, the binding sites are reduced diminishing the assay optical density vs a stable drug with available binding sites. Data plot slope of ELISA values indicate activity; the higher the slope value the more the activity Formula 14 generated a 2× higher slope when compared to the ELISA kit standards, which was bovine serum albumen (BSA) in PBS, indicating more drug VEGF binding. This significant difference demonstrates the ELISA kit reagents/methods cause significant mAb aggregation either in standard dilution preparation during manufacture and/or in dilution of standards prior to assay plating.

Stability Study:

Several of the formulations were tested for stability. Sets of ranibizumab standard dilutions ranging from 3.9 ng/ml to 6,000 ng/ml were prepared from formulation 1, 3 and 14. Stability tests were conducted at 37° C. for 24 hrs. These were then analyzed by SE-HPLC (see FIGS. 5, 6 and 9).

Figure 6:
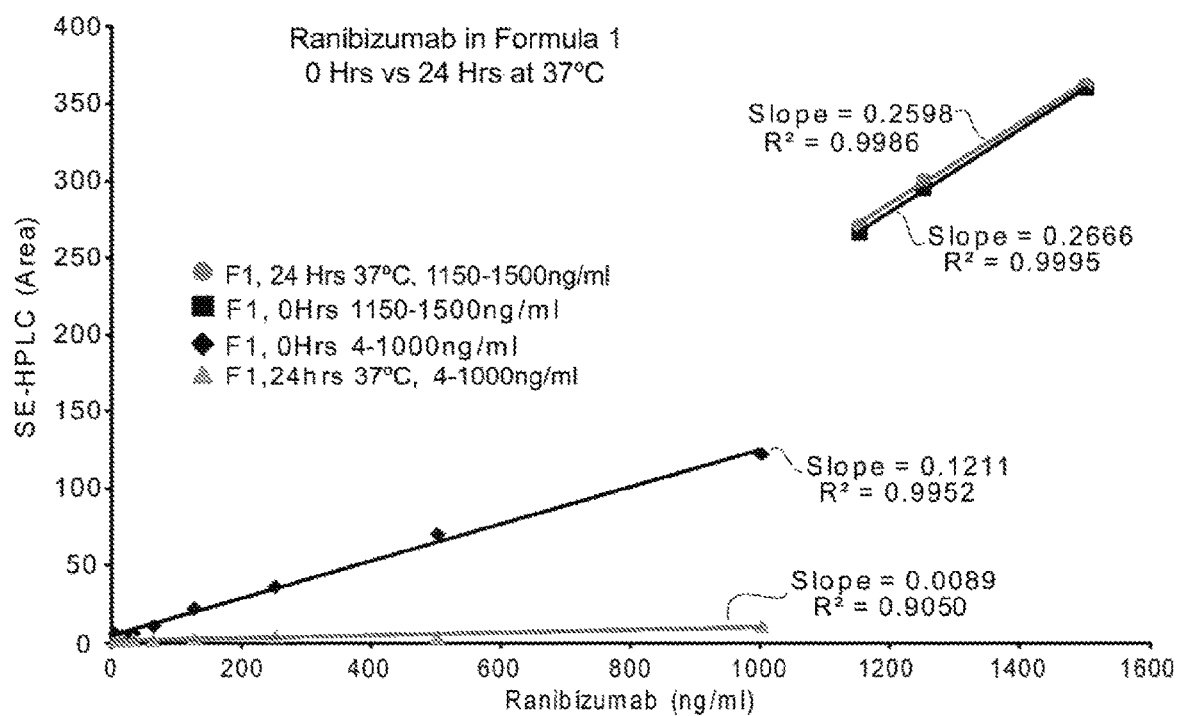
FIG. 6 shows a graphical representation of SE-HPLC area and depicts the slope of the effect of dilution on aggregation of ranibizumab over time at 37° C. with formula 1 at 0 time and after 24 hour storage at 37° C.
Figure 9:
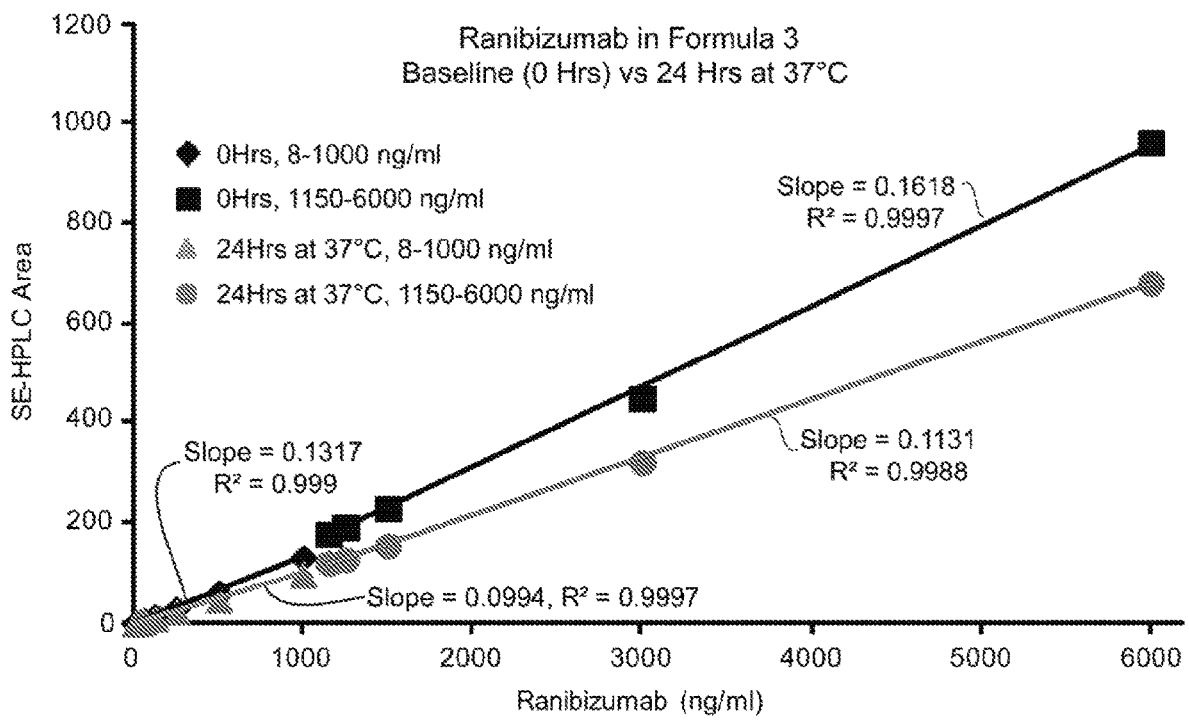
FIG. 9 shows the stability of ranibizumab at 0 time versus 24 hours at 37° C. in formula 3.

As seen in FIG. 6, the manufacturer's formulation, here known as Formula 1, for ranibizumab shows a discontinuity between 1,000 ng/ml and 1,150 ng/ml. The more dilute concentrations have a slope of 0.1211, whereas the concentrations above 1,150 ng/ml have a slope of 0.2666. When the manufacturer's formulation is subjected to body temperature for 24 hours (as would be found in a 24 hour permeation experiment), the ranibizumab all but disappears in the lower concentrations with a slope of 0.0089. The concentrations at 1,150 ng/ml and above are detected and with a slope of 0.2598. FIG. 9 shows the stability of ranibizumab at 0 time versus 24 hours at 37° C. in formula 3.

Figure 10A:
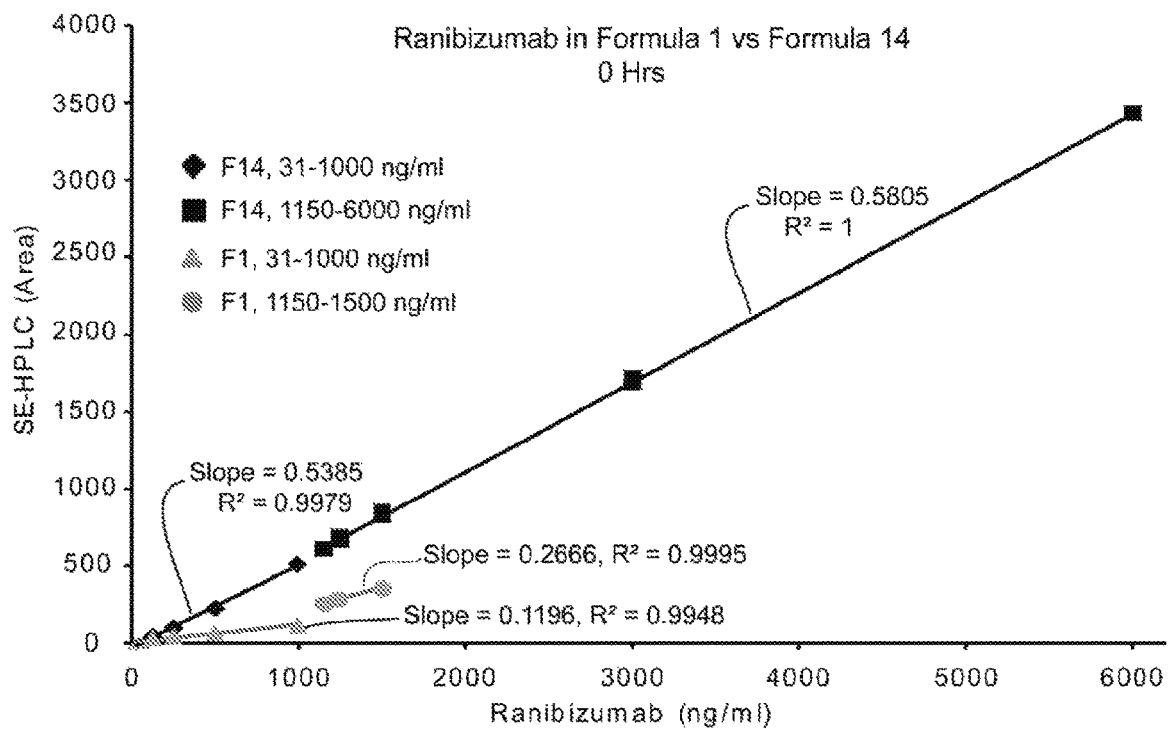
FIG. 10A shows that when ranibizumab is diluted in the same formulation used by the manufacture there is an immediate 40% loss of monomer concentration, when compared to Formula 14.

FIG. 10A shows that when ranibizumab is diluted to low concentrations <1,125 ng/ml in the same carrier matrix formulation used by the manufacturer, there is an immediate 40% loss of drug activity, when compared to Formula 14. Heating to body temperature significantly produces more degradation, as shown in FIG. 10B.

Figure 10B:
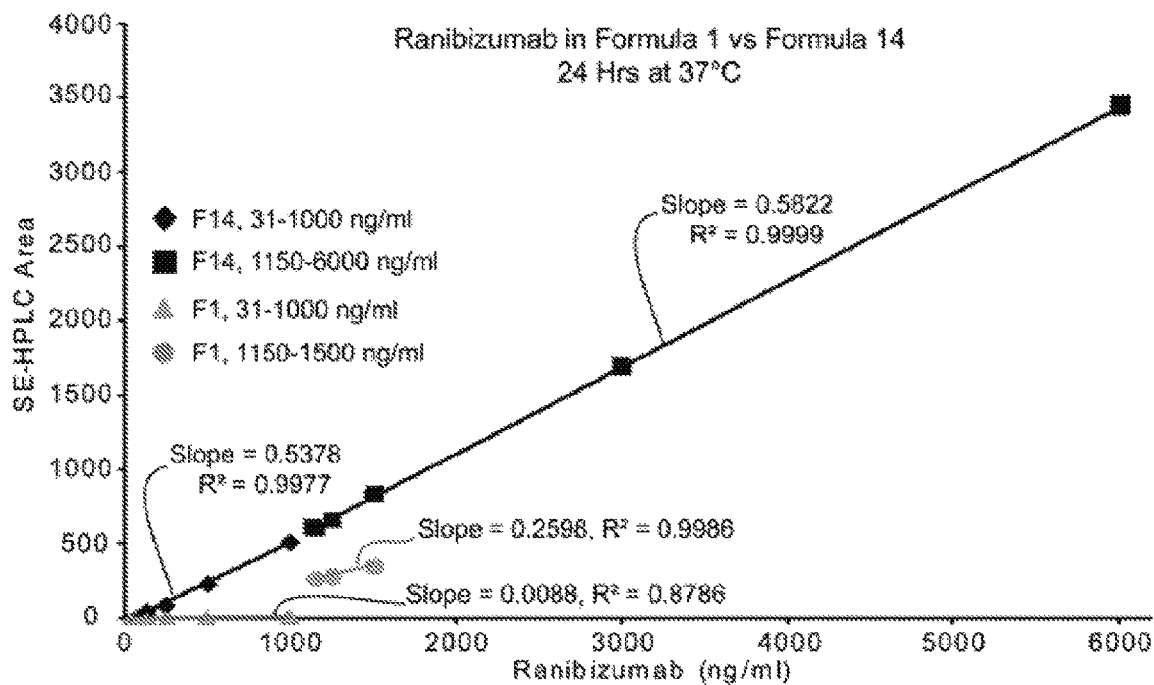
FIG. 10B shows that heating to body temperature significantly produces more degradation.

When using Formula 14, the critical concentration point at 1000 to 1,150 ng/ml is much less evident before and after exposure to 37° C., as seen in FIG. 10B. Note the significantly higher slope values when compared to the manufacturer's formulation herein known as formula 1. Ranibizumab, when diluted in the manufacturer's matrix formulation, has a critical concentration point between 1,000 and 1,125 ng/ml where the slopes differ in serial dilutions below 1,150 ng/ml and above 1,150 ng/ml.

Figure 11:
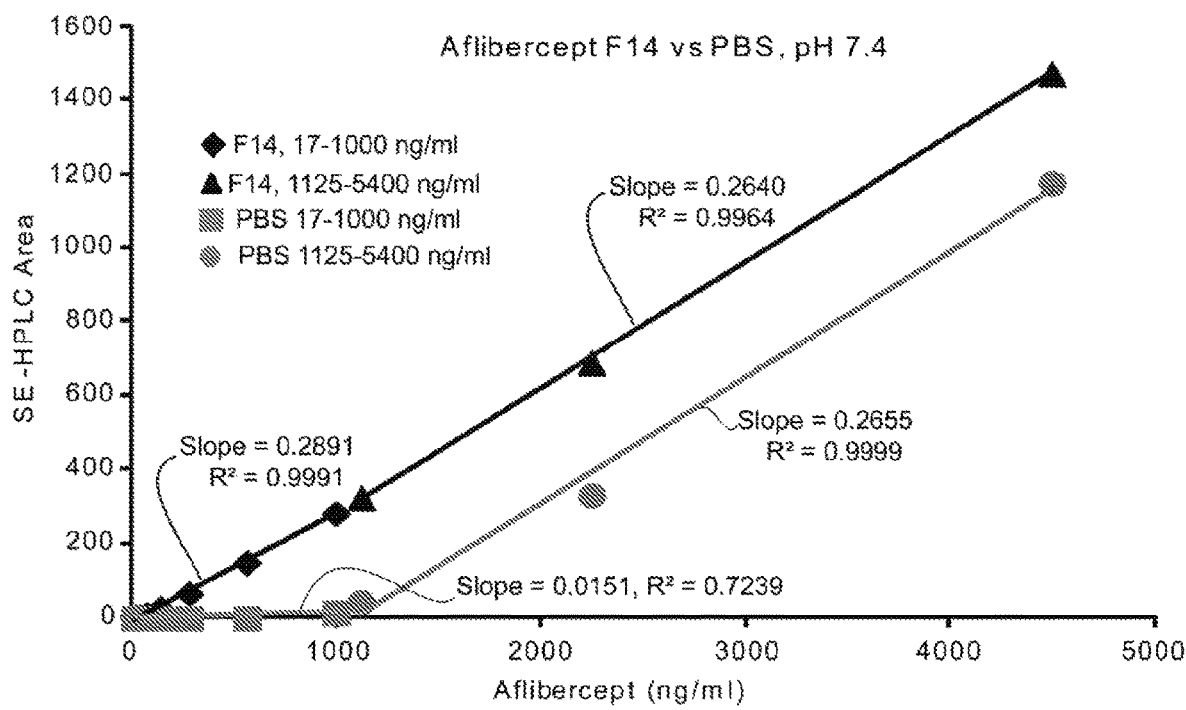
FIG. 11 shows SE-HPLC slopes for aflibercept diluted with formula 14 vs. PBS.

Additionally, aflibercept exhibits a similar discontinuation of slope values when diluted with PBS compared to dilutions with formula 14. FIG. 11 shows SE-HPLC slopes of aflibercept concentrations for Formula 14 compared to PBS. The Formula 14 slope is nearly continuous and linear compared to the greatly reduced slope for PBS at concentrations below 1,000 ng/ml.

Degassing Study.

A series of ranibizumab standards was prepared in order to test the issue of degassing the formulation. Serial standard solutions, ranging from 3.9 ng/ml to 10,000 ng/ml, were prepared from degassed and non-degassed formula 14.

Figure 12:
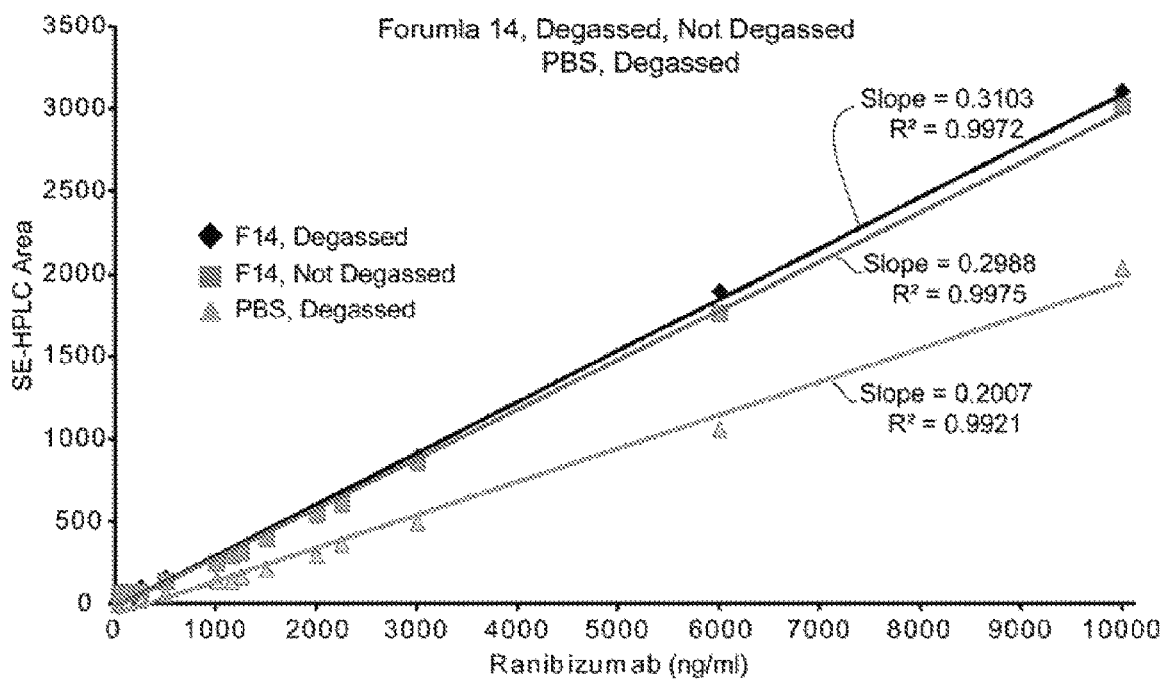
FIG. 12 shows the results of a degassing experiment with ranibizumab in Formula 14.
Figure 13:
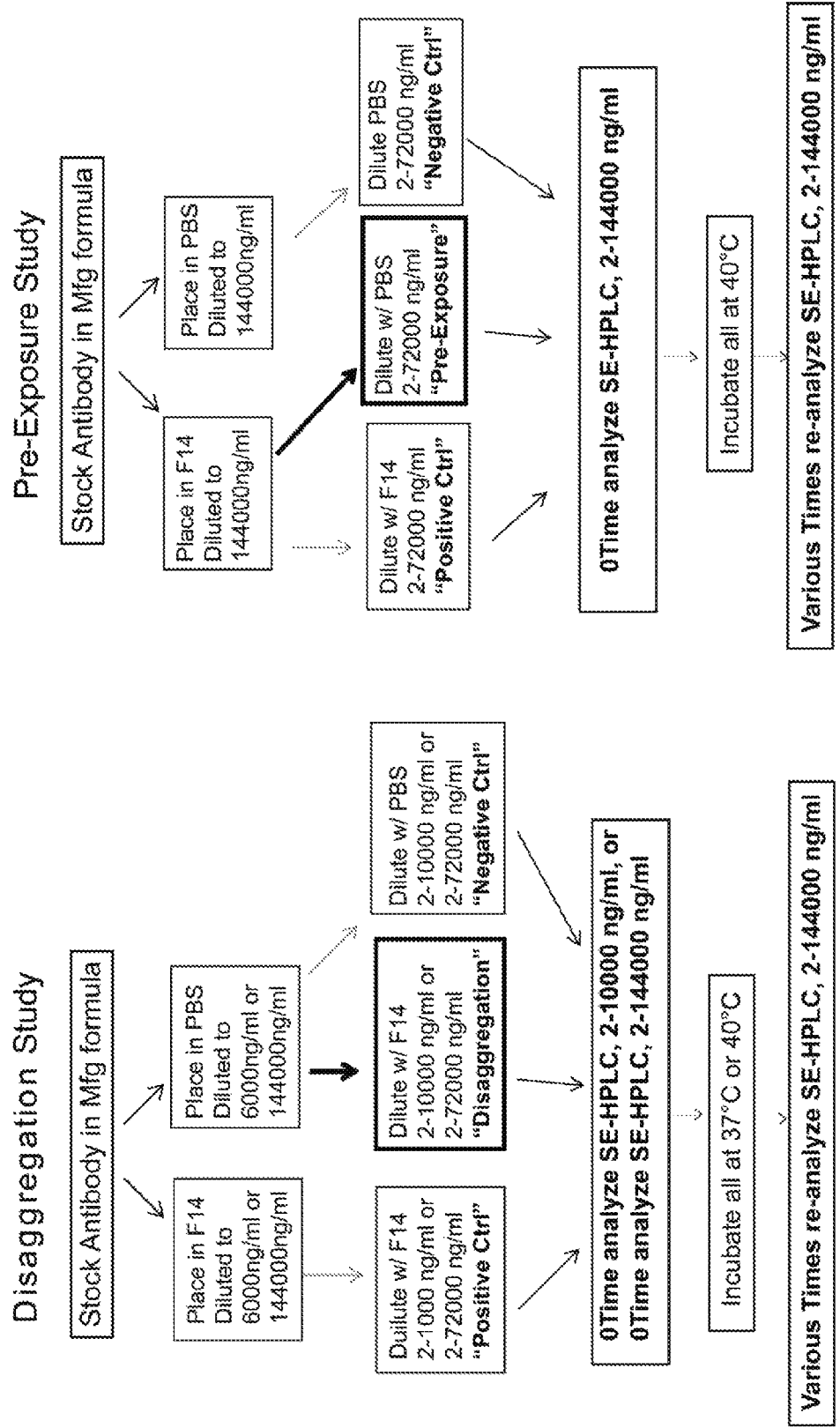
FIG. 13 depicts a flow chart and dilution strategy to examine formula 14 disaggregation potential and ability of formula 14 to protect from aggregation by pre-exposing antibodies to formula 14.

Shown in FIG. 12, are the results of the degassing experiment. The standards, when in PBS and not degassed were of a lower concentration, having a slope of 0.2007. When the standards were prepared with non-degassed formula 14, the recovery increased and the slope was 0.2988. The recovery increased even more when the ranibizumab standards were prepared in degassed formula 14. Here, the slope improves from 0.2988 to 0.3103.

When Formula 14 was degassed and tested against non-degassed Formula 14 and PBS, the degassed formula was 5% higher in recovery than non-degassed formula and 44% higher in recovery than the PBS solution.

Example 3

Antibody Disaggregation and Antibody Pre-Exposure to Prevent Aggregation

Hydrophobic areas on the antibody surface are considered to be the most probable point of antibody aggregation. The mechanism of aggregation may be due to the formation of dissolved gas bubble bridges between two or more antibodies. The subject Formula 14 appears to exhibit superior anti-aggregation potential regardless of mechanism. Without being bound by theory, the formula 14 excipient combination appears to coat the hydrophobic surface areas of the antibodies and eliminate or reduce the attachment of nanobubbles to those hydrophobic areas and thus reduce aggregation potential.

Once more, without being bound by theory, an excipient combination, also comprising a surfactant, that exhibits strong anti-aggregation potential, would have the potential to invade the hydrophobic surfaces, liberate the attached dissolved gas on the hydrophilic areas and break apart or dis-aggregate an antibody aggregate complex.

An antibody stabilization carrier matrix formulation may have usefulness in antibody production and pre-packaging steps prior to final packaging for distribution. It would be advantageous and useful if an antibody carrier matrix exhibited a potential to reverse or dis-aggregate dimer, trimer and higher order antibody aggregates in a solution. A dis-aggregation potential would be useful in downstream antibody manufacturing (cell culture harvest) as well as upstream processing (i.e. filtration, concentration and packaging) to increase production yield and reduce process losses.

Again without being bound by theory, if the antibody hydrophobic areas are transformed into a more hydrophilic state, then the bonds between the hydrophobic surface and the excipient that hold those transforming excipient in place on the antibody surface, may be strong enough to remain even after the antibodies are placed in an alternate carrier matrix. If the hydrophobic areas remain transformed into a hydrophilic state, the antibody may have resistance to subsequent aggregation if placed in carrier matrices that have little anti-aggregation potential.

It would also be advantageous if an antibody stabilization carrier matrix formulation exhibited anti-aggregation potential in antibodies pre-exposed to the subject matrix formulation and then subsequently diluted or packaged with an alternate carrier matrix. An anti-aggregation pre-treatment may be useful, for example, when antibody formulations are diluted into normal (0.9%) saline for intravenous administration. It would also be useful when an antibody formulation is administered into the eye vitreous wherein there is little endogenous protein buffer that may prevent aggregation.

Ranibizumab and aflibercept were used as model antibodies to determine the anti-aggregation or "disaggregation" potential of formula 14. Ranibizumab and aflibercept were also used as model antibodies to determine the reduced potential of aggregation by "pre-exposure" to Formula 14 prior to dilution with a carrier matrix with little anti-aggregation potential. FIG. 13 presents a flow chart of these experimental procedures.

For the "disaggregation" evaluation, ranibizumab 10 mg/ml was diluted in formula 14 to a concentration of 100 μg/ml as a positive control. Ranibizumab 10 mg/ml was diluted in PBS to a concentration of 100 μg/ml as a negative control. Both were incubated at 37° C. for 17 hours to allow for aggregation. After incubation, disaggregation potential was assessed by subsequent dilution of the 100 μg/ml PBS by Formula 14 from 10,000 ng/ml to 3.9 ng/ml. The positive control Formula 14 and the negative control PBS were also diluted with the respective diluents 10,000 ng/ml to 3.9 ng/ml. Samples were analyzed by SE-HPLC; peak area values were plotted against the concentration and slope values were determined. Ranibizumab disaggregation SE-HPLC area plots are shown in FIG. 14.

For the "disaggregation" evaluation, aflibercept 48.2 mg/ml was diluted in formula 14 to a concentration of 144 μg/ml as a positive control. Aflibercept 48.2 mg/ml was diluted in PBS to a concentration of 144 μg/ml as a negative control. Disaggregation potential was assessed by subsequent dilution of the 144 μg/ml PBS by Formula 14 from 72,000 ng/ml to 2.197 ng/ml. The positive control Formula 14 and the negative control PBS were also diluted with the respective diluents 72,000 ng/ml to 2.197 ng/ml. Samples were analyzed by SE-HPLC; peak area values were plotted against the concentration and slope values were determined. After the individual samples were analyzed by SE-HPLC they were placed in an incubator at 37° C. for 5 days and then reanalyzed by SE-HPLC. Aflibercept disaggregation SE-HPLC area plots are shown in FIGS. 15 A-B and FIGS. 16 A-B.

For "Pre-Exposure" to prevent aggregation evaluation, ranibizumab 10 mg/ml was diluted in formula 14 to a concentration of 144 μg/ml as a positive control. Ranibizumab 10 mg/ml was diluted in PBS to a concentration of 144 μg/ml as a negative control. Pre-exposure anti-aggregation potential was assessed by subsequent dilution of the 144 μg/ml Formula 14 with PBS from 72,000 ng/ml to 2.197 ng/ml. The positive control Formula 14 and the negative control PBS were also diluted with the respective diluents 72,000 ng/ml to 2.197 ng/ml. Samples were analyzed by SE-HPLC; peak area values were plotted against the concentration and slope values were determined. Ranibizumab pre-exposure SE-HPLC area plots are shown in FIGS. 17 A-B For "Pre-Exposure" to prevent aggregation evaluation, aflibercept 48.2 mg/ml was diluted in formula 14 to a concentration of 144 µg/ml as a positive control. Aflibercept 48.2 mg/ml was diluted in PBS to a concentration of 144 µg/ml as a negative control. Pre-exposure anti-aggregation potential was assessed by subsequent dilution of the 144 µg/ml Formula 14 with PBS from 72,000 ng/ml to 2.197 ng/ml. The positive control Formula 14 and the negative control PBS were also diluted with the respective diluents 72,000 ng/ml to 2.197 ng/ml. Samples were analyzed by SE-HPLC; peak area values were plotted against the concentration and slope values were determined. After the individual samples were analyzed by SE-HPLC they were placed in an incubator at 37° C. for 12 days and then reanalyzed by SE-HPLC. Aflibercept time 0 pre-exposure anti-aggregation SE-HPLC area plots are shown in FIGS. 18 A-B and Aflibercept time 12 day incubation pre-exposure anti-aggregation SE-HPLC area plots are shown in FIGS. 19 A-B.

Antibody Disaggregation and Antibody Pre-Exposure to Prevent Aggregation Results:

Disaggregation Test. A disaggregation study was run in order to test the reversibility of mAb aggregation with formula 14. For this study, ranibizumab was placed into degassed formula 14 (100 ug/ml) and stored overnight (17 hours, 40° C.) to serve as a positive control. Ranibizumab was also placed into PBS (100 ug/ml) and stored overnight (17 hours, 40° C.), to allow for aggregation. The ranibizumab, placed in PBS, was then diluted with formula 14 and separately with PBS as a negative control. Serial standard dilutions were made for HPLC ranging from 2 ng/ml to 72,000 ng/ml.

Figure 14:
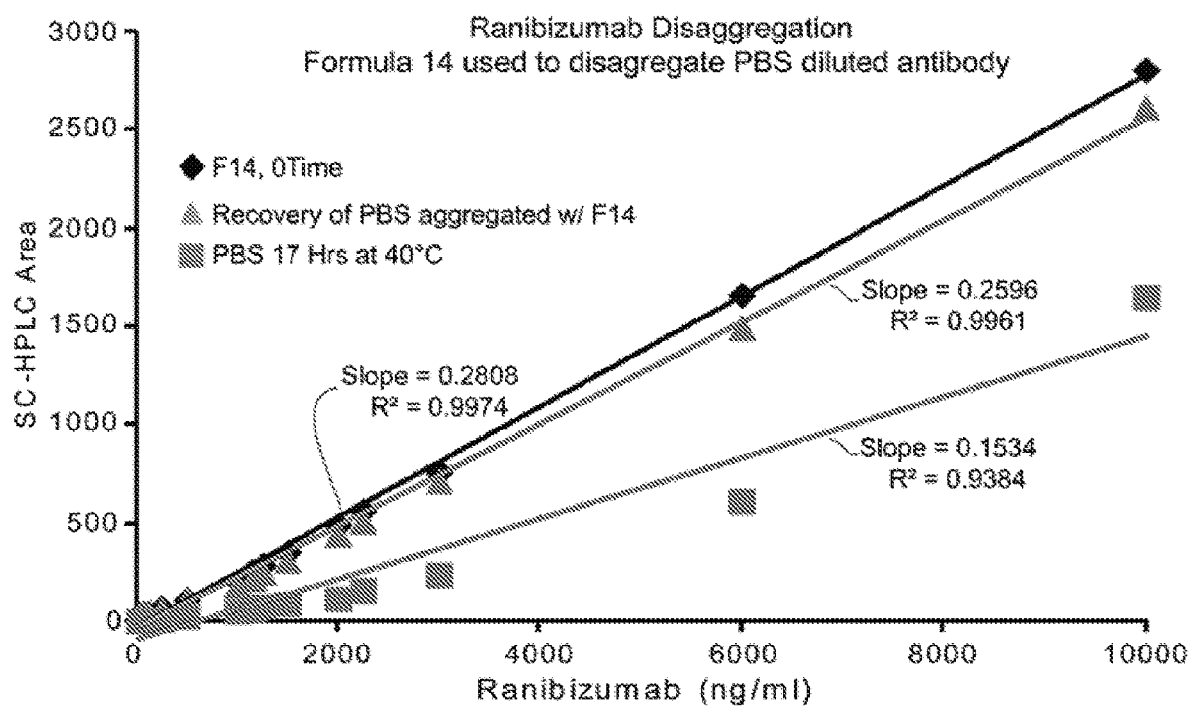
FIG. 14 shows the ability of Formula 14 to disaggregate aggregated forms ranibizumab as compared with PBS.

The results from the disaggregation study are shown in FIG. 14. As can be seen, the ranibizumab in PBS has a lower recovery, with a slope of 0.1543. However, when the ranibizumab/PBS is introduced to the formula 14, the recovery rebounds with a slope of 0.2596 for formula 14. This value is close to the slope of 0.2808, which is the slope representing ranibizumab, when placed in formula 14 from the beginning. From this experiment we can see that the mAb can be recovered by formula 14, when the mAb has first been treated with PBS.

A disaggregation study was run in order to test the reversibility of mAb aggregation with formula 14. For this study, aflibercept was placed into degassed formulation 14 (100 ug/ml) and stored overnight (17 hours, 40° C.) to serve as a positive control. Aflibercept was also placed into PBS (100 ug/ml) and stored overnight (17 hours, 40° C.), to allow for aggregation. The aflibercept, placed in PBS, was then diluted with formula 14 and separately with PBS as a negative control. Serial standard dilutions were made for SE-HPLC ranging from 2.197 ng/ml to 72,000 ng/ml.

Figure 15A:
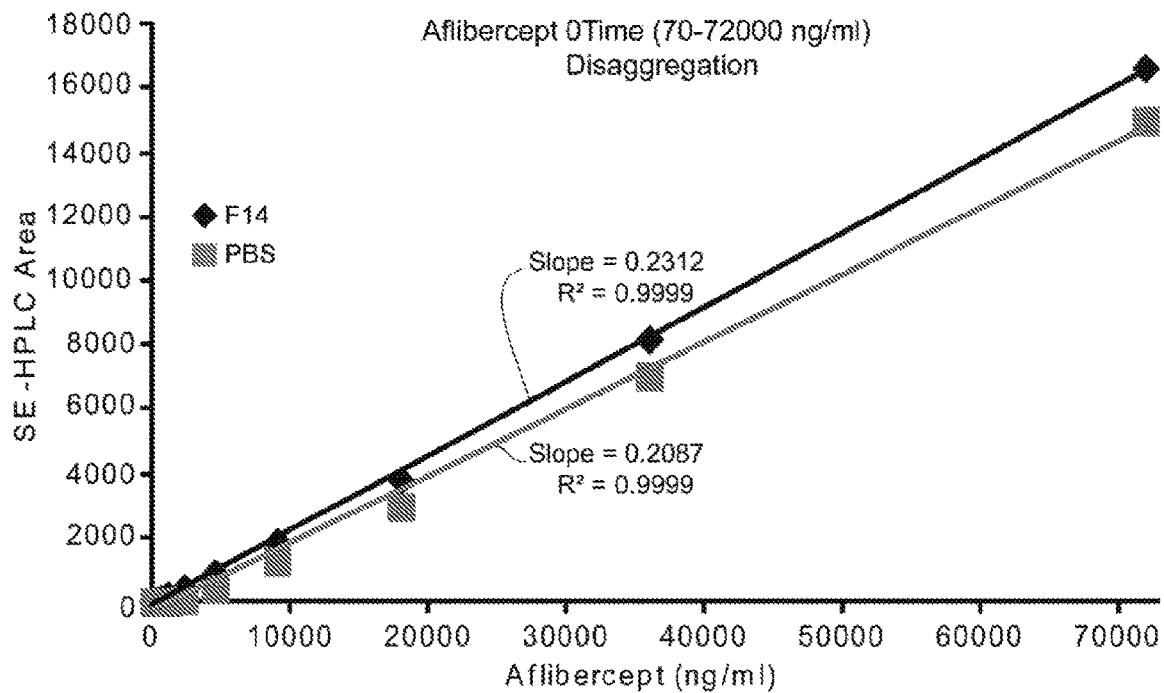
FIGS. 15A and 15B show the ability of Formula 14 to disaggregate aggregated forms aflibercept as compared with PBS at time 0.
Figure 15B:
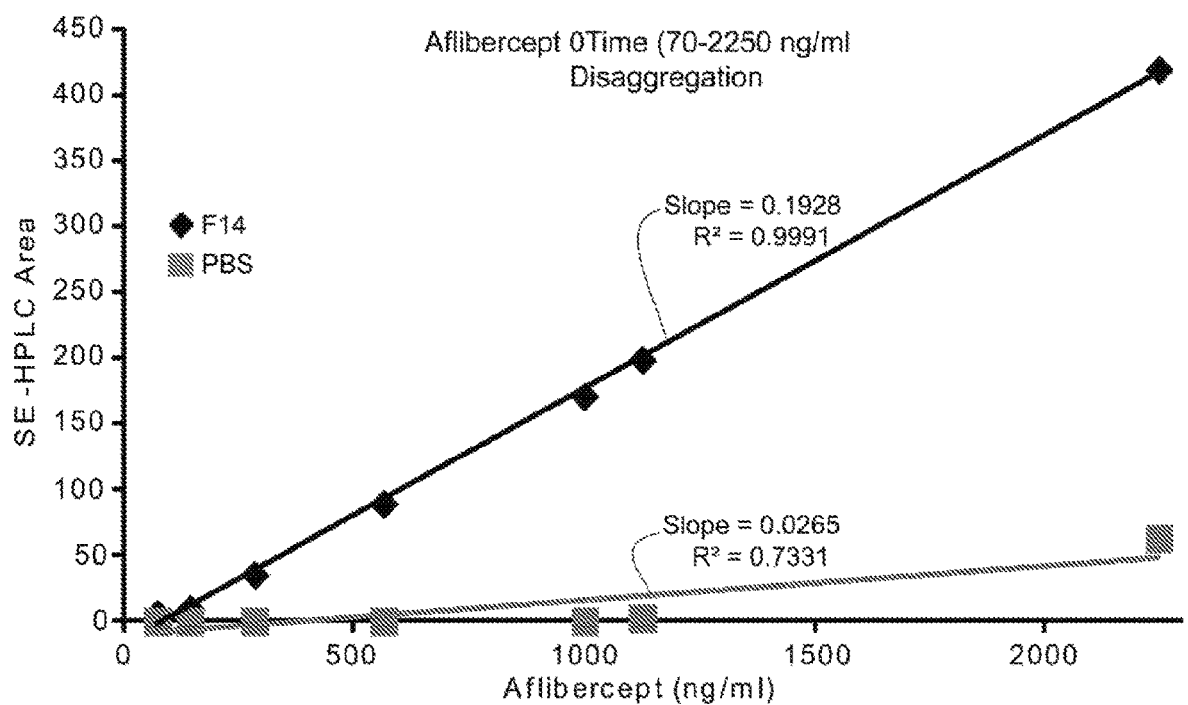

FIGS. 15A and B show the time 0 results. FIG. 15A shows the full range of dilutions. FIG. 15B shows only the lower dilutions. In FIG. 15A, the initial loss of aflibercept is apparent with a slope of 0.2087 as compared to the formula 14 with a slope of 0.2312. In FIG. 15B, the difference between the two dilutions is more pronounced with the PBS dilutions having a slope of 0.0265 as compared to formula 14 which has a slope of 0.1928.

Figure 16A:
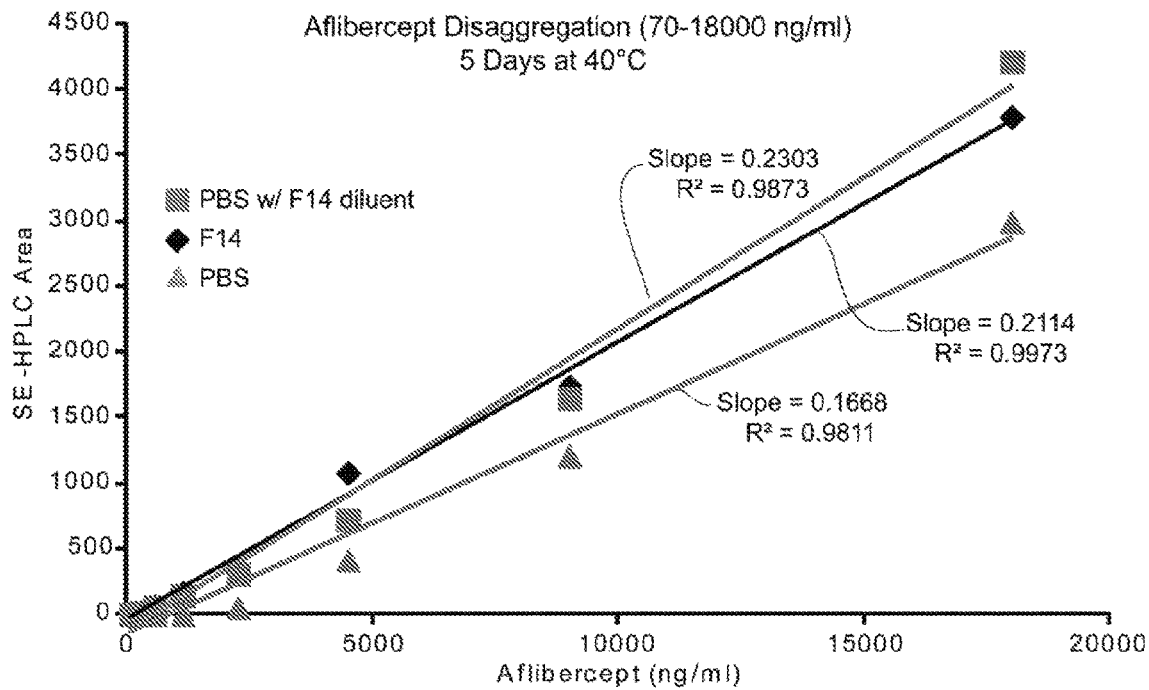
FIGS. 16A and 16B show the ability of Formula 14 to disaggregate aggregated forms aflibercept as compared with PBS at day 5 at 40° C.
Figure 16B:
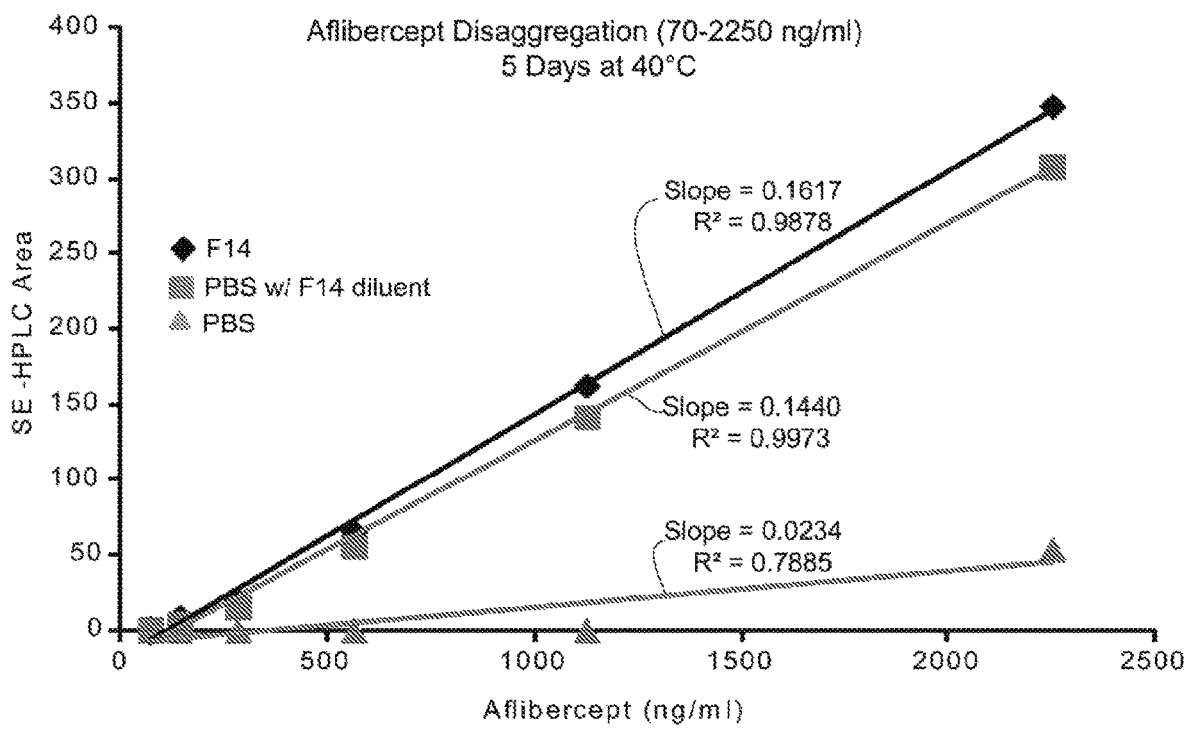

FIGS. 16A and B show day 5 results. FIG. 16A shows the full range of dilutions. FIG. 16B shows only the lower dilutions. FIG. 16A shows that when aflibercept is aggregated in PBS and then diluted in formula 14, the recovery is almost equal to or better than when aflibercept is placed and diluted in formula 14. This is mirrored in the results shown in FIG. 16B. From this experiment, it can be seen that a fusion protein can be recovered by formula 14, when the mAb has first been treated (aggregated) with PBS.

Pre-exposure Test. A pre-exposure test was run in order to test the mAb preservative quality of formula 14 when challenged with PBS. For this test, ranibizumab, and later aflibercept, was placed into formula 14 (144 µg/ml). They were then diluted with PBS. A positive control was made using the ranibizumab or aflibercept placed into formula 14 (144 µg/ml) and then diluted into formula 14. A negative control was also made by using the ranibizumab or aflibercept placed into PBS (144 µg/ml) and then diluted into PBS.

Figure 17A:
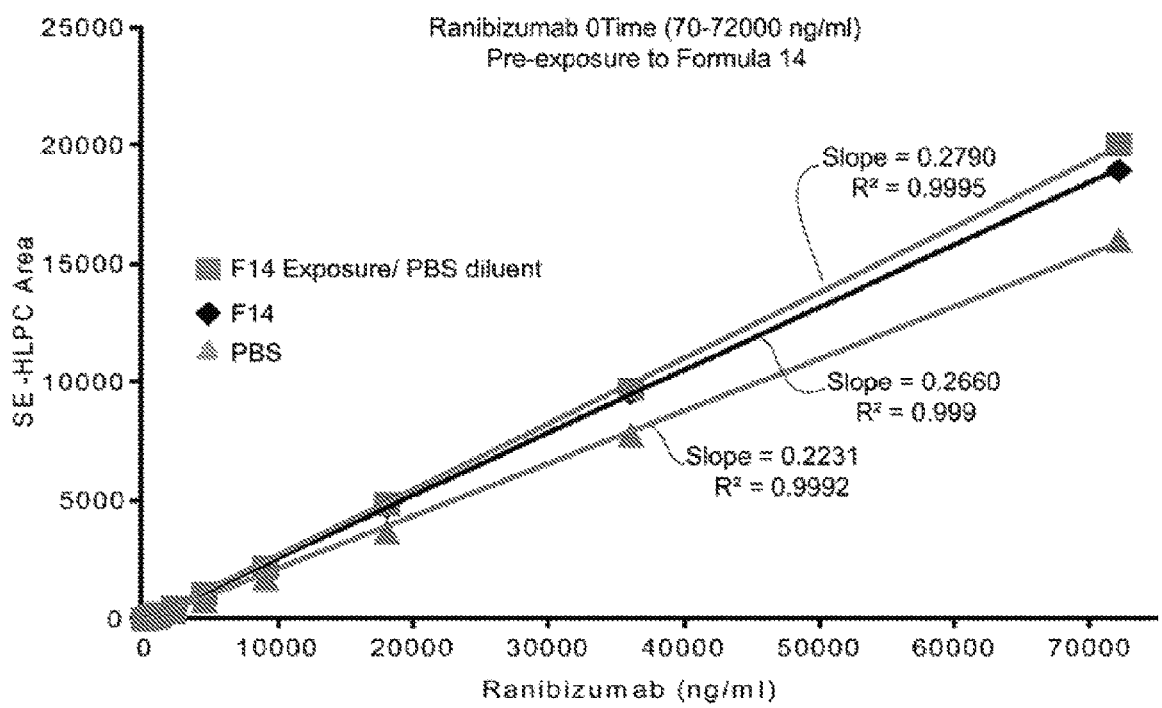
FIGS. 17A and 17B show the effects of pre-exposure to Formula 14 on subsequent aggregation of ranibizumab upon dilution.

FIG. 17A shows ranibizumab in PBS has a lower recovery, with a slope of 0.2231. However, when the ranibizumab/formula 14 is introduced to the PBS, the recovery is strong with a slope of 0.2790. These values are close to the slope of 0.2660, which is the slope representing ranibizumab, when placed in formula 14 from the beginning. From this experiment, it can be seen that the mAb can be protected by formula 14 when the mAb has first been treated with formula 14 and then diluted with PBS.

Figure 17B:
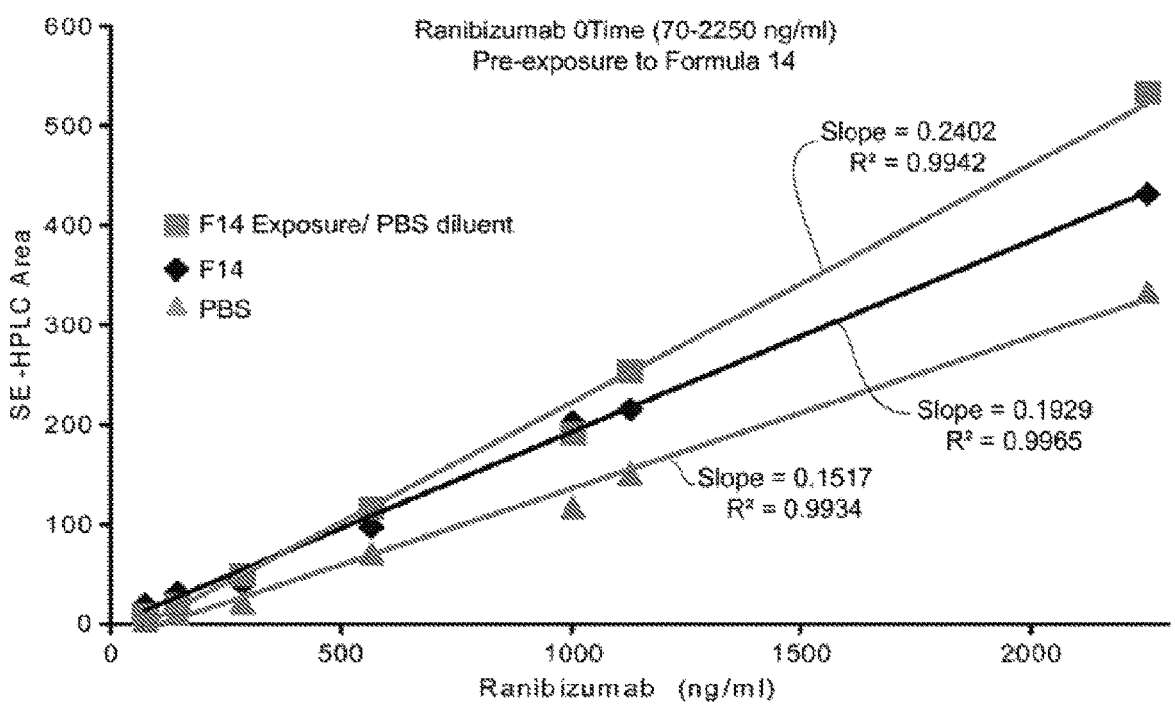

FIG. 17B shows the protective effect of formula 14 is more pronounced at the lower concentrations. In this figure, the PBS alone has a low recovery with a slope of 0.1517. The formula 14 protected ranibizumab, when diluted into formula 14, has a much higher recovery with a slope of 0.1929. And, the formula 14 protected ranibizumab, when diluted into PBS, has an even higher recovery with a slope of 0.2402. This means that formula 14 can be used as a primary diluent which protects the mAbs from aggregating. Subsequent dilution with PBS or formula 14 may then be accomplished with no further loss of mAbs.

Figure 18A:
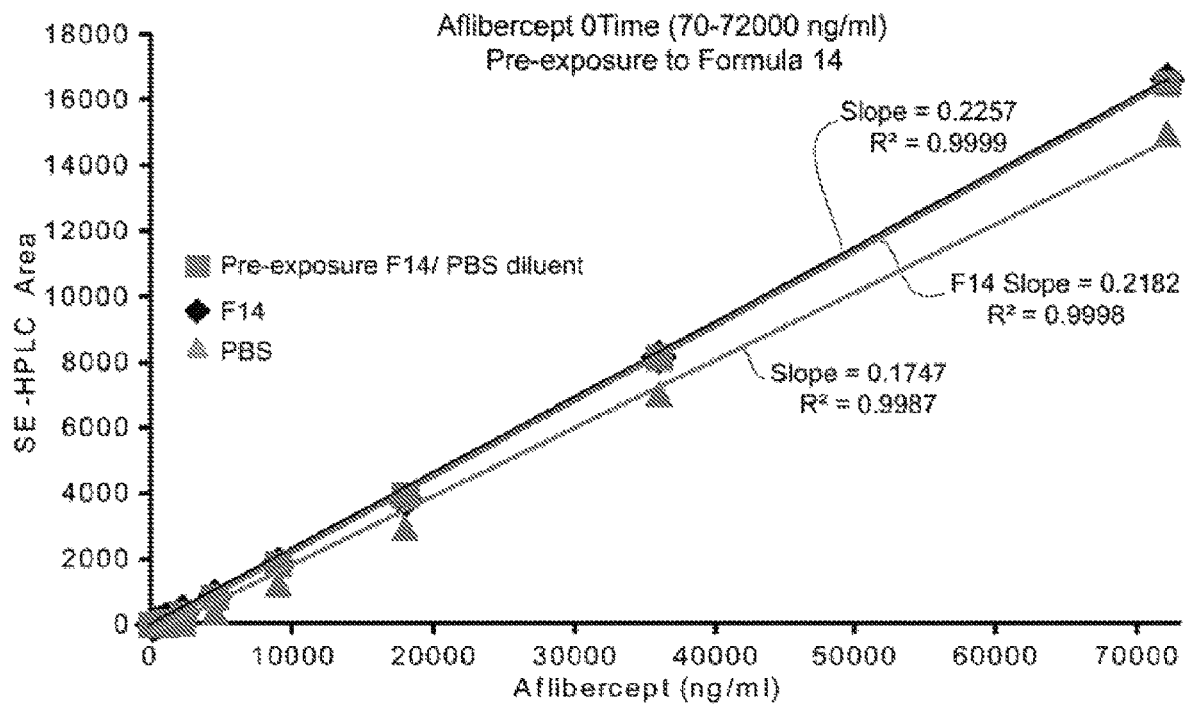
FIGS. 18A and 18B show the effect of pre-exposure Formula 14 on aflibercept aggregation.

FIGS. 18A and B show the effect of formula 14 pre-exposure on aflibercept. A pre-exposure test was run in order to test the reversibility of mAb aggregation with formula 14. For this test, aflibercept was placed into formula 14 (100 ug/ml). It was then diluted with PBS. A positive control was made using aflibercept placed into formula 14 (100 ug/ml) and then diluted into formula 14. A negative control was also made by using aflibercept placed into PBS (100 ug/ml) and then diluted into PBS.

Figure 18B:
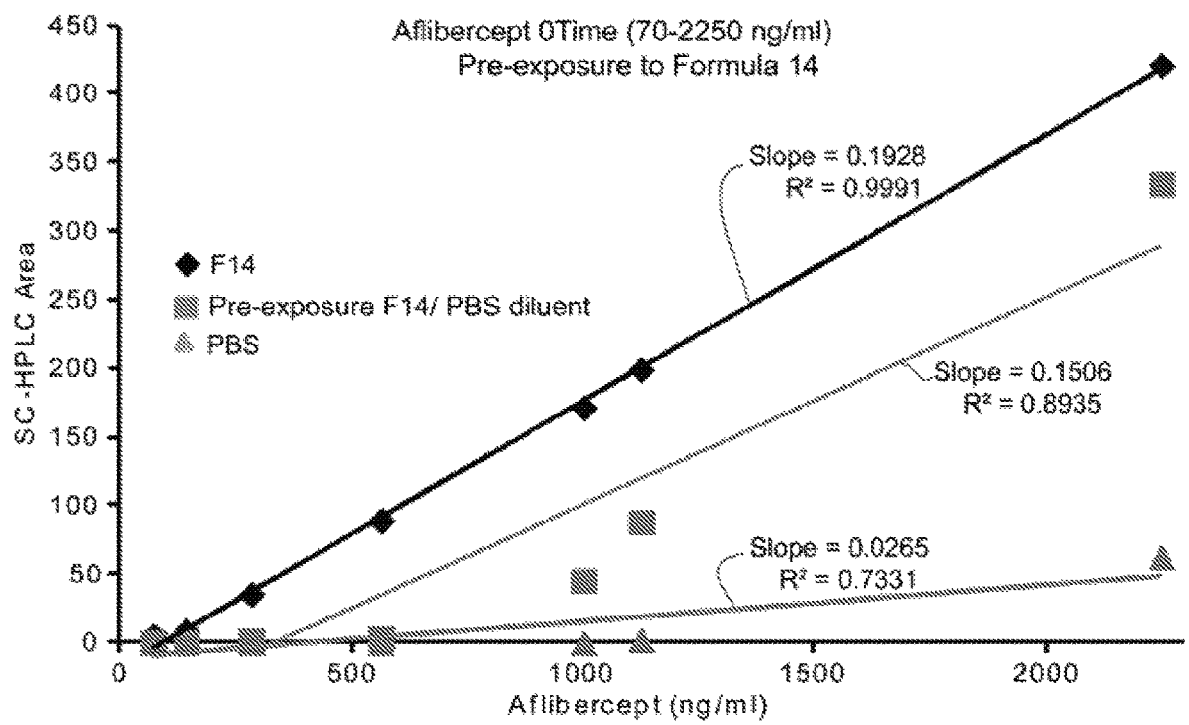

FIG. 18A shows the higher concentrations. The PBS alone shows a loss of aflibercept with a slope of 0.1747. The formula 14 and formula 14 diluted in PBS have very similar slopes of 0.2182 and 0.2257 respectively. FIG. 18B shows the lower dilutions. Here the PBS slope is 0.0265. This is much lower than aflibercept pre-exposed with formula 14 and diluted in PBS which has a slope of 0.1506. When aflibercept is placed in formula 14 and then diluted in formula 14, the recovery is better with a slope of 0.1928. From this experiment we can see that the fusion protein can be protected by formula 14, when the fusion protein has first been treated with formula 14 and then diluted with PBS.

Figure 19A:
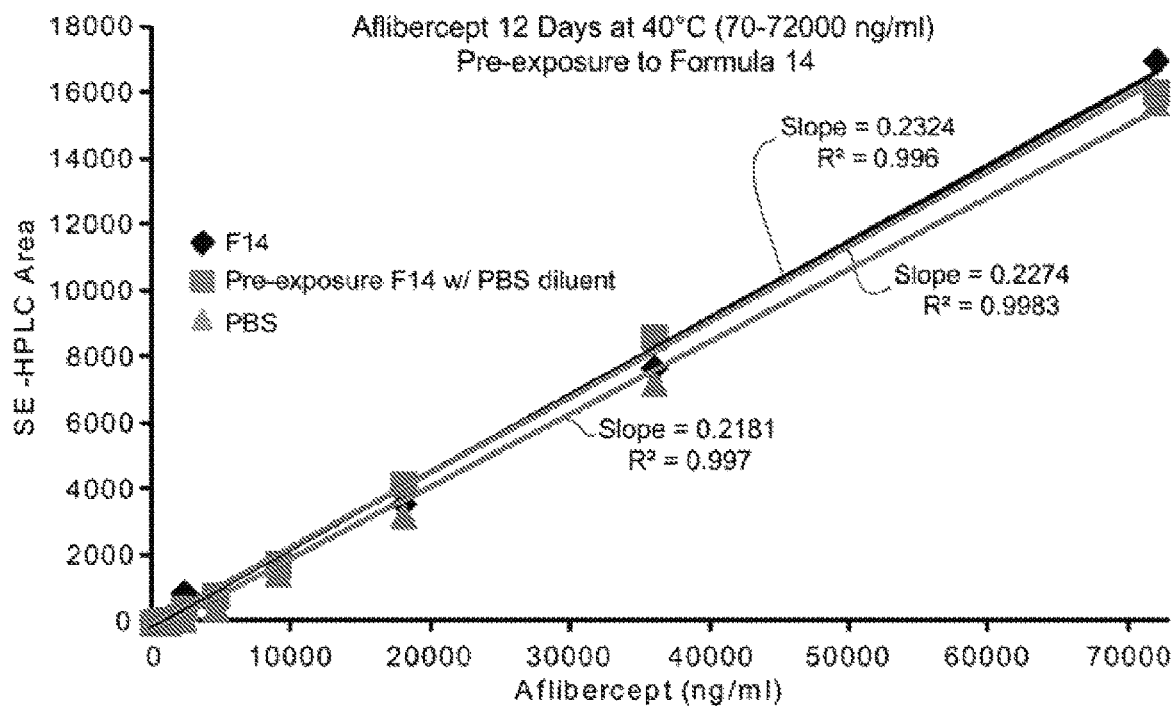
FIGS. 19A and 19B show day 12 results of the effect of pre-exposure to Formula 14 on aflibercept aggregation.
Figure 19B:
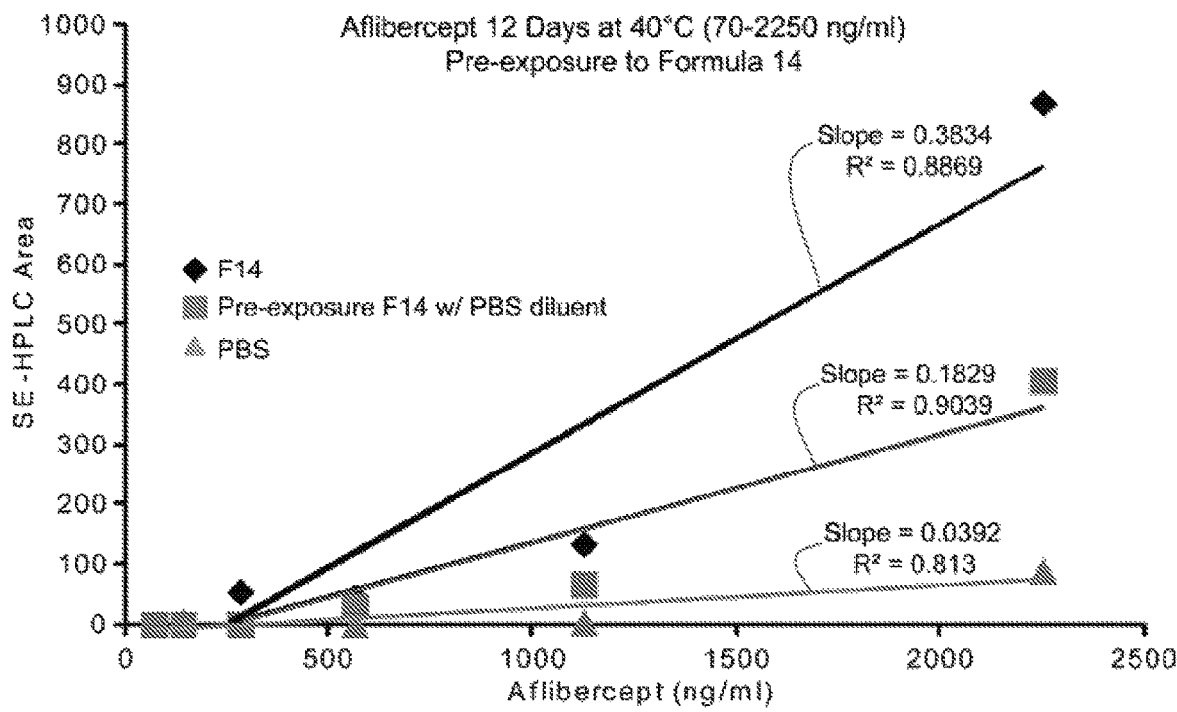

FIGS. 19A and B show day 12 results with aflibercept. FIG. 19A shows the full range of dilutions. FIG. 19B shows only the lower dilutions. FIG. 19A shows that when aflibercept is pre-exposed in formula 14 and then diluted in formula PBS, the recovery is almost equal to or better than when aflibercept is placed and diluted in PBS. This is mirrored in the results shown in FIG. 19B. From this experiment we can see that a fusion protein can be protected by formula 14, and remain stable for 12 days, when the fusion protein has first been treated with formula 14 and then diluted with PBS.

FIG. 20 shows the concentration of trehalose, polysorbate 80 and arginine in each diluted sample using formula 14. The initial exposure to the three excipients is fairly high. However, upon dilution they become very low. And even though the concentrations are very low, the 3 excipients work synergistically to protect the mAbs from degradation. In other words, exposure to high excipients and then subsequent dilution protects the mAbs from degradation.

Example 4 pH Range 6.78-7.8

The effects of changing pH for that of the manufacturer's formulations were tested. Aflibercept dilutions in the manufacturer's composition were tested vs. Formula 14 at pH 6.78 and pH 7.4. Ranibizumab dilutions in the manufacturer's composition were tested vs. Formula 14 at pH 6.78, pH 7.0, pH 7.4 and pH 7.8.

A diluent composition identical to the aflibercept (EYLEA®) packaged diluent composition comprising 10 mM sodium phosphate, 40 mM sodium chloride, 0.03% polysorbate 20, 5% sucrose, pH 6.2, with the balance being ultra pure water. Formula 14 at pH 6.78 and pH 7.4 were used as a comparison. Aflibercept 48.2 mg/ml was first diluted to 144,000 ng/ml and then further serially diluted 1:1 concentration dilution steps from 72,000 ng/ml to 8.789 ng/ml. Diluted samples from 8.789 ng/ml to 18,000 ng/ml were then analyzed by Size Exclusion HPLC (SE-HPLC) as previously described. A usable analytical range of 35.1562 to 18,000 ng/ml was selected. SE-HPLC areas were then plotted against concentrations as shown in FIG. 21.

Figure 21:
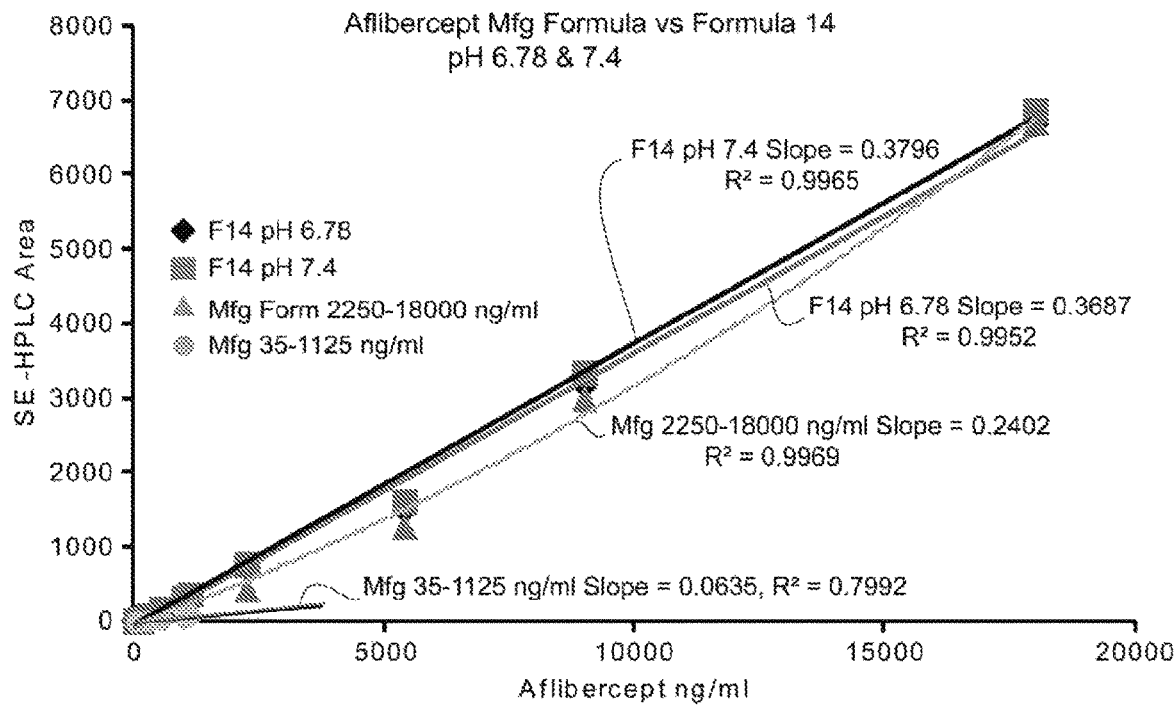
FIG. 21 shows the effects of different pH versions of Formula 14 on aflibercept monomer concentration.

As shown in FIG. 21, aflibercept in the manufacturer formulation at concentrations from 35.1562 to 1,125 ng/ml produced an SE-HPLC slope of 0.0635. Aflibercept in the manufacturer formulation at concentrations 2,250 ng/ml to 18,000 ng/ml produced an SE-HPLC slope of about 0.2402. Aflibercept dilutions over the entire range of 35.1562 to 18,000 ng/ml in formula 14 at pH of 6.78 and 7.4 showed SE-HPLC slopes of 0.3687 and 0.3796 respectively. This demonstrates that the manufacturer's composition did not protect aflibercept from aggregation at low concentrations while Formula 14 at higher pH values protected the antibody from aggregation.

Figure 22:
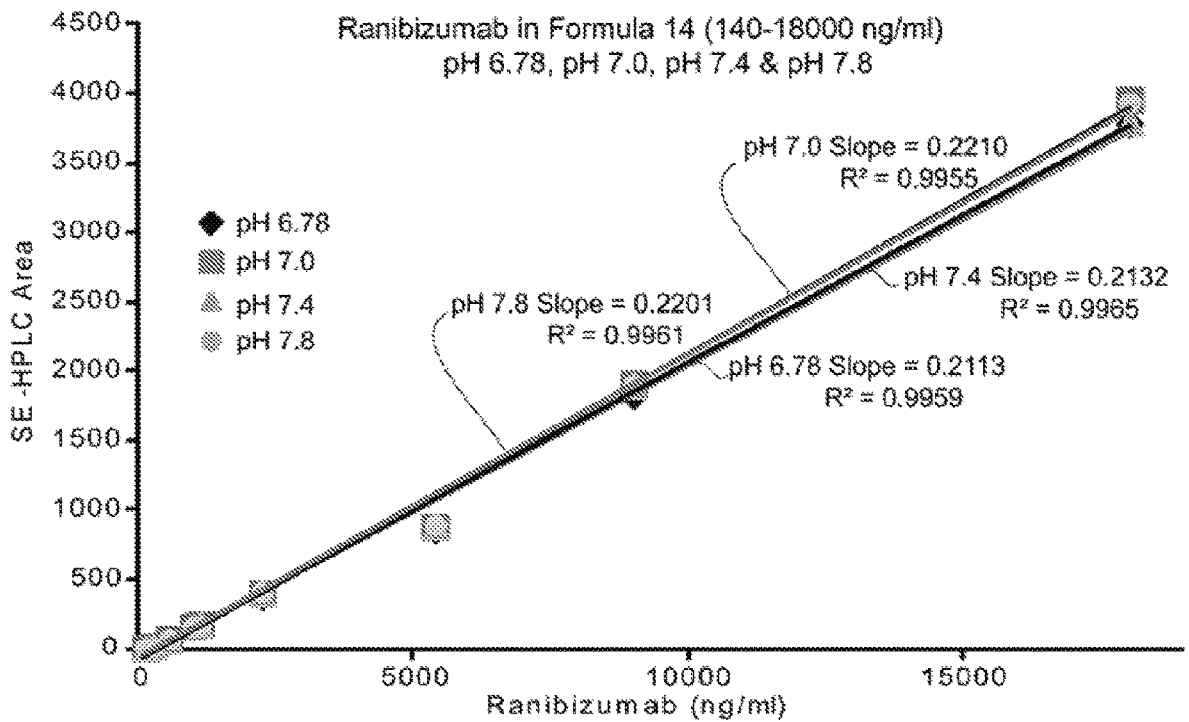
FIG. 22 shows the effects of different pH versions of Formula 14 on ranibizumab monomer concentration.

FIG. 22 depicts the results of ranibizumab dilutions in Formula 14 at pH values from 6.78 to 7.8. Formula 14 preparations at pH values of 6.78, 7.0, 7.4 and 7.8 were prepared and used as a comparison to determine the effects of pH on SE-HPLC area. Ranibizumab 10 mg/ml was first diluted to 144,000 ng/ml and then further serially diluted in 1:1 concentration dilution steps from 72,000 ng/ml to 8.789 ng/ml. Diluted samples from 8.789 ng/ml to 18,000 ng/ml were then analyzed by Size Exclusion HPLC (SE-HPLC) as previously described. A usable analytical range of 140.625 to 18,000 ng/ml was selected. SE-HPLC areas were then plotted against concentrations as shown in FIG. 22. As shown, there appears to be no pH dependence of when using formula 14. Slopes for the four compositions were essentially the same. This demonstrates that formula 14 overcomes narrow ranges of usable pH. Furthermore Formula 14 can be used as a diluent for mAb compositions at a physiologic pH of 7.4.

Example 5

Immunoassay Antibody Dilution

In addition to therapeutic drug applications, antibodies are used in immunoassay procedures and may benefit from compounding with the subject carrier matrix. Immunoassay antibodies are commonly diluted with PBS and/or PBS/BSA mixtures, then used in the various assays. In certain applications, bovine serum albumin may interfere with some assay analysis by cross reactivity, so a protein free antibody diluent may be preferred. Detection antibodies may be diluted for introduction into immunoassay methods at 0.2 µg/ml to about 0.02 µg/ml; however, there may be significant further dilution at the local binding site by endogenous matrices surrounding the antibody binding site. It would be advantageous to have immunoassay antibodies resistant to aggregation at low concentrations. Furthermore, a method to make immunoassay antibodies resistant to aggregation may useful to extend storage temperature ranges, shipping temperature ranges as well as storage life once reconstituted or thawed from a frozen state.

Anti-rhodamine antibody designated 11H10 (Cat #GTX29093 GeneTex Inc, Irvine Calif.) at 1 mg/ml formulated in a carrier matrix comprising 150 mM sodium chloride, 20 mM potassium phosphate, pH 7.2 with 0.01% sodium azide as a preservative with the balance being water. This antibody is generally stored at −20° C. until use.

Figure 23:
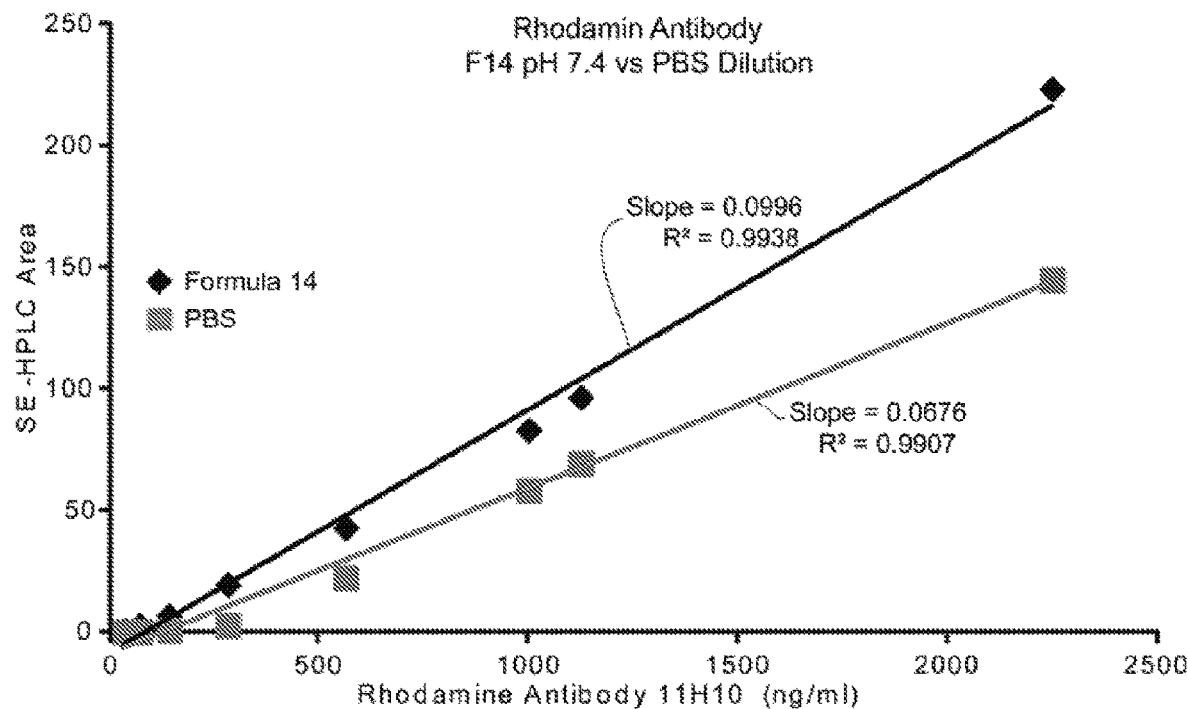
FIG. 23 shows the SE-HPLC area plots of rhodamine antibody, 11H10, diluted with formula 14 (pH 7.4) compared to dilution with PBS (pH 7.4).

Rhodamine antibody 11H10 at 1 mg/ml, was diluted to 144,000 ng/ml with Formula 14 (at pH 7.4) or PBS (pH 7.4) then further serially diluted in 1:1 steps with PBS or Formula 14 down to 35.156 ng/ml. SE-HPLC as described was performed on both matrices on a dilution range from 35.156 to 2,250 ng/ml. SE-HPLC areas for both conditions were plotted against the antibody concentration and the slope values were compared. FIG. 23 shows the plots of the area/concentrations and demonstrates a significant (p=0.008) difference between the two condition slopes. Formula 14 may also provide anti-aggregation benefit for antibodies used in immunoassay.

Example 6

Examples of Tissue Permeation of an Antibody in the Formulation: with and without Light Irradiation In certain embodiments, formulations, methods and devices are provided for the transscleral/transcorneal or transmembrane ocular delivery of biologically active molecules and compositions to a human or mammal, using photokinetic delivery methods and assemblies.

Studies into the stability of dilute mAb solutions were undertaken when the present inventors undertook the development and validation of methods for mAb photokinetic transscleral permeation. Monoclonal antibodies are usually formulated in concentrations of 1 mg/ml or higher for intraocular injections. In general, most pharmaceutical antibody preparations contain 10-150 mg antibody/ml in order to provide long term storage stability. Due to planned work with Franz cell chambers and tissue permeation, the present inventors appreciated a need to develop methods for working with dilute solutions of mAbs.

To briefly explain, the Franz cell chamber (FIG. 24) is an in vitro tissue permeation assay frequently used in transmembrane feasibility and formulation development. See Friend, D R. In vitro Skin Permeation Techniques. *Journal of Controlled Release* 18(3) (1992) 235-248. The Franz Cell apparatus consists of two primary chambers separated by a membrane such as sclera (12). The test product is applied to the membrane via the top donor chamber (14). The bottom drug recipient chamber (16) contains fluid from which samples are taken out via sample ports (24) at regular intervals for analysis. The bottom drug recipient chamber (16) includes a stir bar (18) and is placed on a magnetic stirring base (20) to insure accurate sampling of fluids from the lower chamber. The Franz cell chambers may be placed in a water bath for heating to a desired temperature. This testing determines the amount of active compound that has permeated the membrane at each point in time. In the apparatus depicted in FIG. 24, permutation with and without photokinetic stimulus can be compared by mounting an LED (10) over one of the drug donor chambers.

Published tissue permeation (Franz) cell studies typically use PBS as the recipient media at 37° C. Franz cell studies start with a recipient media void of any permeated drug. Body temperature and low drug concentrations in PBS (or other common media) contribute greatly to mAb aggregation, causing reduced measured concentrations and decreased VEGF binding activity.

As the permeation experiment progresses, the concentration of the drug in the receiver chamber increases. However, at early points in the experiment, the drug is still a very dilute solution. Therefore, a need arose in which to quickly characterize mAb dilute solutions and develop a formulation that would allow for the stabile and accurate handling of these solutions in our permeation experiments.

The drug component, whether it is in a controlled release preparation or in eye drop form, needed to be incorporated in a stable formulation. As discussed previously, Formula 14 was identified as a stabilizing formulation.

Noninvasive topical drug delivery into the eye has situational physical barriers as well as membrane limiting barriers that impede drug permeation. First, topical ocular drug delivery requires a drug formulation to be placed on the eye surface and remain in place for a period of time to allow for tissue surface adhesion and subsequent permeation. Ophthalmic administration is designed to deliver a drug on the eye, into the eye, or onto the conjunctiva. It is estimated that only one-tenth of a dose penetrates into the eye. This design challenge must be addressed in order to overcome normal eye physiology in which normal lacrimal drainage, or tear formation/drainage, continually flushes the eye surface at a rate of about 1.2 µl/min. See S. Mishima A et al. Determination of Tear Volume and Tear Flow. *Invest. Ophthalmol. Vis. Sci.* 5(3) (1966) 264-276. The tear turnover rate is 16-18% per minute. This rapid washing and turnover also accounts for loss of an ophthalmic dose in a relatively short period of time. Tear washout is collected in the nasal lacrimal duct, sometimes called the tear duct, that carries tears from the lacrimal sack of the eye into the nasal cavity. Lacrimal washing/drainage must be slowed or impeded in order to allow for an increased eye surface residency time and reduce the dilution and/or loss of the ophthalmic dose. Second, normal ocular tissue has a permeation limiting mucus layer that prevents foreign debris as well as drugs from attaching to the eye surface. This limitation may be overcome through the use of thickening agents, mucoadhesives or water soluble polymers, which would increase the formulation viscosity thereby reducing drug dose washout and increasing residency time. The longer dose contact time allows for greater drug transfer to the ocular tissues.

In one embodiment of the invention, the topical formulation provides a method of increased surface residency time. This can be achieved by the addition of one or more of thickening agents, mucoadhesives, water soluble polymers and permeation enhancement combinations thereof to formula 14.

In one embodiment, a topical formulation is provided that includes a thickening agent and/or mucoadhesive in various concentrations: for example, 0.01 to 10% w/w or 0.1 to 1% w/w or about 0.25 to 0.75% w/w in combination and additionally compounded with formula 14. The total salt concentration in the formulation can be adjusted to produce a final normal tear film osmolarity close to, or about the same range of osmolarity found in normal human tear film.

The term "bioadhesive" as used is a biocompatible polymeric material that assists in binding a biologically active agent to a target tissue. As used herein, a mucoadhesive is a subset of bioadhesives that assists in binding a biologically active agent to a mucous membrane. Mucoadhesives, bioadhesives and their derivatives include but are not limited to: water soluble polymers, hydrogels and other agents like carbopols (Carbopol® 974P NF, 980 NF, 1342 NF) methylcellulose, hydroxypropylcellulose, hydroxypropylmethylcellulose, polyacrylic acids, chitosan, N-trimethyl chitosan, N-carboxymethyl chitosan, hyaluronan, sodium hyaluronate, hyaluronic acid, cellulose acetate hydrogen phthalate, pegylated distearoyl-phosphatidylethanolamine, ethylcellulose, hydroxypropylcellulose, hydroxypropylmethylcellulose, methylmethacrylate, methylcellulose, sodium carboxymethylcellulose, poly(acrylic acid), polyalkyl cyanoacrylate, poly(epsilon-caprolacton), poly(ethylene glycol), poly(ethylene oxide), poly-N isopropylacrylamide, poly(D,L-lactic acid), poly(D,L-lactide-co-glycolide), poly(vinyl alcohol), sulfopropylmethacrylate, Xyloglucan, Xanthan gum, pullulan, dextrans, carrageenan, gelatin, starch.

In another embodiment, the topical formula provides a method to solubilize and fluidize the mucus layer that then allows the drug in the formulation to attach to the tissue surface—prolonging tissue contact residency time allowing drug permeation. This can be accomplished through the addition of a molecular complexing agent, such as a cyclodextrin, in addition or in combination with mucoadhesives, as well as without the combination with mucoadhesives to formula 14.

The topical formulation may also employ a molecular complexing agent in concentrations of, for example, 0.01 to 10% w/w or 0.1 to 1% w/w or about 0.25 to 0.75% w/w in combination with and additionally compounded with formula 14. The total salt concentration in the formulation can be adjusted to produce a final normal tear film osmolarity close to, or about the same range of osmolarity found in normal human tear film. Combinations of mucoadhesives and molecular complexing agents (e.g., cyclodextrins) with formula 14 and derivatives of formula 14 are anticipated to be compounded in the final ocular applied topical formulation and is part of the subject invention.

Increased tear formation and subsequent increased drug washout may occur due to ocular irritation from an irritating excipient, tear pH dissimilarities, or topical formulation dissimilar osmolarities. The osmolarity of the tear film equals 310-350 mOsm/kg in normal eyes and is adjusted by the principal inorganic ions $Na^+$, $K^+$, $Cl^-$, $HCO_3^-$. The mean pH value of normal tears is about 7.4. The topical formulation is adjusted by phosphate buffers or other pharmacologically acceptable formula pH buffering systems to provide a physiologic pH or a pH about the physiological pH of the ocular surface and or tear film. In another embodiment, the topical formulation is substantially similar to normal tear osmolarity and pH to minimize ocular irritation and prevent excess tear generation.

The present invention describes drug permeation enhancement through the use of pulsed infrared light. Briefly, without being bound by theory, it is hypothesized that if a drug molecule in a pharmacologically acceptable formulation is placed on the surface of the sclera/cornea and cyclically illuminated with a selected wavelength of IR light at a selected pulse rate, that drug molecule and/or tissue would absorb the light, which would result in molecular bond stretching. This cyclic molecular bond stretching and relaxing would in turn cause a molecular kinetic motion. The resulting cyclic physical shape change of the molecule and/or tissue may cause gross movement and result in the facilitated diffusion of the molecule into and through the sclera/cornea membrane. The present inventors found that IR light increased the amount of drug to permeate through scleral tissue (FIG. 25-FIG. 30). These results demonstrate that narrow wavelength incoherent (non-laser) light from an IR light emitting diode (LED) source can be used for drug delivery and that non-ionizing pulsed IR light with these characteristics is not harmful to the drug molecule or the sclera/cornea itself, which has been described earlier.

In addition to drug permeation enhancement, a drug depot effect was also observed. A drug depot effect can be defined as a body area in which a substance, e.g., a drug, can be accumulated, deposited, or stored and from which it can be distributed. It was observed that although the drug solution was in contact with the sclera for a relatively short time—one hour with concurrent IR light, and then both the drug solution and light removed—there was continuous and enhanced drug diffusion over the next 23 hours when compared to "no light" controls. The application of IR light generates a photokinetic action, thereby enhancing drug absorption into the outer layers of scleral/corneal tissue, which leads to an overall 2-3× increase in drug permeation over a prolonged amount of time. In this sense, there is improved and enhanced tissue penetration, depot effect and sustained release drug action.

One embodiment of the invention relates to compositions for photokinetic transscleral/transcorneal delivery, also referred to herein as Photokinetic Ocular Drug Delivery (PODD), of one or more biologically active substances to and through the tissues of a patient's eyes, using preferably pulsed infrared light. The composition may comprise a biologically active substance as the delivery medium.

In another embodiment of the present disclosure, the biologically active substance to be transsclerally or transcorneally delivered to a subject using the PODD system described herein is a protein. The protein may be selected from the group consisting of enzymes, non-enzymes, antibodies (including monoclonal antibodies, antibody drug conjugates and fusion proteins), and glycoproteins. In one embodiment of the invention, the protein is a humanized antibody. In accordance with yet another aspect of this embodiment of the present disclosure, the biologically active substance to be transsclerally or transcorneally delivered to a subject is a fusion protein, such as aflibercept (Eylea®, Regeneron). In accordance with a further aspect of this embodiment of the present disclosure, the protein is a monoclonal antibody selected from the group consisting of adalimumab (Humira™; Abbott), bevacizumab (Avastin™; Genentech), daclizumab (Zenapax™; Roche); etanercept (Enbril™; Amgen); infliximab (Remicade™; Centocor); ranibizumab (Lucentis™; Genentech); and rituximab (Rituxican™; Genentech).

Example 7

Photokinetic/Bevacizumab Antibody Permeation—Different IR Wavelengths

Figure 24:
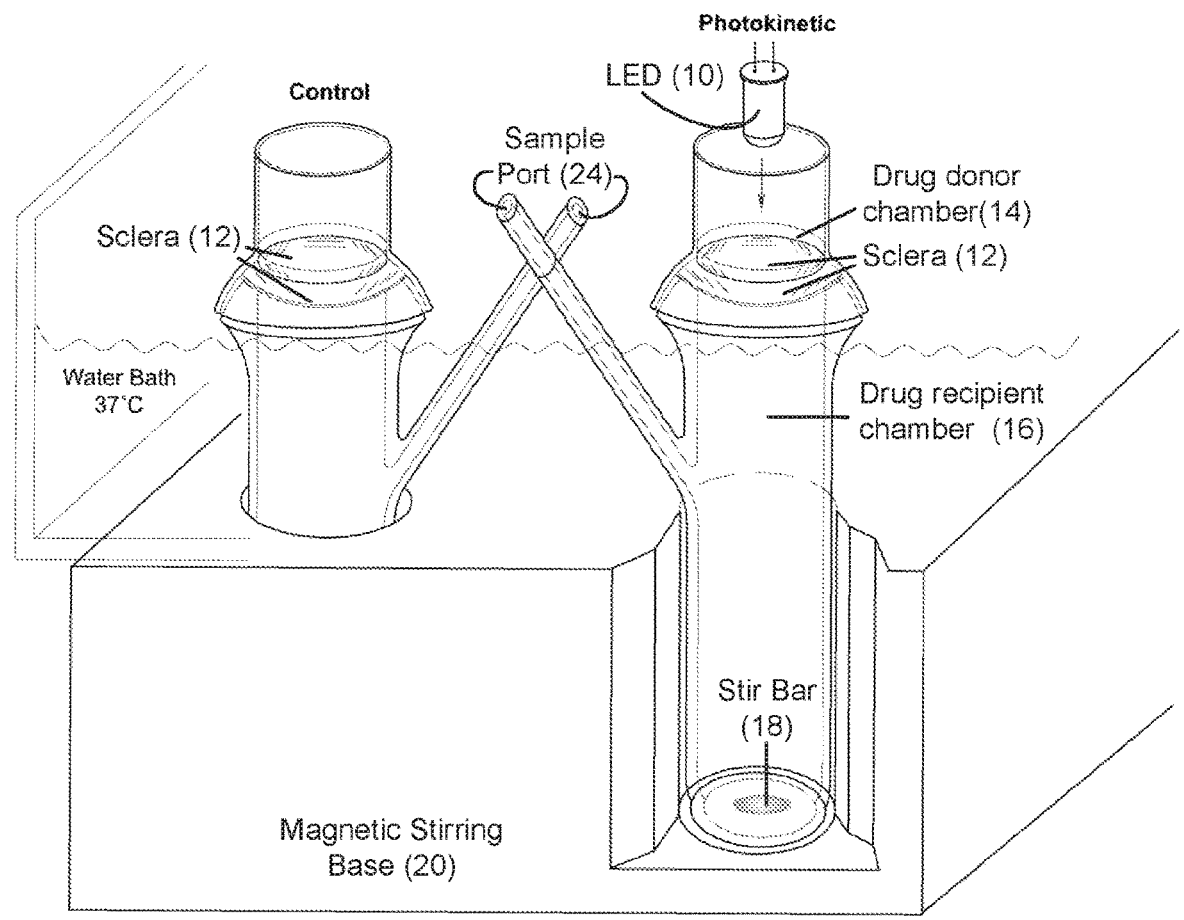
FIG. 24 is a schematic showing the vertical, spherical Franz cell diffusion apparatus.

Photokinetic/Diffusion Apparatus:

FIG. 24 shows a photokinetic testing apparatus. A vertical, spherical Franz cell diffusion apparatus as described above was adapted and used for this sclera tissue permeation model. In one embodiment, spherical Franz cells (PermeGear, Inc, Bethlehem Pa.) having a 9.1 mm diameter (0.65 cm$^2$ diffusional area) were used. A photokinetic ocular drug delivery (PODD)-modified Franz cell testing device was configured so that it accommodated the placement of IR LEDs within the donor chamber. The LEDs are placed 1 cm above the surface of the scleral membrane. The cells were placed within an aluminum block heater 37° C., on a magnetic stir bar setup (Custom manufactured by PermeGear, Inc, Bethlehem Pa.), with a custom built water bath to provide even heating. The LEDs were driven by a square wave pulse generator built by the inventors. The adjustable square wave pulse generator provided pulsed electrical energy from 400 to 1000 cycles per second (CPS) with a variable pulse width modulation duty cycle circuit. This circuit is adjustable from 0.1% to 99% percent ON pulse duration (e.g., ON 50%, OFF 50% of the time, 50% duty cycle; or ON 10%, OFF 90%, 10% duty cycle; or ON 20%, OFF 80%, 20% duty cycle and so on). The electrical current for the driver of the LEDs was adjusted to about 5 to 8 times above the continuous wave level recommended for the LED drive current in order to provide desired equivalent rated optical power output with short duration pulsed drive current. In general, the short duration electrical pulse (i.e. 10-20% duty cycle) with the over-rated drive current, allowed for temperatures slightly above ambient condition in the donor compartment. Combination adjustments in pulse widths in conjunction with electrical drive currents were used to produce the required optical power without excess or extraneous LED device heat. The temperature of the drug donor compartment did not exceed 1° C. above ambient Franz cell apparatus temperature. The experimental arrangement is shown in FIG. 24. As shown therein, Franz cells are adapted for sclera photokinetic permeation studies. A donor cell contains the test drug (in this example, bevacizumab) in formula 14. The recipient cell is filled with formula 14 as well. Samples for chemical analysis are taken from the side arm of the Franz apparatus as discussed above. Control cells are set up the same, but without the IR LED. IR LEDs are driven by a square wave pulse generator (not shown) as described above.

Drug Formulation:

Bevacizumab, ranibizumab or aflibercept was placed in formula 14. Formula 14 was used as a diluent for the drug donor solution and also used as the drug recipient media in permeation cell studies.

Tissue Protocol:

Whole globe human eye pairs are dissected into 4 sections from anterior to posterior along muscle insertion points. The 4 sections of each eye were designated to either control or photokinetic group. An anterior tissue section from limbus to equator is mounted onto a 0.65 cm$^2$ Franz cell and clamped. Both chambers of the cell are filled with degassed formula 14 and place into the 37° C. water bath/stir base and allowed to equilibrate.

Experimental Protocol:

After temperature equilibration, the donor chamber is emptied and dried. 400 ul of 2.5 mg/ml (1 mg total) of test drug in formula 14 is added into the donor chambers. The control group is held in the dark. The photokinetic group has a selected IR LED positioned 1 cm above the tissue. Experimental time starts when the drug is placed in the donor chamber and IR LED turned ON. The drug solution is removed from the donor chamber at one hour and the IR LED is turned OFF. Serial 400 ul samples are taken from the center of the recipient chamber with a 3"×20 G needle at the selected time points. Sample volume is replaced with degassed formula 14. Samples are centrifuged at 1090 relative centrifugal force to remove any tissue debris.

Statistics:

Data is presented as mean±Standard Deviation (SD). Group to group analysis was conducted with student's two-tailed t-test using Microsoft Excel. In all cases, a P value≤0.05 was considered to be significant.

Different IR Wavelengths.

In this study, 5 different IR wavelengths were tested, with bevacizumab, to identify the best condition for photokinetic drug delivery. Human sclera was used as the test membrane. The drug donor was 400 ul of 2.5 mg/ml bevacizumab in each Franz cell and was removed at one hour and LED was turned off. Samples were taken at 5 and 8 hours. The conditions tested were: 830 nm/1000 cps/5% duty cycle (ON time 5% vs OFF time 95%), 9500 nm/1000 cps/5% duty cycle, 1300 nm/1000 cps/5% duty cycle, 1450 nm/1000 cps/5% duty cycle, 3400 nm/400 cps/2.5% duty cycle. There was no heat generated from the LEDs at these duty cycles. All samples were analyzed by ELISA.

Different IR Wavelengths Results.

Figure 25A:
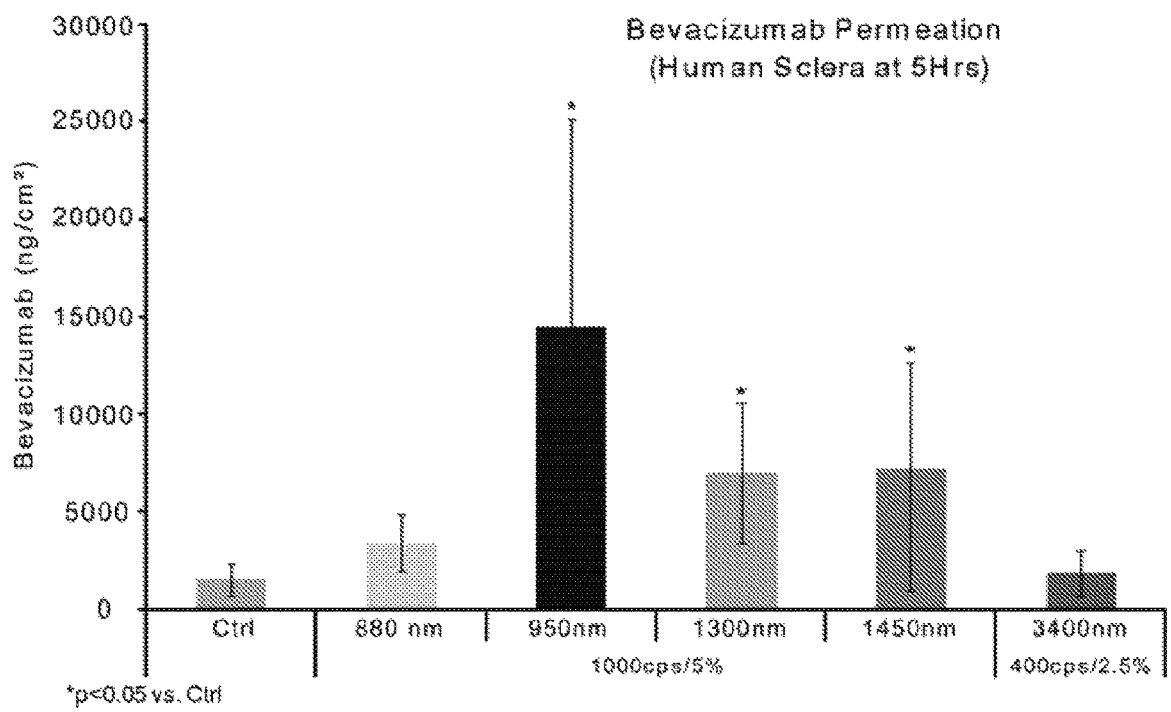
FIGS. 25A and 25B show the photokinetic/bevacizumab antibody permeation using different NIR light wavelengths.
Figure 25B:
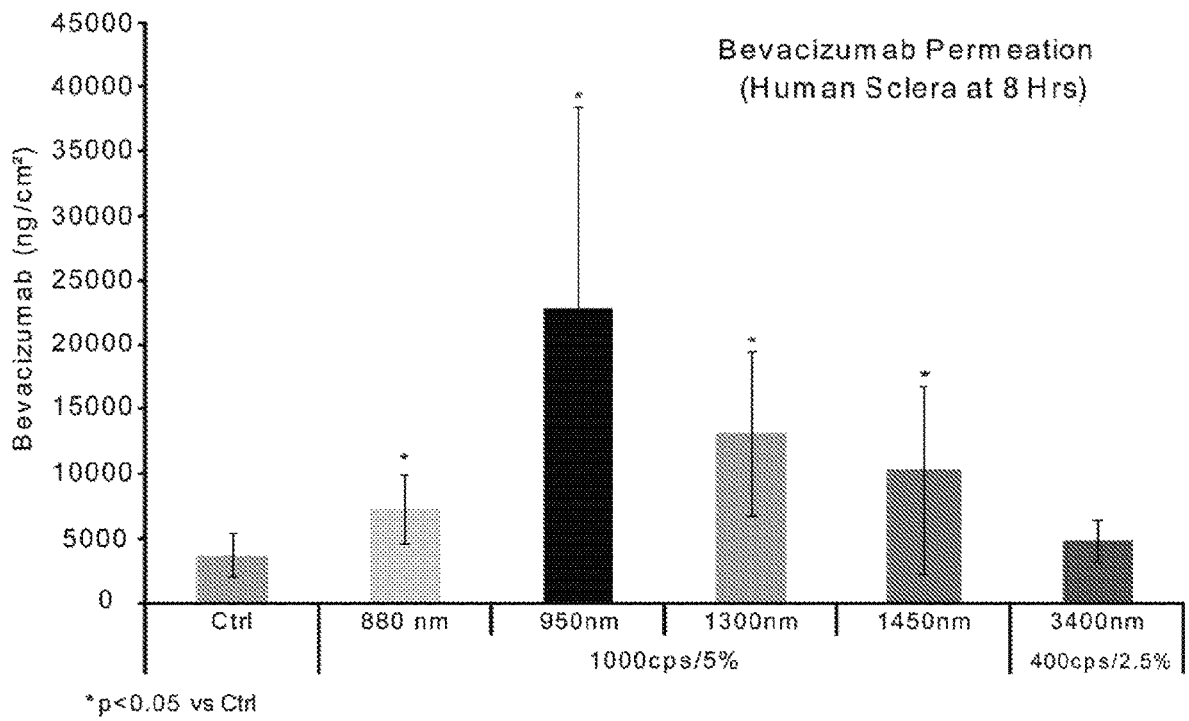

Table 3 shows the results of a study of comparing IR irradiation using different wavelengths. Samples were taken at 5 and 8 hours. As can be seen in FIG. 25, the best results were obtained from the 950 nm wavelength, when comparing 880, 950, 1300, 1450 and 3400 nm IR light.

TABLE 3

Comparison of IR irradiation using different wavelengths

| Freq (nm) | CPS | Duty Cycle | 5 Hrs. ng/ml (SD) | 8 Hrs. ng/ml (SD) |
|---|---|---|---|---|
| Control | 1000 | 5% | 1503 (814) | 3749 (1671) |
| 880 | 1000 | 5% | 3378 (1416)* | 7335 (2659)* |
| 950 | 1000 | 5% | 14500 (10630)* | 22888 (15543)* |
| 1300 | 1000 | 5% | 7009 (3588)* | 13101 (6358)* |
| 1450 | 1000 | 5% | 7206 (7371) | 10325 (9302) |
| 3400 | 400 | 2.5% | 1836 (1156) | 4816 (1625) |

*P ≤ 0.05

Example 8

Photokinetic/Bevacizumab Antibody Permeation—Same Wavelength (950 Nm), Replication Formula 14/bevacizumab replication study. An in vitro study was performed, with bevacizumab, to replicate formula 14 exposure to IR light (n=18). In this study, IR irradiation of 950 nm/1000 cps/5% duty cycle (8 mw/cm$^2$) was used. The controls were shielded from light and the IR irradiation was applied for 1 hour. After this time point, the IR light was turned off and the drug solution was removed. Samples were taken at 5, and 8 hours.

Figure 26A:
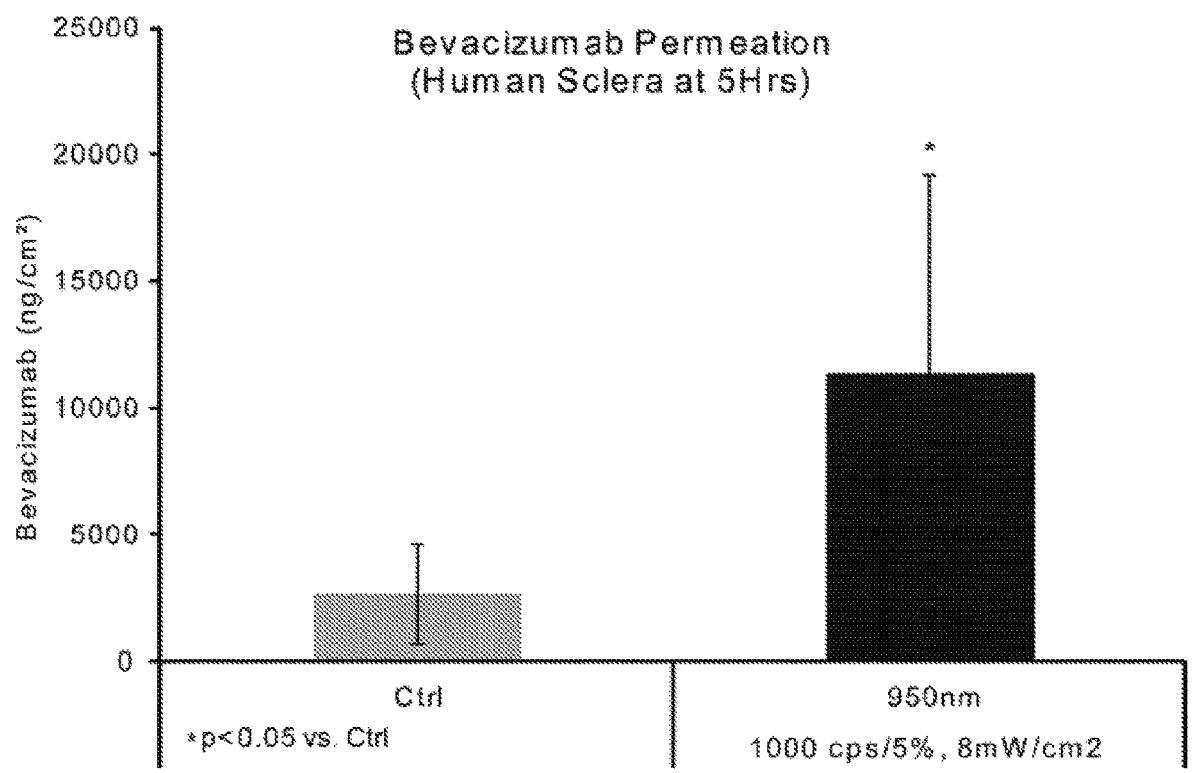
FIGS. 26A and 26B show the photokinetic/bevacizumab antibody permeation using the same wavelength (950 nm) in repeated experiments.
Figure 26B:
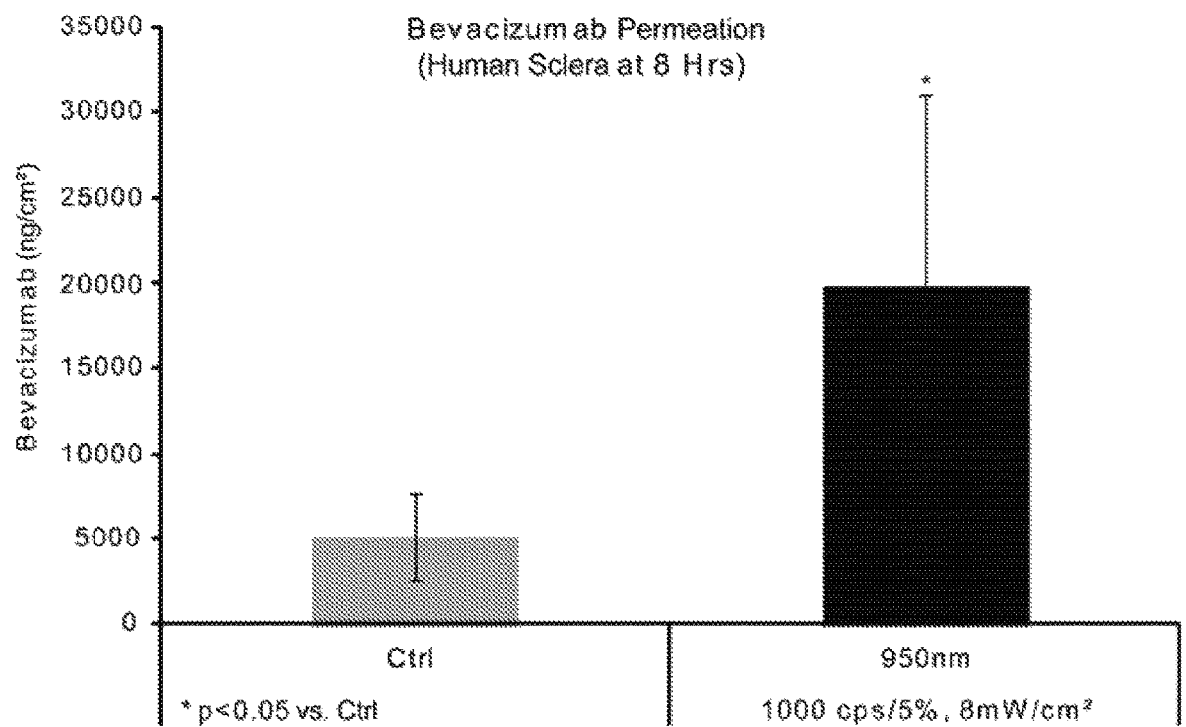

Formula 14/Bevacizumab Replication Study Results:

FIG. 26 shows the results from the replication experiments (n=18). The control bevacizumab permeation (no IR light) was 2671±1967 ng/cm$^2$ at 5 hours and 5094±2523 ng/cm$^2$ at 8 hours. The IR light irradiated samples (950 nm/1000 cps/5% duty cycle (8 mW/cm$^2$)) were 11390±7872 ng/cm$^2$ at 5 hours and 19859±11226 ng/cm$^2$ at 8 hours (n=18/group). This test successfully shows that mAbs may be evaluated using this equipment, formula and method. The results also show that using IR light significantly (p<0.05) increases transscleral drug delivery of bevacizumab, as well as providing a reliable 4× enhancement of permeation.

Example 9

Photokinetic/Bevacizumab Antibody Permeation—Same Wavelength (950 Nm), Different Duty Cycle (5% Vs. 20%)

Same Wavelength (950 nm), Different Duty Cycle (5% Vs.

20%). In this study, the same wavelength LED (950 nm) was tested, with bevacizumab at two different duty cycles, in order to study the impact of power level on photokinetic drug delivery. Human sclera was used as the test membrane. The drug donor was 400 ul of 2.5 mg/ml bevacizumab in each Franz cell and was removed at one hour and LED was turned off. Samples (400 µl) were taken at 2, 3, 5, 8, 10 and 12 hours. The conditions tested were: dark control vs 950 nm/1000 cps/5% duty cycle (8 mw/cm$^2$) and dark control vs 950 nm/1000 cps/20% duty cycle (27 mw/cm$^2$). Samples were analyzed by SE-HPLC.

Same Wavelength (950 nm), Different Duty Cycle (5% Vs. 20%) Results.

Figure 27:
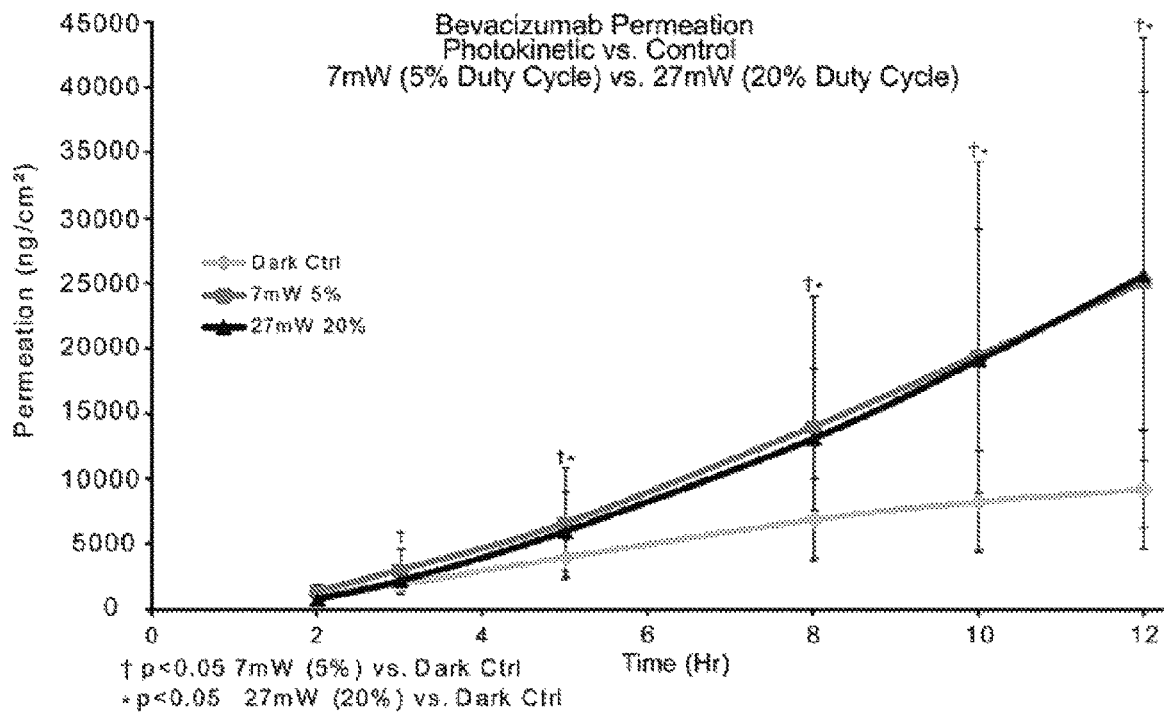
FIG. 27 shows the photokinetic/bevacizumab antibody permeation using the same light wavelength (950 nm), but using different duty cycles (5% vs. 20%).

FIG. 27 shows the results of a study comparing the power output from the LEDs (5% vs. 20% duty cycle) at a wavelength of 950 nm. Both conditions led to nearly identical results, in the controls as well as in the irradiated sclera. Judging from these results, there is no significant difference in mAb transscleral permeation when using IR light at 5% or 20% duty cycle power.

Example 10

Photokinetic/Ranibizumab Antibody Permeation—Correlation of ELISA Results to HPLC Analysis ELISA vs. HPLC.

An in vitro study using ranibizumab, was run to test the correlation of ELISA results to HPLC analysis results using formula 14 and IR light. In this study, the IR irradiation was applied for 1 hour; dark control vs 950 nm/1000 cps/20% duty cycle (27 mw/cm$^2$). The controls were shielded from light. For this experiment, a single eye donor, with 4 sclera sections per eye, was used. Right eye vs. left eye was tested. The drug donor was 400 ul of 2.5 mg/ml bevacizumab in each Franz cell and was removed at one hour and LED was turned off. Samples of 400 ul were taken at 2, 3, 5, 8, 10, 12 and 24 hours.

The samples were split in two for HPLC and ELISA analysis. HPLC analysis was started immediately. HPLC values determined ELISA dilutions. ELISA range was 1-200 ng/ml. HPLC range was 4.4-18,000 ng/ml. ELISA samples were diluted 2×-25× as determined by HPLC results. ELISA was run for the 3, 5, 8, 12 & 24 hour time points (samples from 2 hour and 10 hour time points were omitted due to limited space on the ELISA test plates).

ELISA vs. HPLC Results.

Figure 28:
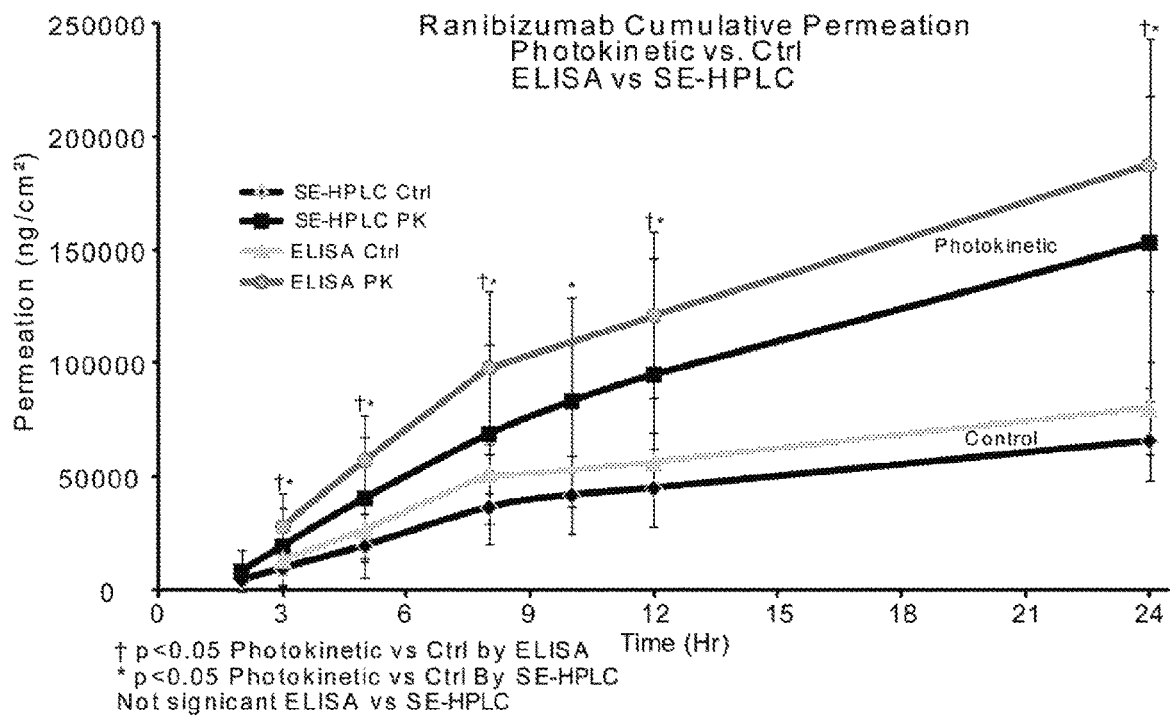
FIG. 28 shows the photokinetic/ranibizumab antibody permeation—correlation of ELISA results to HPLC analysis.

Ranibizumab by ELISA and HPLC correlate closely. The minor differences, seen in FIG. 28, are probably due to dilution factors and inherent error associated with ELISA. There are values of about ≤9% difference, therefore there is no significant difference in ELISA analysis vs HPLC analysis.

Example 11

Photokinetic/Antibody Permeation—Ranibizumab with IR 950 nm

Ranibizumab with IR 950 nm.

Ranibizumab was diluted to 2.5 mg/ml and then 400 ul (1 mg) was placed in each Franz cell (n=16). The photokinetic cells were irradiated with 950 nm light, 1000 cps, 20% duty cycle (27 mW/cm$^2$) for the exposure hour. The donor drug solution removed at one hour. Control cells were held in the dark for the exposure hour. Samples (400 µl) were taken at 2, 3, 5, 8, 10, 12 and 24 hours.

Ranibizumab with IR 950 nm Results.

Figure 29A:
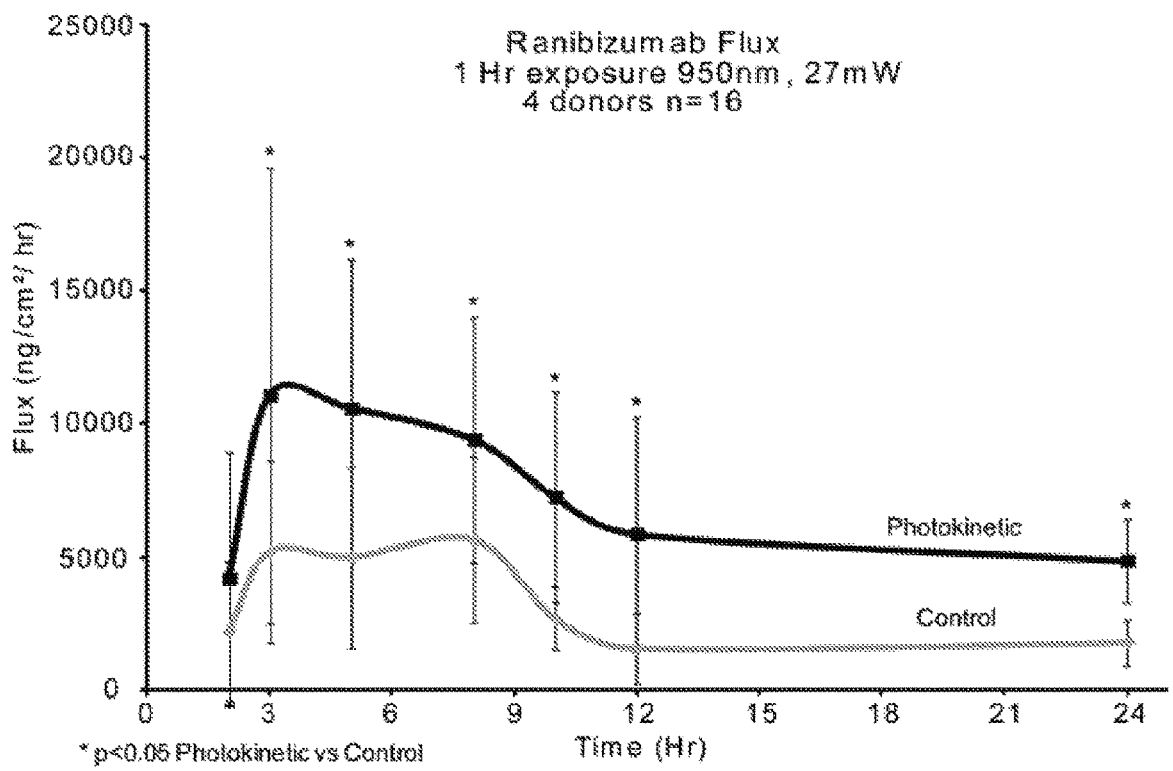
FIGS. 29A and 29B show the photokinetic/antibody permeation of ranibizumab with wavelength 950 nm NIR light.
Figure 29B:
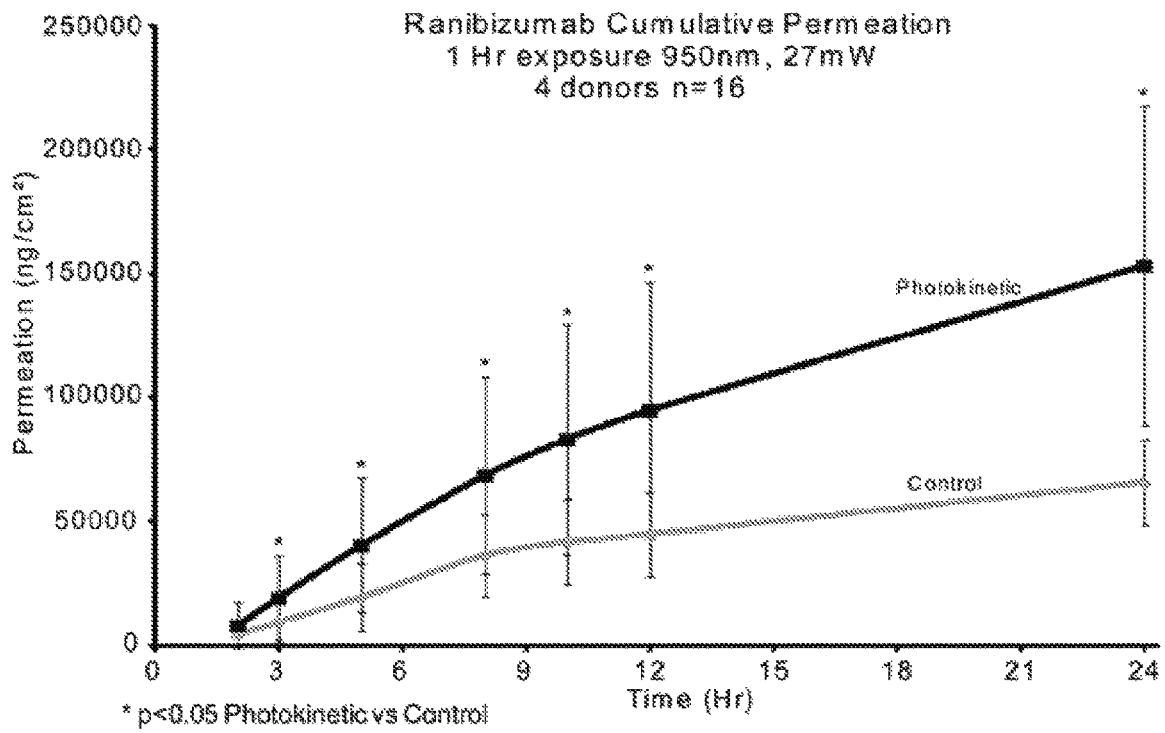

With the one hour application of ranibizumab and concurrent 950 nm IR irradiation, shown in FIG. 29A, the flux values are twice as much as the control flux values. This overall 2× increase of ranibizumab flux, when compared to control values is consistent over the 24 hour time period. The cumulative amount of drug delivered, shown in FIG. 29B, is about 2.3× when compared to controls.

Example 12

Photokinetic/Antibody Permeation—Aflibercept with IR 950 nm

Aflibercept with IR 950 nm.

Aflibercept was diluted to 2.5 mg/ml and then 400 ul (1 mg) was placed in each Franz cell. The photokinetic cells were irradiated with 950 nm light, 1000 cps, 20% duty cycle (27 mW/cm$^2$) for the exposure hour. The donor drug solution was removed at one hour. Control cells were held in the dark for the exposure hour. Samples (400 µl) were taken at 2, 3, 5, 8, 10, 12 and 24 hours.

Aflibercept with IR 950 nm Results.

Figure 30A:
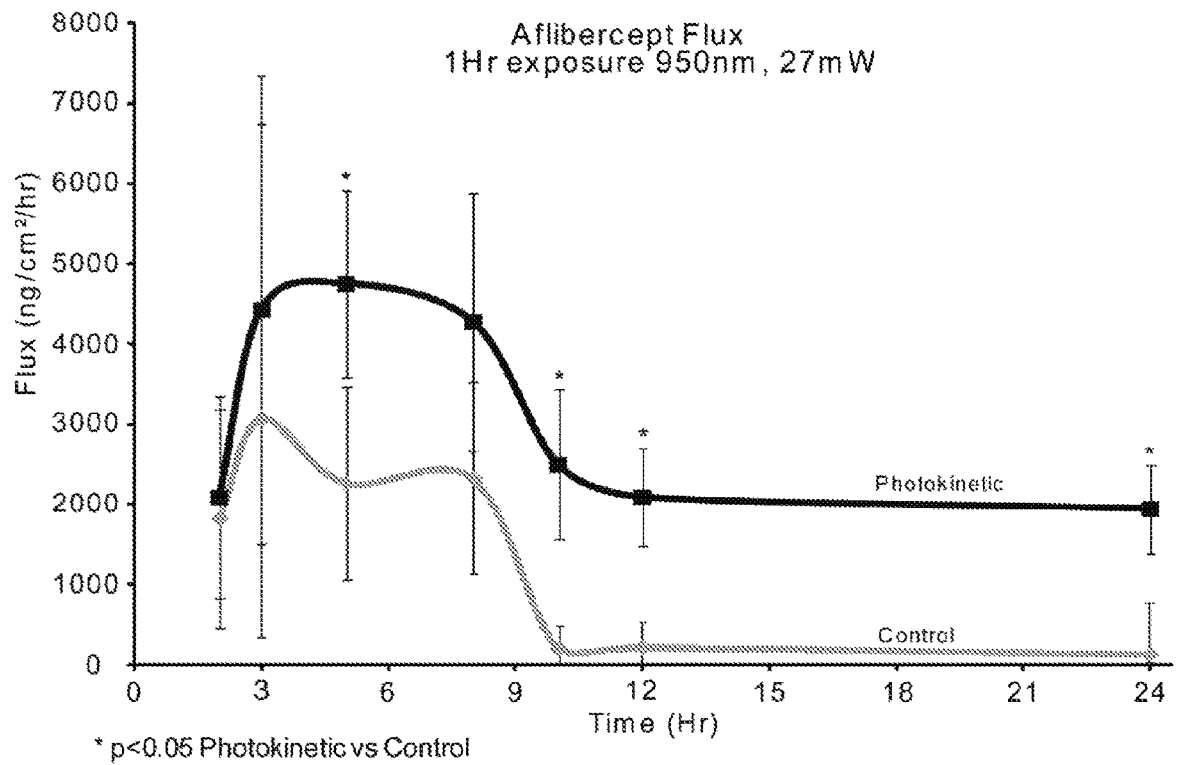
FIGS. 30A and 30B show the photokinetic/antibody permeation of aflibercept with wavelength 950 nm NIR light.
Figure 30B:
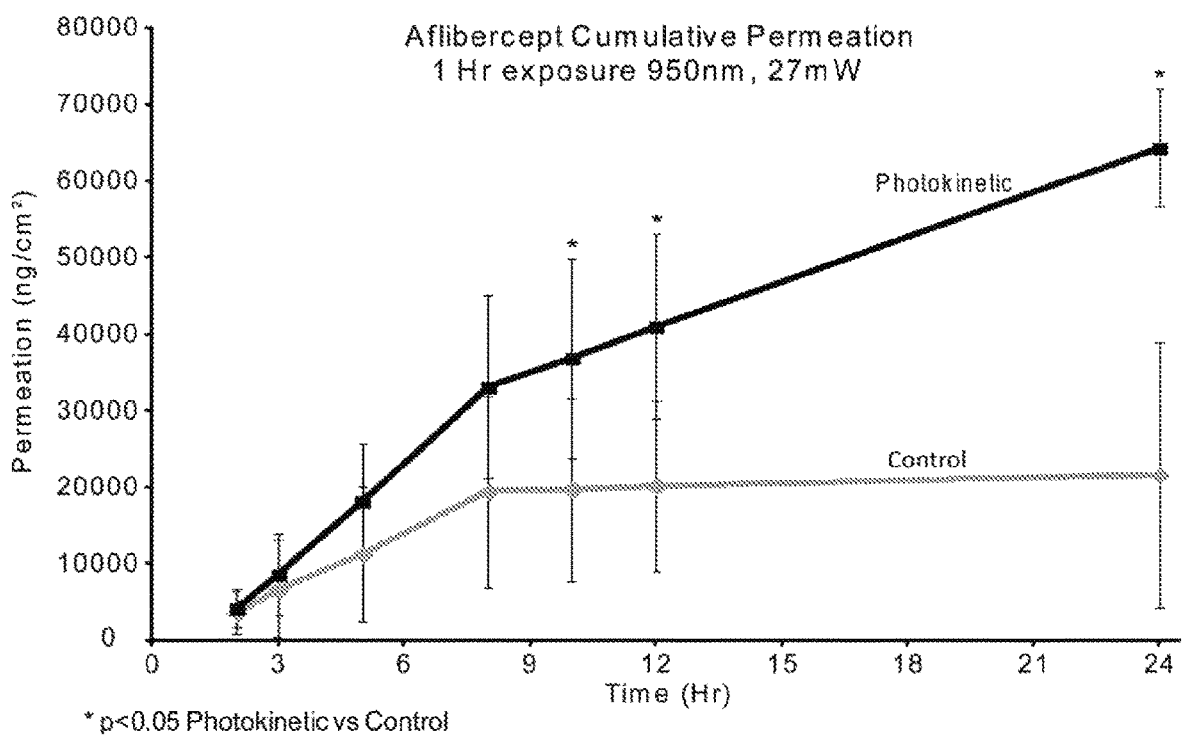

With the one hour application of aflibercept and concurrent 950 nm IR irradiation, the flux values are twice as much as the control flux values, as shown in FIG. 30A. This overall 2-3× increase of aflibercept flux, when compared to control values is consistent over the 24 hour time period. The cumulative amount of drug delivered, shown in FIG. 30B, is about 3.1× when compared to controls.

Example 13

Nebulization of an Antibody in the Formulation

Inhalation-based therapies have been extensively evaluated as site-specific method to treat pulmonary disorders due to their ability to rapidly and selectively deposit agents in the lung in greater amounts than can be readily achieved by other methods. See Kuhn, R J, *Pharmacotherapy*, Vol. 22 (2002) 80S-85S. Generally, monoclonal antibodies are systemically administered by the intravenous route to achieve high bioavailability as rapidly as possible throughout the entire body including the target sight. Direct targeting of lung tissues, with high concentrations of drug is best performed by inhalation drug delivery for example to treat lung cancer. Direct lung tissue targeting by antibodies increases availability at the target sight while reducing unnecessary systemic circulation by dilution and/or systemic side effects. See Storti, C., et. al. *Current Cancer Drug Targets*. Vol. 15(7) (2015) 604-612.

Traditional jet nebulizers and vibrating mesh nebulizers are useful to aerosolize robust drug molecules in water-thin carrier formulations. The 'water-thin' drug matrix requirement excludes the incorporation of known anti-aggregation ingredients such as trehalose in those formulations. Jet nebulizer devices also destroy fragile antibodies and protein therapeutics by the high shear forces required for aerosolization. Vibrating mesh nebulizers do not allow viscous compositions to pass through the open pores in the mesh itself and simply do not work. The aerosolization process itself causes significant drug aggregation within the aerosolized droplet if not corrected by the drug carrier matrix. See Respaud R., et. al. *MAbs*. 6 (5) (2014) 1347-55. The anti-aggregation composition disclosed herein comprises a 7.5% concentration of trehalose rendering the composition somewhat viscous. This viscous composition and any composition that may also or alternately comprise a mucoadhesive cannot be aerosolized using a jet or vibrating mesh nebulizers.

A new nebulizer design was developed in order to convert viscous formulations of various therapeutic agents into aerosols having the desired particle size in the desired range of 2 µm to 12 µm while producing minimal shear forces. See Kraft E R, et al. Pulse drug nebulization systems, formulations therefore, and methods of use. U.S. Pat. No. 8,776,786. Regardless of the aerosolization method employed, reduced antibody activity caused by antibody aggregation induced or allowed by the carrier matrix would persist even if the antibody or protein therapeutic structurally survived the aerosolization process that produces inspirable drug droplets. There is a need for a suitable carrier for aerosolized antibodies to prevent aggregation regardless of the aerosolization device used. See Respaud R., et. al. *Expert Opinion on Drug Delivery*. 12 (6) (2015) 1027-1039. Furthermore, the aerosolization device must be able to produce inspirable droplets from a composition that is more viscous than water.

Certain poloxamer surfactants have been shown to aid in drug uptake when applied to mucus membranes by solubilizing the mucus and water layer found on the membrane surface. The term "poloxamer" refers to a tri-block copolymer composed of polypropylene oxide and polyethylene oxide. The term "block co-polymer" means a polymer composed of two or more different polymers ("co-polymer") arranged in segments or "blocks" of each constituent polymer. Polypropylene oxide (POP or polyoxypropylene, has the formula $(C_3H_6O)_x$ and a subunit mw of 58) is a hydrophobe. Polyethylene oxide (POE or polyoxyethylene has the formula $(C_2H_4O)_x$ and a subunit mw of 44) is a hydrophile. The common chemical name for poloxamers is polyoxypropylene-polyoxyethylene block copolymer. The CAS number is 9003-11-6. The poloxamers vary in total molecular weight, polyoxypropylene to polyoxyethylene ratio, surfactant properties and physical form in undiluted solution. Physical forms include Liquids (L), Pastes (P) and Flakable solids (F), determined largely by the relative percentage of hydrophobic versus hydrophilic components.

PLURONIC® is a trademark for poloxamers manufactured by BASF. In Europe the pharmaceutical grade poloxamers manufactured by BASF are sold under the mark Lutrol. Poloxamers are tri-block copolymers in which the hydrophobe propylene oxide (PO or PPO) block is sandwiched between two hydrophile ethylene oxide (PE or PEO) blocks, in accordance with the following general formula and structure:

$$HO-(CH_2CH_2O)_x-(CH_2\overset{\underset{\displaystyle CH_3}{|}}{C}HO)_y-(CH_2CH_2O)_{x'}-H$$

| EO | PO | EO |

In the nomenclature of poloxamers, the non-proprietary name "poloxamer" is followed by a number, the first two digits of which, when multiplied by 100, equals the approximate molecular weight ("mw") of the polyoxypropylene ("POP") and the third digit, when multiplied by 10 equals the approximate % by weight of the polyoxyethylene ("POE"). Thus, poloxamer 188 would have an average POP mw of approximately 1800 and an average POE % of 80%. In actual practice, poloxamers are typically synthesized according to a process in which a hydrophobe of the desired molecular weight is generated by the controlled addition of propylene oxide to the two hydroxyl groups of propylene glycol followed by addition of ethylene oxide to sandwich the hydrophobe between hydrophilic groups. The process results in a population of molecules in a relatively circumscribed range of a molecular weights characterized by a hydrophobe having a defined average molecular weight and total average percentage of hydrophile groups.

BASF has long been one of the leading poloxamer manufacturers in the world and the BASF designations for poloxamers they manufacture are very commonly used in the industry leading to some confusion. For example, poloxamer-108 is sold by BASF as PLURONIC® F38, poloxamer-188 as PLURONIC® F68, poloxamer-237 as PLURONIC® F87, poloxamer-238 as PLURONIC® F88, poloxamer-338 as PLURONIC® F108NF and poloxamer-407 as PLURONIC® F127. Liquid form poloxamers-124 is sold by BASF as PLURONIC® L44NF and poloxamer-401 as PLURONIC® L121.

In the BASF nomenclature, a letter describing the physical form of the poloxamer (whether Liquid "L", Paste "P" or Flakable "F") is followed by a first number arbitrarily representing the molecular weight of the POP step-wise up a "y" axis of a PLURONIC grid and the second number representing the % POE. BASF developed the PLURONIC grid to provide a graphic representation of the relationship between copolymer structure, physical form and surfactant characteristics acknowledging that both the ratio and weights of EO and PO vary within this family of surfactants.

On the PLURONIC® surfactant grid the molecular weight ranges of the hydrophobe (propylene oxide) are plotted against the weight-percent of the hydrophile (ethylene oxide) present in each molecule. Poloxamer species defined by their location on the PLURONIC® grid can be expected to have shared properties that are a function of their total molecular weight and relative hydrophobicity. As used herein, the phrase "having the characteristics of" a particular poloxamer means those poloxamers that exhibit copolymer structure, physical form and surfactant characteristics similar to those of the named poloxamer.

PLURONIC poloxamers have been used in nasal formulations (Pisal, S S. et al, Pluronic gels for nasal delivery of Vitamin B12. Part I: Preformulation Study. *International Journal of Pharmaceutics* 270 (2004) 37-45), ocular (Desai, S D, Blanchard, J. Evaluation of Pluronic F127-Based Sustained-Release Ocular Delivery Systems for Pilocarpine Using the Albino Rabbit Eye Model. *Journal of Pharmaceutical Sciences*. 87(10) (1998) 1190-1195), and other drug delivery situations, and have been shown to greatly enhance membrane permeation in those situations. See Batrakova, E V, Kabanov, A V. Pluronic block copolymers: Evolution of drug delivery concept from inert nanocarriers to biological response modifiers. *Journal of Controlled Release*. 130 (2008) 98-106.

Problematically, poloxamers are viscous and cannot be aerosolized in traditional jet or vibrating mesh nebulizers, so their use in compositions for aerosolization/nebulization pulmonary drug delivery has not been realized. The present inventors thus adapted the nebulizing system described in U.S. Pat. No. 8,776,786 to aerosolize a poloxamer containing composition. A composition comprising 5% PLURONIC® F127 as an additional ingredient to the subject formula 14 was included in the composition groups to determine if first, a poloxamer composition could in fact be aerosolized into suitable respirable droplets for pulmonary delivery and second, if the inclusion of PLURONIC® F127 either negatively or positively affected aerosolization of antibody survivability and function.

A microchannel concentric tube nebulizing apparatus was constructed and was used to aerosolize four antibody compositions. Appropriate gases for use in nebulization in accordance with the present disclosure include oxygen, oxygen mixtures, nitrogen, argon, helium, and purified air, as well as combinations of these gases in various proportions (e.g., 70% oxygen, 30% nitrogen). While the outer tube and the inner microtube are illustrated to be substantially cylindrical in shape, those of skill in the art will appreciate that they can also be of any appropriate shape, providing such shape provides the same advantageous flow rates and particle sizes as the illustrated arrangement.

One embodiment of such a nebulizer is depicted in FIG. 32A-FIG. 32C. As shown in FIG. 32A, the microchannel concentric tube nebulizing apparatus comprises at least one nebulizing nozzle (31) in fluid communication with a drug reservoir via drug inlet (42) wherein the nebulizing nozzle comprises an outer carrier gas delivery tube (30) spaced apart from and disposed around at least one inner drug delivery tube (36) and wherein the outer carrier gas delivery tube and the at least one inner drug delivery tube(s) share a longitudinal axis and are together dimensioned and disposed such that expulsion of a carrier gas (44) through the outer carrier gas delivery tube forms an outer surrounding stream of carrier gas that educts and carries an inner flow of fluid (46) from the drug reservoir in a center of carrier gas flow exiting the nebulizing nozzle and thereby produces aerosol drug containing droplets having a particle size ranging from about 2 μm to about 12 μm in median mass aerodynamic size. As shown in FIGS. 32B and 32C, for the working example (not to scale), the rigid fluid inner tube (36) had an internal opening (34) of about 0.006" ($D_4$) and an outside dimension ($D_1$) of about 0.012". The fluid tube was fitted inside a rigid nebulizing gas tube (30) with an inside opening ($D_2$) of about 0.016" thereby leaving a space (32) of approximately 0.0000879 $in^2$ around the inner fluid tube as an aerosolization gas pathway. The inner fluid tube end (50) protruded about 0.005" ($D_5$) from the end of the nebulizing gas tube (52). It was found that this small protrusion profoundly affected the droplet size distribution of the aerosol. As the fluid elutes from the inner fluid tube, the surrounding air flow pulls the fluid from the fluid tube opening and causes the fluid to form aerosol droplets in the 2-12 μm range. While the outer tube (30) and the inner microtube (36) are illustrated to be substantially cylindrical in shape, those of skill in the art will appreciate that they can also be of any appropriate shape, providing such shape provides the same advantageous flow rates and particle sizes as the illustrated arrangement.

Post aerosolized condensed samples of the antibody aerosol were then analyzed by SE-HPLC using methods described elsewhere herein. Bevacizumab was chosen as the model drug. Briefly, bevacizumab, 25 mg/ml, was diluted w/w to 2.5 mg/ml with one of 4 solutions: 1) Formula 14; 2) Formula 14 including 5% Pluronic F127; 3) Normal saline (0.9% NaCl in water); and 4) PBS. The individual solutions were place in plastic syringes and held until use.

Each of the four antibody carrier compositions in individual syringes were placed in a mechanical syringe pump. Flexible plastic tubing was fitted between the syringe and the fluid delivery tube. The isolated nebulizing gas outer tube was fitted with a flexible plastic tube and attached to an air supply delivering a static pressure of 50 psi. Direct airflow measurement were performed with an inverted graduated water column receiving the air flow from the nebulizing nozzle and found to have a volume delivery of about 0.9 liters of air/minute. The syringe pump was set to deliver about 0.1 ml/minute of antibody carrier composition into the nebulizing nozzle. The nebulizing air to fluid volume ratio was about 9000:1. The outflow of aerosolized antibody composition nebulized into small droplets was directed into a 50 ml conical tube where it condensed into a fluid. The nebulization procedure was performed for 45 minutes.

The condensed nebulized fluid was then diluted w/w with the individual carrier matrix to 144 μg/gram (144000 ng/ml). This matrix was further diluted v/v in 50% steps down to 140.62 ng/ml with an intermediate dilution of 1000 ng/ml as previously described. The individual dilutions were then analyzed by SE-HPLC as previously described. Table 4 shows the slopes for the carrier matrices separated into low (140-100 ng/ml) and high concentrations (1125-144000 ng/ml).

TABLE 4

Bevacizumab Nebulized

| Formula | 140-1000 ng/ml Slope | $R^2$ | 1125-144000 ng/ml Slope | $R^2$ |
|---|---|---|---|---|
| Formula 14 | 0.2114 | 0.9998 | 0.2304 | 1.0000 |
| F 14 + 5% Pluronic F127 | 0.1910 | 0.9975 | 0.2096 | 1.0000 |
| PBS | 0.0004 | 0.7580 | 0.1808 | 0.9998 |
| Saline 0.9% | 0.0145 | 0.7357 | 0.1464 | 0.9992 |

Figure 31:
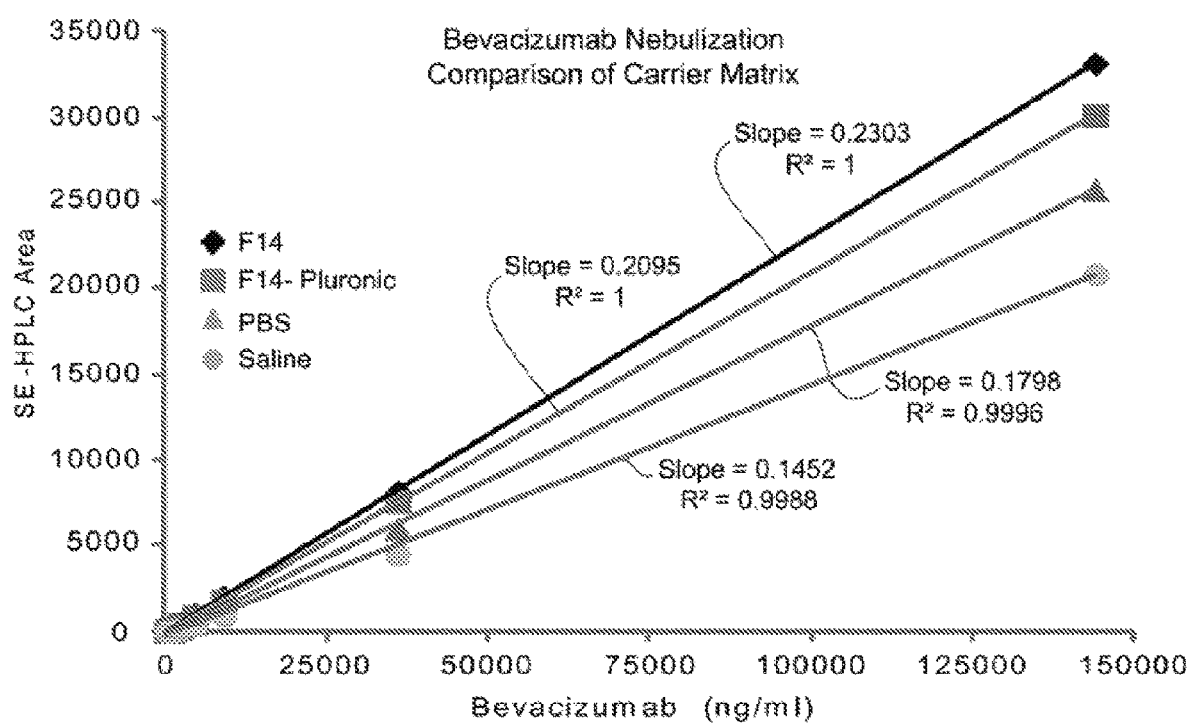
FIG. 31 shows the results from the aerosol study. The slopes of each of the compositions (bevacizumab, 25 mg/ml diluted w/w to 2.5 mg/ml with one of 4 solutions: 1) Formula 14; 2) Formula 14 with 5% Pluronic F127; 3) Normal saline (0.9% NaCl in water); and 4) PBS over the entire range of 140-144000 ng/ml are shown.

Table 4 shows that PBS and saline do not protect the antibody from degradation at low concentrations, while formula 14 and formula 14 supplemented with 5% PLURONIC F127 provide near linear slope values over the entire concentration range of 140-144000 ng/ml. FIG. 31 shows the slopes of each of the compositions over the entire range of 140-144000 ng/ml.

Surprisingly, the viscous composition containing the PLURONIC F127 produced droplets in the 2-12 μm range suitable for pulmonary delivery. This demonstrates that the aerosolization using formula 14 as well as formula 14 supplemented with 5% PLURONIC F127 are suitable drug carrier matrices for aerosol delivery of antibodies and protein therapeutics for lung delivery.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

We claim:

1. A pharmaceutical formulation comprising a stabilizing aqueous solution admixed with a proteinaceous molecule at a final concentration less than 3 mg/ml, wherein the proteinaceous molecule is selected from one or more of the group consisting of antibodies, antibody fragments, antibody-drug conjugates, antibody related products, and recombinant fusion protein molecules, and wherein the stabilizing aqueous solution comprises:
    a. trehalose in an amount from about 6% to about 10%;
    b. arginine in an amount from about 8 mM to about 12 mM;
    c. a salt selected from a sodium chloride (NaCl) and a potassium chloride (KCl) and, combinations thereof in an amount from about 0.1% to about 0.9%;
    d. polysorbate 80 in an amount from about 0.01% to about 0.05%; and
    e. a phosphate buffer in a concentration of about 50 mM to about 150 mM adjusted to provide a solution pH of 6.0 to 7.8.

2. The pharmaceutical formulation of claim 1, comprising α,α-trehalose in an amount of about 7.5%, L-arginine in an amount of about 10 mM, Na Cl in an amount of about, 0.3%, polysorbate 80 in an amount of about 0.04%, and a sodium phosphate buffer at a concentration of 50 mM to 150 mM adjusted to provide a solution pH of 6.6 to 7.8.

3. The pharmaceutical formulation of claim 1, comprising 7.5% α,α-trehalose, 10 mM L-arginine, 0.3% NaCl, 0.04% polysorbate 80, and 100 mM sodium phosphate buffer at a pH of 6.78 to 7.8.

4. The pharmaceutical formulation of claim 1, further comprising one or more of a thickening agent, a bioadhesive, an antioxidant, a poloxamer, and a molecular, complexing agent.

5. The pharmaceutical formulation of claim 4, wherein the bioadhesive, is hyaluronic acid, the antioxidant is glutathione, wherein the poloxamer has a structure, physical, form and surfactant properties of a poloxamer 407, and the molecular complexing agent is a cyclodextrin.

6. The pharmaceutical formulation of claim 1, wherein the proteinaceous molecule is an anti-VEGF agent.

7. The pharmaceutical formulation of claim 1, wherein the formulation is selected from the group consisting of a topical ocular pharmaceutical formulation, a parenteral formulation, an inhalable pulmonary pharmaceutical formulation, an intradermal pharmaceutical formulation, and an enteral pharmaceutical formulation.

8. The pharmaceutical formulation of claim 1, wherein the stabilizing aqueous solution is degassed prior to admixture with the proteinaceous molecule.

9. The pharmaceutical formulation of claim 6, wherein the anti-VEGF agent is selected from the group consisting of bevacizumab, ranibizumab, and aflibercept.

10. The pharmaceutical formulation of claim 1, wherein the formulation is a topical ophthalmic pharmaceutical formulation.

11. The stabilizing aqueous solution of claim 1, wherein the proteinaceous molecule at a final concentration of about 3.9 ng/ml to about 6000 ng/ml.

12. The stabilizing aqueous solution of claim 1, wherein the proteinaceous molecule at a final concentration less than 1 mg/ml.

13. The stabilizing aqueous solution of claim 1, wherein the proteinaceous molecule at a final concentration less than 0.01 mg/ml.

14. The stabilizing aqueous solution of claim 1, wherein the proteinaceous molecule at a final concentration less than 1,150 ng/ml.

* * * * *